(12) United States Patent
Willis et al.

(10) Patent No.: US 8,658,223 B2
(45) Date of Patent: Feb. 25, 2014

(54) INSECTICIDAL COMPOSITIONS AND METHODS OF USING THE SAME

(75) Inventors: Michael Dean Willis, Elgin, IL (US); Marie Elizabeth Saunders, Schaumburg, IL (US); Darryl Ramoutar, Geneva, IL (US); Joanna Maria Szymczyk, Chicago, IL (US); Frances Nita Krenick, Schaumburg, IL (US); Andrea Rohrbacher, Lake Zurich, IL (US)

(73) Assignee: Clarke Mosquito Control Products, Inc., Roselle, IL (US)

( * ) Notice: Subject to any disclaimer, the term of this patent is extended or adjusted under 35 U.S.C. 154(b) by 0 days.

(21) Appl. No.: 13/548,998

(22) Filed: Jul. 13, 2012

(65) Prior Publication Data

US 2013/0101687 A1 Apr. 25, 2013

Related U.S. Application Data

(60) Provisional application No. 61/507,557, filed on Jul. 13, 2011, provisional application No. 61/543,180, filed on Oct. 4, 2011, provisional application No. 61/580,427, filed on Dec. 27, 2011.

(51) Int. Cl.
 *A01N 65/00* (2009.01)

(52) U.S. Cl.
 USPC .......................................................... 424/725

(58) Field of Classification Search
 None
 See application file for complete search history.

(56) References Cited

U.S. PATENT DOCUMENTS

| | | | |
|---|---|---|---|
| 3,516,608 A | 6/1970 | Brown et al. | |
| 3,991,213 A | 11/1976 | Mitsubayashi | |
| 4,803,289 A | 2/1989 | Laurence et al. | |
| 4,855,133 A | 8/1989 | Kamei et al. | |
| 4,970,068 A | 11/1990 | Wilson et al. | |
| 4,985,413 A | 1/1991 | Kohama et al. | |
| 5,698,210 A | 12/1997 | Levy | |
| 5,846,553 A | 12/1998 | Levy | |
| 5,858,384 A | 1/1999 | Levy | |
| 5,858,386 A | 1/1999 | Levy | |
| 5,885,606 A | 3/1999 | Kawada | |
| 5,928,634 A | 7/1999 | Uick et al. | |
| 5,968,540 A | 10/1999 | Brenner et al. | |
| 5,983,557 A | 11/1999 | Perich et al. | |
| 6,041,543 A | 3/2000 | Howse | |
| 6,054,141 A | 4/2000 | Mayer et al. | |
| 6,185,861 B1 | 2/2001 | Perich et al. | |
| 6,190,652 B1 | 2/2001 | Pair et al. | |
| 6,306,416 B1 | 10/2001 | McKibben et al. | |
| 6,316,017 B1 | 11/2001 | McKibben et al. | |
| 6,335,027 B1 | 1/2002 | Levy | |
| 6,337,078 B1 | 1/2002 | Levy | |
| 6,346,262 B1 | 2/2002 | Levy | |
| 6,350,461 B1 | 2/2002 | Levy | |
| 6,387,386 B1 | 5/2002 | Levy | |
| 6,389,740 B2 | 5/2002 | Perich et al. | |
| 6,391,328 B1 | 5/2002 | Levy | |
| RE37,890 E | 10/2002 | Levy | |
| 6,585,990 B1 | 7/2003 | Huang | |
| 6,599,539 B1 | 7/2003 | Taylor | |
| 6,821,526 B1 | 11/2004 | Huang | |
| 6,916,469 B2 | 7/2005 | Rojas et al. | |
| 7,122,176 B2 | 10/2006 | Stamets | |
| 7,793,920 B2 | 9/2010 | Bauer et al. | |
| 7,914,777 B2 | 3/2011 | Rojas et al. | |
| 7,951,388 B2 | 5/2011 | Stamets | |
| 7,951,389 B2 | 5/2011 | Stamets | |
| 8,084,052 B1 | 12/2011 | Mason et al. | |
| 2001/0006685 A1 | 7/2001 | Watanabe et al. | |
| 2002/0146394 A1 | 10/2002 | Stamets | |
| 2003/0198659 A1 | 10/2003 | Hoffmann et al. | |
| 2006/0111403 A1 | 5/2006 | Hughes et al. | |
| 2006/0233848 A1 | 10/2006 | Patel et al. | |
| 2007/0020304 A1 | 1/2007 | Tamarkin et al. | |
| 2009/0010979 A1 | 1/2009 | Baker et al. | |
| 2009/0181850 A1 | 7/2009 | Stern et al. | |
| 2009/0277074 A1 | 11/2009 | Noronha et al. | |
| 2009/0304624 A1 | 12/2009 | Gutsmann et al. | |
| 2010/0158965 A1 | 6/2010 | Beitzel et al. | |
| 2010/0192451 A1 | 8/2010 | Ponnusamy et al. | |
| 2010/0192452 A1 | 8/2010 | Kupfer et al. | |
| 2010/0223837 A1 | 9/2010 | Borth et al. | |
| 2010/0247480 A1 | 9/2010 | Kupfer et al. | |
| 2010/0322892 A1 | 12/2010 | Burke | |

(Continued)

FOREIGN PATENT DOCUMENTS

| EP | 446464 | 12/1990 |
|---|---|---|
| JP | 11-60421 | 3/1999 |

(Continued)

OTHER PUBLICATIONS

Colby, S.R. "Calculating Synergistic and Antagonistic Responses of Herbicide Combinations", Weeds 1967, 15, 20-22.

(Continued)

*Primary Examiner* — Michael Meller

(74) *Attorney, Agent, or Firm* — Michael Best & Friedrich LLP

(57) ABSTRACT

Insecticidal compositions have at least one active agent and at least one insecticide. The active agent can include *perilla* oil, a component found in *perilla* oil, or a perillaldehyde or carvone analog. The insecticide can include a pyrethrum, pyrethrin, pyrethroid, neonicotinoid, chlofenapyr, ethiprole, sulfoxaflor, carbamate, organophosphate, or organochlorine. Methods for controlling insects include contacting an insect with an effective amount of a composition described in this specification. Modified plants that produce an active agent can be contacted with an insecticide.

18 Claims, 2 Drawing Sheets

(56) References Cited

U.S. PATENT DOCUMENTS

| | | |
|---|---|---|
| 2011/0152077 A1 | 6/2011 | Ilg et al. |
| 2011/0184040 A1 | 7/2011 | Taranta et al. |
| 2011/0200551 A1 | 8/2011 | Stamets |
| 2011/0236451 A1 | 9/2011 | Taranta et al. |
| 2012/0039976 A1 | 2/2012 | Stamets |
| 2013/0005688 A1 | 1/2013 | Saunders et al. |
| 2013/0067795 A1 | 3/2013 | Wesson et al. |

FOREIGN PATENT DOCUMENTS

| | | |
|---|---|---|
| JP | 2005-075753 | 3/2005 |
| WO | WO 8604897 | 8/1986 |
| WO | WO 9000005 | 1/1990 |
| WO | WO 9524124 | 9/1995 |
| WO | WO 9923875 | 5/1999 |
| WO | WO 0228189 | 4/2002 |
| WO | WO 2005015993 | 2/2005 |
| WO | WO 2008657561 | 5/2008 |
| WO | WO 2010127019 | 11/2010 |
| WO | 2013-010099 | 1/2013 |

OTHER PUBLICATIONS

"Pyrethrins & Pyrethroids" 1998 Fact Sheet published by the National Pesticide Telecommunications Network (NPTN) at Oregon State University, Corvallis, Oregon (6 pages).

EPA Office of Pesticide Programs Memorandum "Pyrethroids: Evaluation of Data from Developmental Neurotoxicity Studies and Consideration of Comparison Sensitivity" Jan. 20, 2010 (36 pages).

Smitt, O., "Syntheses of Allelochemicals for Insect Control" (2002), Mid Sweden University, (58 pages).

Valent, "Material Safety Data Sheet," Valent Bio Sciences Corporation, Aug. 23, 2007 (9 pages).

PCT/US2012/46718 International Search Report and Written Opinion dated Dec. 7, 2012, (10 pages).

FIGURE 1

INSECTICIDAL COMPOSITIONS AND METHODS OF USING THE SAME

CROSS-REFERENCE TO RELATED APPLICATIONS

This application claims the benefit of priority to U.S. Provisional Patent Applications Nos. 61/507,557 filed on Jul. 13, 2011, 61/543,180, filed on Oct. 4, 2011, and 61/580,427, filed on Dec. 27, 2011. The entire contents of each of these applications are incorporated into this specification by reference in their entireties.

FIELD

This specification relates to compositions and methods useful for insect control.

BACKGROUND

Many types of insecticides have been used to kill mosquitoes and other insect pests. Nevertheless, many insecticides have disadvantages. Some insecticides are toxic to humans, are harmful to the environment, or have limited efficacy. Further, there is an increasing demand for compositions containing naturally occurring or so-called organic compounds. Accordingly, there is a continuing need for organic compounds having improved insecticidal properties, while being substantially non-toxic or only mildly toxic to humans.

Certain plant species produce essential oils that serve as natural sources of insect repellents, insecticides, fragrances, or other useful chemicals. For example, *perilla* oil and certain of its components have been used in a variety of applications, including in varnishes, in the production of inks and linoleums, and in the culinary field as a marinade.

*Perilla* oil is extracted from annual herbs belonging to the genus *Perilla* through several methods, including but not limited to cold pressing of the seeds or steam distillation of the leaves. Two types of *perilla* oil are available, seed and leaf extracts. The major component of perilla seed extract is linolenic acid, and the major components of perilla leaf extract are perillaldehyde, limonene, β-caryophyllene, and farnesene.

SUMMARY

This specification demonstrates the ability of *perilla* oil and some of its components to act as a synergist of insecticides such as pyrethrum, pyrethrins, pyrethroids, spinosad, neonicotinoids, sulfoxoflor, carbamates, organophosphates, and organochlorines. The disclosure also demonstrates that *perilla* oil, *perilla* oil components, and certain perillaldehyde and carvone analogs can be used as synergists for insecticides in certain compositions. The disclosure further demonstrates that certain compounds having a modified cyclohexene ring containing a substituted or unsubstituted methyl group can be used as synergists for insecticides in certain compositions.

In some aspects, an insecticidal composition is provided comprising an insecticide and an active agent present in an amount of about 1% to 99% (by weight) of the composition. The active agent can be *perilla* oil, a *perilla* oil component, or a perillaldehyde or carvone analog. For example, the active agent can be selected from the group consisting of farnesene, perillaldehyde, linolenic acid, caryophyllene, limonene (including D-limonene), carvone, perillyl alcohol, pinene, linalool, germacrene, bergamotene, and spathulenol, or the active agent can be selected from the group consisting of limonene (including D-limonene), perillyl alcohol (including (S)-(−)-perillyl alcohol), perillic acid (including (S)-(−)-perillic acid), myrtenal (including (1R)-(−)-myrtenal), and 3-methyl-1-cyclohexene-1-carboxaldehyde. The active agent can also be any combination of these *perilla* oil components and perillaldehyde or carvone analogs.

In some embodiments, the active agent is a compound of Formula (I):

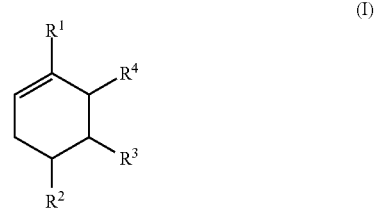

wherein:
R$^1$ is selected from the group consisting of —CH$_2$OH, —CHO, and —COOR$^a$;
R$^2$ is selected from the group consisting of hydrogen, alkyl, and alkenyl;
R$^3$ is selected from the group consisting of hydrogen and alkyl;
R$^4$ is hydrogen, or R$^4$ and R$^2$ are taken together with the atoms to which they are attached to form an optionally substituted ring; and
R$^a$ is selected from the group consisting of hydrogen and alkyl.

The insecticide in the compositions can be present at less than about 95% by weight, less than about 60% by weight or in other amounts as described is this specification and can comprise one or more of a pyrethrin, pyrethroid, neonicotinoid, chlofenapyr, ethiprole, sulfoxoflor, carbamate, organophosphate, or organochlorine. Examples of pyrethrin include one or more of jasmolin-I, cinerin-I, pyrethrin-I, jasmolin-II, cinerin-II, or pyrethrin-II. Examples of pyrethroid include one or more of etofenprox, permethrin, prallethrin, resmethrin, sumithrin, allethrin, alpha-cypermethrin, bifenthrin, beta-cypermethrin, cyfluthrin, cypermethrin, deltamethrin, esfenvalerate, etofenprox, lamdba-cyhalothrin, or zeta-cypermethrin. Examples of neonicotinoids include one or more of dinotefuran, acetamiprid, clothianidin, imidacloprid, nitenpyram, thiacloprid, or thiamethoxam. The composition can be substantially free of piperonyl butoxide, N-octyl bicycloheptene dicarboximide, or both.

In some aspects, the composition includes one or more of mineral oil, glycerol, or a diluent that provides viscosity modifying properties. The composition can be formulated to be suitable for application as an aerosol, fog, mist, spray, vapor, ultra low volume spray (ULV), surface contact treatment, or a combination thereof.

In other aspects, a method for controlling insects is provided, in which a population of insects, such as mosquitoes, is contacted with an effective amount of a composition described in this specification. The population of insects can be controlled by topically applying the composition to the population in an amount sufficient to kill at least 25%, 50%, or any proportion disclosed in this specification of the population. The composition can be applied by aerosol or as a mist, fog, vapor, spray, ULV spray, or surface contact treatment or as a combination of any of these methods.

In other aspects, a method for controlling insect pests on a plant is provided by contacting a transgenic plant with an insecticide or an active agent selected from the group consisting of (i) perilla oil; (ii) a perilla oil component selected from the group consisting of farnesene, perillaldehyde, linolenic acid, caryophyllene, limonene, carvone, perillyl alcohol, pinene, linalool, germacrene, bergamotene, and spathulenol; and (iii) a perillaldehyde or carvone analog. The transgenic plant can be modified to heterologously express an active agent, such as at least one of farnesene, perillaldehyde, linolenic acid, caryophyllene, limonene, carvone, perillyl alcohol, pinene, linalool, germacrene, bergamotene, and spathulenol, which is expressed in an amount sufficient to have a synergistic effect on insecticidal activity, or the transgenic plant can be modified to heterologously express an insecticide and contacted with the active agent in an amount sufficient to have a synergistic effect on insecticidal activity.

In other aspects, a method for controlling insect pests on a plant includes the step of contacting a transgenic plant heterologously producing an insecticide and an active agent selected from at least one of the group consisting of farnesene, perillaldehyde, linolenic acid, caryophyllene, limonene, carvone, perillyl alcohol, pinene, linalool, germacrene, bergamotene, and spathulenol with a population of insect pests. The active agent has a synergistic effect on insecticidal activity in the plant and controls the insect pests.

Other aspects of the disclosure will become apparent by consideration of the detailed description and accompanying drawings.

BRIEF DESCRIPTION OF THE DRAWINGS

FIG. 1 is a schematic representation of the experimental setup for the field study described in Example 58.

DETAILED DESCRIPTION

Figure 2:
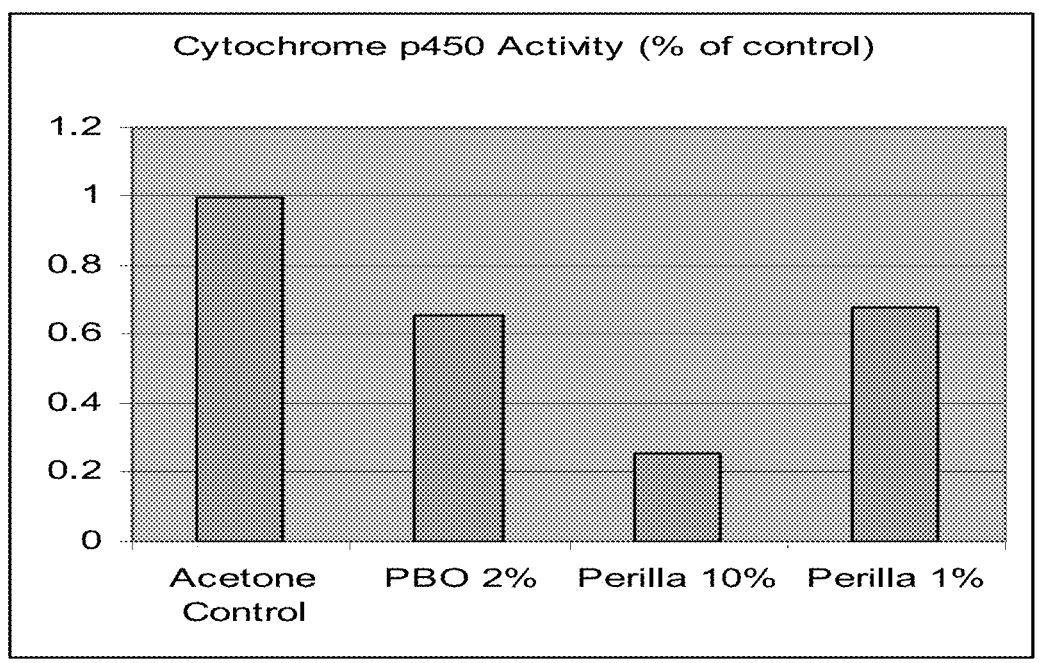
FIG. 2 is a chart showing the activity of P450 cytochrome enzyme (P450) in the presence or absence of inhibitors as described in Example 59. The control treatment contained acetone; piperonyl butoxide (PBO), a known cytochrome P450 inhibitor, was used as a positive control. The chart shows the inhibition potency of perillaldehyde (perilla) when present at 1% and 10%.

This specification broadly relates to insecticidal compositions and methods of using the same. The compositions and methods are effective and selective in killing insects. This invention describes the use of perilla oil, its components, or other related compounds to synergize the activity of non-perilla-oil-related insecticides. Accordingly, for the purposes of this specification, an insecticide refers to a compound having insecticidal activity, other than perilla oil, one of its components, a perillaldehyde analog, or the other related synergists described in this specification.

In some embodiments, an active agent comprises perilla oil, one of its components, or a perillaldehyde analog. Perilla oil, perilla oil components, and perillaldehyde analogs can be extracted from plant sources or can be synthesized. Parts of the plant used to extract these compounds include, but are not limited to, at least one of the flower, stem, leaf, seed, fruit, or fruit peel of the plant.

Plant sources may include plants of the genus Perilla, including, but not limited to, green varieties Perilla frutescens (L.) Britt. var. crispa, var. arguta, var. arcuta, var. stricta, Perilla ocymoides L. and Perilla crispa var. ocymoides—and the purple leaf varieties—Perilla frutescens var. acuta, var. typica, var. stricta, var. crisp, var. atropurpurea, var. crispa, var. nankinensis, var. olifera, var. japonica, var. citriodora, Perilla crispa (Thunb.), and Perilla nankinensis (Lour.).

Perilla oil can be extracted from a plant by any means known in the art, including, but not limited to, at least one of pressing, grinding, mashing, distillation such as steam distillation, cold pressure extraction, chromatography, a suitable solvent extraction such as liquid $CO_2$ extraction, and methanol extraction of a part or combination of parts of the plant source.

Perilla oil components and certain perillaldehyde analogs may be derived or isolated (e.g., extracted) from perilla oil or from a plant source, as described above. Perillaldehyde, a component of perilla oil, can also be extracted from other plant sources outside of the genus Perilla including, but not limited to, Sium latifolium, Citrus reticulata (e.g., the peels of the fruit), Limnophila geoffrayi, Laser tribolium, Limnophiliz aromatica, Laserpitium siler, Conyza newii, Cuminum cyminum, and Plectranthus marruboides. (R)-carvone can be extracted from perilla oil and other plant sources including artemisa fergamensis, bergamot, cassis, chamomile moroccan wild, clove oil, eucalyptus globulus, gingergrass, grapefruit, juniperberry, lavender, lemon, mandarin, marjorum, scotch spearmint (Mentha cardiaca), mentha longifolio, garden mint (Mentha spicata), common spearmint (Mentha viridis), orange, and tagetes. (S)-carvone can be extracted from perilla oil and other plant sources including Indian dill, dill, artemisa fergamensis, caraway, Eucalyptus globulus, gingergrass, lavender, Litsea guatemaleusis, and Mentha arvensis. Perillyl alcohol, also referred to as perilla alcohol, can be extracted from perilla oil and other plant sources including Amomum testaceum fruit oil, angelica root oil, bergamot plant, caraway seed oil, gingergrass, lavandin, mandarin oil, orange peel oil, perilla, rose oil otto Bulgaria, savin, turmeric root oil, and wormseed oil. (−)-Myrtenal can also be extracted from other plant sources including amomum testaceum ridl. fruit oil (Malaysia), Artemisia campestris spp., Glutoinosa flower oil (Italy), Artemisia variabilis flower oil (Italy), boldo leaf oil (Italy), chamomile oil, cistus oil, coriander seed oil (Cuba), cumin seed, cypress cone oil (Egypt), cypress oil, eucalyptus, eucalyptus globulus pseudoglobulus oil, labdanum leaf oil, labdanum oil, laurel leaf oil (Turkey), layana oil (Kenya), lemon verbena oil (Morocco), mint, nepeta betonicifolia c.a. meyer oil (Turkey), nepeta denudate benth. oil (Iran), parsley leaf oil, pepper, petitgrain sweet oil, peucedanum petriolare boiss oil (Iran), Pteronia oil, Santolina Oil, Satureja viminea l. oil (Costa Rica), Tansy oil (Morocco), wormwood oil, yarrow leaf oil, and yarrow oil. Perillic acid is also a byproduct of limonene metabolism. Limonene is a chiral molecule and is found in biological sources such as citrus fruits as D-limonene (also refered to as (+)-limonene), which is the (R)-enantiomer. Racemic limonene is known as dipentene. Perilla oil components and perillaldehyde analogs can be isolated by any means known in the art including, but not limited to, distillation such as steam distillation, cold pressure extraction, chromatography, solvent extraction such as liquid $CO_2$ extraction or methanol extraction, or a combination thereof. Perilla oil components and perillaldehyde analogs can be chemically synthesized by means known in the art. Perilla oil components and perillaldehyde analogs can be purchased from various vendors, for example, Sigma Aldrich (St. Louis, Mo.) or City Chemical (West Haven, Conn.).

In some embodiments, an active agent comprises at least one isolated or synthesized perilla oil component. Perilla oil components are known in the art and include, but are not limited to, those set forth in Table A. Perilla oil components include, but are not limited to, farnesene, perillaldehyde, linolenic acid, caryophyllene (including β-caryphyollene), limonene (including D-limonene), perillyl alcohol (including (S)-(−)-perillyl alcohol), perillic acid, carvone (including (R)-carvone and (S)-carvone), pinene (including pinene alpha and pinene beta), linalool, germacrene, bergamotene, and spathulenol.

TABLE A

| | CAS# | Melting Point | Boiling Point | Vapor Pressure (@ 25° C.) | Viscosity (@ 25° C.) | Solubility (in water @ 25° C.) |
|---|---|---|---|---|---|---|
| Pinene Alpha | 80-56-8 | (−) 62° C. | 155.5° C. | 4.75 mmHg | | 2.49 mg/L |
| Pinene Beta | 127-91-3 | (−) 61° C. | 166° C. | 2.93 mmHg | | 2.62 mg/L |
| (+)-(R)-Limonene | 5989-27-5 | (−) 40.8° C. | 178° C. | 1.541 mmHg | | 13.8 mg/L |
| Linalool | 78-70-6 | (−) 11.39° C. | 198° C. | 0.16 mmHg | 4.4 mPa | 1590 mg/L |
| Perilla Aldehyde | 2111-75-3 | (−) 4.83° C. | 218.2° C. | 0.0463 mmHg | | 160.7 mg/L |
| Perillyl Alcohol (racemic) | 536-59-4 | 11.1° C. | 244° C. | 0.00478 mmHg | | 471 mg/L |
| Caryophyllene Beta Caryophyllene Alpha | 87-44-5 | 43.4° C. | 256.8° C. | 0.031 mmHg | | 0.05 mg/L |
| Germacrene D | 23986-74-5 | 15.8° C. | 262.9° C. | 0.023 mmHg | | 0.013 mg/L |
| Bergamotene Trans Alpha | 13474-59-4 | 33.7° C. | 255.4° C. | 0.028 mmHg | | 0.030 mg/L |
| Farnesene Alpha | 502-61-4 | (−) 17.2° C. | 261.1° C. | 0.025 mmHg | | 0.011 mg/L |
| Spathulenol | 6750-60-3 | 74.9° C. | 284.6° C. | $1.2 \times 10^{-4}$ mmHg | | 12.4 mg/L |
| Caryophyllene Oxide-Beta | 1139-30-6 | 63° C. | 263.5° C. | 0.01 mmHg | | 2.21 mg/L |

In some embodiments, an active agent comprises at least one of certain perillaldehyde analogs that have a structure similar to perillaldehyde but differ from perillaldehyde by a single element or group. In particular, for the purposes of this specification, perillaldehyde analogs are limonene (including D-limonene), perillyl alcohol (including (S)-(−)-perillyl alcohol), perillic acid (including (S)-(−)-perillic acid), myrtenal (including (1R)-(−)-myrtenal), 3-methyl-1-cyclohexene-1-carboxaldehyde, and any other analog of perillaldehyde that includes substituents on the perillaldehyde cyclohexene ring that do not eliminate the ability of the analog to act as a synergist with the insecticides described in this specification.

In some embodiments, an active agent comprises a perillaldehyde analog of Formula (A):

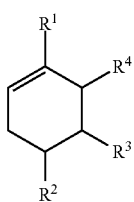

(A)

wherein:
$R^1$ is selected from the group consisting of —CH$_2$OH, —CHO, and —COOR$^a$;
$R^2$ is selected from the group consisting of hydrogen, alkyl, and alkenyl;
$R^3$ is selected from the group consisting of hydrogen and alkyl;
$R^4$ is hydrogen, or $R^4$ and $R^2$ are taken together with the atoms to which they are attached to form an optionally substituted ring; and
$R^a$ is selected from the group consisting of hydrogen and alkyl.

The term "alkyl" refers to a straight or branched saturated hydrocarbon chain. Alkyl groups may include a specified number of carbon atoms. For example, $C_1$-$C_{12}$ alkyl indicates that the alkyl group may have 1, 2, 3, 4, 5, 6, 7, 8, 9, 10, 11, or 12 carbon atoms. An alkyl group may be, e.g., a $C_1$-$C_{12}$ alkyl group, a $C_1$-$C_{10}$ alkyl group, a $C_1$-$C_8$ alkyl group, a $C_1$-$C_6$ alkyl group, or a $C_1$-$C_4$ alkyl group. For example, exemplary $C_1$-$C_4$ alkyl groups include methyl, ethyl, n-propyl, isopropyl, n-butyl, sec-butyl, isobutyl and tert-butyl groups. An alkyl group may be optionally substituted with one or more substituents.

The term "alkenyl" refers to a straight or branched hydrocarbon chain having one or more double bonds. Alkenyl groups may include a specified number of carbon atoms. For example, $C_2$-$C_{12}$ alkenyl indicates that the alkenyl group may have 2, 3, 4, 5, 6, 7, 8, 9, 10, 11, or 12 carbon atoms. An alkenyl group may be, e.g., a $C_2$-$C_{12}$ alkenyl group, a $C_2$-$C_{10}$ alkenyl group, a $C_2$-$C_8$ alkenyl group, a $C_2$-$C_6$ alkenyl group, or a $C_2$-$C_4$ alkenyl group. Examples of alkenyl groups include but are not limited to allyl, propenyl, 2-butenyl, 3-hexenyl, and 3-octenyl groups. One of the double bond carbons may optionally be the point of attachment of the alkenyl substituent. An alkenyl group may be optionally substituted with one or more substituents.

Substituents may include hydroxy, alkoxy (e.g., methoxy, ethoxy, propoxy, butoxy, and pentoxy), aryloxy groups (e.g., phenoxy, chlorophenoxy, tolyloxy, methoxyphenoxy, benzyloxy, alkyloxycarbonylphenoxy, and acyloxyphenoxy), acyloxy groups (e.g., propionyloxy, benzoyloxy, and acetoxy), carbamoyloxy groups, carboxy groups, mercapto groups, alkylthio groups, acylthio groups, arylthio groups (e.g., phenylthio, chlorophenylthio, alkylphenylthio, alkoxyphenylthio, benzylthio, and alkyloxycarbonylphenylthio), halogen atoms, cyano groups, monovalent hydrocarbon groups, substituted monovalent hydrocarbon groups, heterogeneous groups, aromatic groups (e.g., phenyl and tolyl), substituted aromatic groups (e.g., alkoxphenyl, alkoxycarbonylphenyl, and halophenyl), heterocyclic groups, heteroaromatic groups, and amino groups (e.g., amino, mono- and di-alkylamino having 1 to 3 carbon atoms, methylphenylamino, methylbenzylamino, alkanylamido groups of 1 to 3 carbon atoms, carbamamido, ureido, and guanidino), or any combination thereof.

In some embodiments, an active agent comprises at least one of certain carvone analogs that have a structure similar to carvone. These analogs retain at least some of the activity of carvone. It is known in the art that structural modifications can be made to carvone so as to affect the physical properties of carvone, such as to reduce its volatility. See, e.g., Olof Smitt, Thesis entitled Syntheses of Allelochemicals for Insect Control (2002), Mid Sweden University, ISSN 1100-7974, ISBN 91-7283-277-0, the entire disclosure of which is incorporated into this specification by reference. Indeed, the modifications made to the structure of carvone can in some cases enhance the biological activity of the analog in the composition as compared to carvone. Carvone analogs are shown below in Formulas B-K and include epoxycarvone, hydroxydihydrocarvone, and carvone diols.

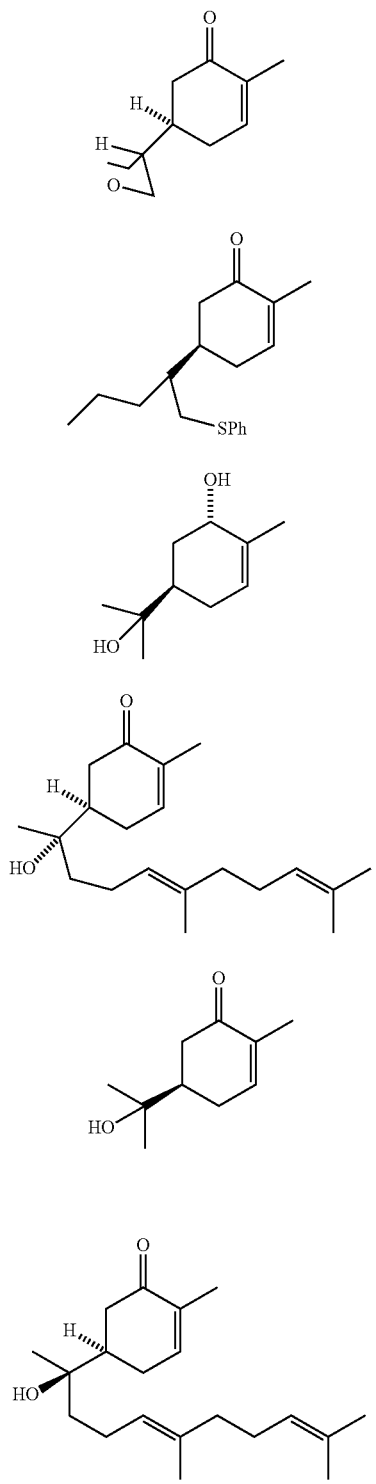

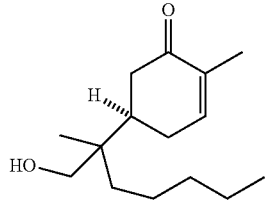

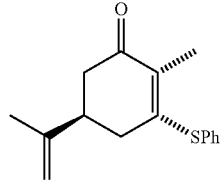

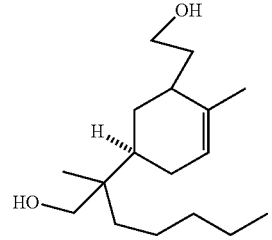

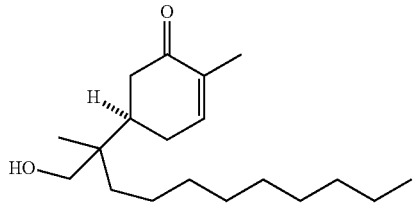

In some embodiments, an active agent comprises a synergist which has a modified cyclohexene ring containing a substituted or unsubstituted methyl group and other substituents on the ring. Examples of synergists having such a modified cyclohexene ring include, but are not limited to, isophorone, 1-methyl-1-cyclohexene, 1-tert-butyl-1-cyclohexene, 3,5-dimethyl-2-cyclohexen-1-one, 4-methycyclohexene, 7,8-dihydro-α-ionone, 2,4-dimethyl-3-cyclohexenecarboxaldehyde, trivertal, 3-cyclohexene-1-methanol, and terpinolene.

In some embodiments, the insecticide includes, but is not limited to, pyrethrum, pyrethrins, pyrethroids, spinosad, neonicotinoids, sulfoxoflor, carbamates, organophosphates, and organochlorines.

The insecticide can be present in an amount of at least about 0.005%, at least about 0.01%, at least about 0.05%, at least about 0.1%, at least about 0.5%, at least about 1%, at least about 2%, or at least about 3%, at least about 4%, at least about 6%, at least about 8%, at least about 10%, at least about 12%, at least about 15%, at least about 20%, at least about 25%, at least about 30%, at least about 35%, at least about 40%, at least about 50% or at least about 55%, at least about 60%, at least about 65%, at least about 70%, at least about 75%, at least about 80%, at least about 85%, at least about 90%, at least about 95%, and less than about 95%, less than about 90%, less than about 80%, less than about 75%, less than about 70%, less than about 65%, less than about 60%, less than about 55%, less than about 50%, less than about 45%, less than about 35%, less than about 30%, less than about 25%, less than about 20%, less than about 15%, less than about 10%, less than about 5%, less than about 2.5%, less than about 2%, less than about 1%, less than about 0.5%, or less than about 0.1% by weight of the composition.

In some embodiments, the composition comprises an insecticide and active agent as described in this specification, and is substantially free of, or excludes any amount of, any other insecticide synergist such as piperonyl butoxide (PBO), N-octyl bicycloheptene dicarboximide (MGK-264), piprotal, propyl isome, sesamex, sesamolin, or sulfoxide. The composition may be substantially free of, or exclude any amount of, one or more of piperonyl butoxide (PBO), N-octyl bicycloheptene dicarboximide (MGK-264), piprotal, propyl isome, sesamex, sesamolin, or sulfoxide in any combination.

As used in this specification, the term "pyrethrum" refers to a crude extract composition that is derived from chrysanthemum-like flowers primarily grown in Kenya, Tanzania, and Australia (e.g., *T. cinerariaefolium, C. cinerariaefolium*, and *C. coccineum*) and comprises a mixture of the naturally occurring insecticidal ester compounds known as the "pyrethrins," as further detailed in U.S. patent application Ser. No. 13/175,405, filed Jul. 1, 2011, which is incorporated into this specification by reference in its entirety. "Pyrethrins" is used in this specification as a collective term given to any combination of the six ester compounds (including refined pyrethrum) having the general Formula L and detailed in Table 1.

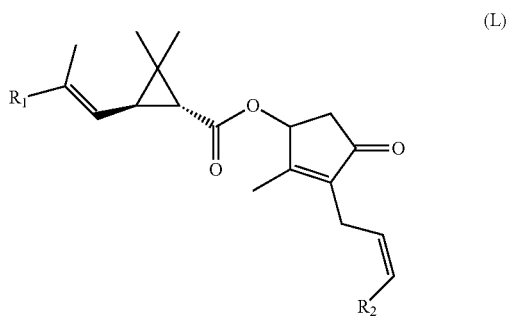

(L)

TABLE 1

Naturally Occurring Pyrethrin Esters.

| Common Name | CAS Number | $R_1$ | $R_2$ |
|---|---|---|---|
| Pyrethrins I | | | |
| Jasmolin-I | 4466-14-2 | $CH_3$ | $CH_2CH_3$ |
| Cinerin-I | 25402-06-6 | $CH_3$ | $CH_3$ |
| Pyrethrin-I | 121-21-1 | $CH_3$ | $CH=CH_2$ |
| Pyrethrins II | | | |
| Jasmolin-II | 1172-63-0 | $CH_3OC(O)$ | $CH_2CH_3$ |
| Cinerin-II | 121-20-0 | $CH_3OC(O)$ | $CH_3$ |
| Pyrethrin-II | 121-29-9 | $CH_3OC(O)$ | $CH=CH_2$ |

The term "pyrethrin ester" or "pyrethrin" is used in this specification to refer to one or a combination of two or more of the naturally occurring compounds defined in Table 1.

While the terms "pyrethrins" and "pyrethrum" are sometimes used interchangeably, "pyrethrum" should be understood here to encompass crude extracts that contain pyrethrins. The pyrethrins in any given pyrethrum extract vary in relative amount, depending on factors such as the plant variety, where it is grown, and the time of harvest.

Because it is not currently commercially advantageous to separate and isolate individual pyrethrin esters from each other, the pyrethrins content in pyrethrum extract is typically analyzed for total content of pyrethrins. While variable, the current state of the art typically allows for the total pyrethrins (i.e., pyrethrins I and pyrethrins II) to constitute about 45 to 55% (by weight) of a pyrethrum extract. Besides the pesticidally active esters mentioned above, many plant components may be present in the pyrethrum extract. This extract is typically a high boiling, viscous liquid that is prone to oxidation in air, might be difficult to store for extended periods of time, and can be readily diluted in a vegetable-based oil carrier to provide a Manufacturing Use Product (MUP) containing about 20% pyrethrins. This provides for a longer shelf life and has the added advantage of being NOSB (National Organic Standards Board) compliant. Therefore, pyrethrins are approved for use in organic production operations. Pyrethrins are commercially available from several sources throughout the world and, in the United States, are available from several sources including the product sold under the trade name Pyganic® MUP 20 by MGK (Minneapolis, Minn.). Pyganic® MUP 20 contains about 20% pyrethrins by weight. When the term "MUP 20" is used in this specification it refers to a MUP comprising about 20% pyrethrins by weight and includes, but is not limited to, Pyganic® MUP 20.

The term "pyrethroid" is understood in the art to mean one or more synthetic compounds that act as an insecticide and are adapted from the chemical structure of Formula L. The United States Environmental Protection Agency (EPA) has established two general classes of pyrethroids. Pyrethroids that include an α-cyano group (C—CN) bonded to the ester oxygen (see Formula L) are referred to as Type II pyrethroids, while pyrethroids lacking an α-cyano group are referred to as Type I pyrethroids. See, e.g., EPA Office of Pesticide Programs Memorandum "Pyrethroids: Evaluation of Data from Developmental Neurotoxicity Studies and Consideration of Comparison Sensitivity" (Jan. 20, 2010). Non-limiting examples of pyrethroids include acrinathrin, allethrin, benfluthrin, benzylnorthrin, bioallethrin, bioethanomethrin, bioresmethrin, bifenthrin, cyclethin, cycloprothrin, cyfluthrin, beta-cyfluthrin, gamma-cyhalothrin, lamdba-cyhalothrin, cypermethrin, alpha-cypermethrin, beta-cypermethrin, zeta-cypermethrin, cyphenothrin, deltamethrin, empenthrin, esbiothrin, esfenvalerate, etofenprox, fenfluthrin, fenpropathrin, fenvalerate, flucythrinate, flumethrin, imiprothin, isopyrethrin I, kadethrin, metoflathrin, permethrin, 1RS cis-permethrin, phenothrin, prallethrin, resmethrin, silafluofen, sumithrin (d-phenothrin), tau-fluvalinate, tefluthrin, tetramethrin, tralomethrin, transfluthrin, and isomers of these compounds. Etofenprox, a recently registered pyrethroid, contains an ether bond as its central linkage rather than an ester bond. In certain embodiments, the pyrethroid comprises at least one of permethrin, sumithrin, prallethrin, resmethrin, etofenprox, allethrin, alpha-cypermethrin, bifenthrin beta-cypermethrin, cyfluthrin, cypermethrin, deltamethrin, esfenvalerate, etofenprox, lamdba-cyhalothrin, and zeta-cypermethrin, which may be used with, for example, *perilla* oil, perillaldehyde or carvone.

Additional information regarding pyrethrum, pyrethrins, and pyrethroids can be found in various references, reviews, and fact sheets, for example, Pyrethrum Flowers: Production, Chemistry, Toxicology, and Uses. John E. Casida and Gary B. Quistad (eds.), Oxford University Press, 1995; and "Pyrethrins & Pyrethroids" 1998 Fact Sheet published by the National Pesticide Telecommunications Network (NPTN) at Oregon State University, Corvallis, Oreg.

Spinosad is an insecticide derived from *Saccharopolyspora spinosa. S. spinosa* occurs in over 20 natural forms, and over 200 synthetic forms (spinosoids). As used in this specification, spinosad includes at least one of Spinosyn A, Spinosyn D, or a combination thereof.

Neonicotinoids are insecticides that act on the central nervous system of insects. Neonicotinoids include, but are not limited to, acetamiprid, clothianidin, dinotefuran, imidacloprid, nitenpyram, thiacloprid, and thiamethoxam.

Carbamates are organic compounds derived from carbamic acid ($NH_2COOH$) and feature the carbamate ester functional group. Carbamates include, but are not limited to, aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, and triazamate.

Organophosphates are esters of phosphoric acid which act on the enzyme acetylcholinesterase. Organophosphates include, but are not limited to, acephate, azamethiphos, azinphos-ethyl, azinphos-methyl, chlorethoxyfos, chlorfenvinphos, chlormephos, chlorpyrifos, methyl chlorpyrifos, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, omethoate, oxydemeton-methyl, parathion, methyl parathion, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, and vamidothion.

Organochlorines are organic compounds containing at least one covalently bonded chlorine atom. Organochlorines include, but are not limited to, phthalimides, sulfamides, and chloronitriles, including, but not limited to, anilazine, captan, chlorothalonil, captafol, chlordane, dichlorodiphenyltrichloroethane (DDT), dicofol, dichlofluanid, dichlorophen, endosulfan, flusulfamide, folpet, hexachlorobenzene, heptachlor, pentachlorphenol and its salts, aldrin, dieldrin, endrin, mirex, phthalide, and tolylfluanid, N-(4-chloro-2-nitro-phenyl)-N-ethyl-4-methyl-benzenesulfonamide.

Compositions

Compositions described in this specification may comprise at least one active agent synergist and at least one insecticide. The active agent may consist of at least one of *perilla* oil, one of its components, a perillaldehyde or carvone analog, or other related synergist described in this specification and can be present in an amount of at least about 0.01%, at least about 0.1%, at least about 0.5%, at least about 1%, at least about 2%, or at least about 3%, at least about 4%, at least about 6%, or at least about 8%, at least about 10%, at least about 15%, at least about 20%, at least about 25%, and less than about 99.99%, less than about 99.9%, less than about 99%, less than about 95%, less than about 90%, less than about 80%, less than about 70%, less than about 60%, less than about 50%, less than about 40%, less than about 30%, less than about 25%, less than about 20%, less than about 15%, less than about 14%, less than about 12%, or less than about 10% by weight of the composition. The compositions may comprise at least one of *perilla* oil, one of its components, a perillaldehyde or carvone analog, or other synergist described in this specification and may be present in an amount of about 1% to about 15%, about 2% to about 14%, about 6% to about 12%, or about 8% to about 10% by weight of the composition. Compositions may comprise an active agent that consists of at least one of *perilla* oil, one of its components, a perillaldehyde or carvone analog, or other synergist described in this specification in an amount of less than about 100%, less than about 99%, less than about 98%, less than about 97%, less than about 96%, or less than about 95% by weight of the composition. The compositions may comprise an active agent that consists of *perilla* oil, one of its components, a perillaldehyde or carvone analog, or other synergist described in this specification in an amount of about 1% to about 100%, about 1% to about 99%, about 2% to about 99%, or about 3% to about 98% by weight of the composition.

For example, in some embodiments, compositions may comprise up to about 100% *perilla* oil. In some embodiments, compositions may comprise 15% perillaldehyde. In some embodiments, compositions may comprise 2% perillaldehyde analog. In some embodiments, compositions may comprise 30% perillaldehyde and 30% permethrin.

In addition to a first active agent that consists of *perilla* oil or one of its components or a perillaldehyde or carvone analog or other synergist described in this specification in an amount described above, and depending on the amount of the first active agent, compositions may comprise a second active agent, such as a different *perilla* oil component, perillaldehyde or carvone analog, or synergist in the amounts described in the preceding paragraph.

In some embodiments, compositions may comprise at least one insecticide selected from the group consisting of pyrethrum, pyrethrins, pyrethroids, spinosad, neonicotinoids, sulfoxoflor, carbamates, organophosphates, and organochlorines. The insecticide can be present in an amount of at least about 1%, at least about 2%, at least about 4%, at least about 6%, or at least about 8%, less than about 15%, less than about 14%, less than about 12%, or less than about 10% by weight of the composition. The compositions may comprise an insecticide in an amount of about 1% to about 15%, about 2% to about 14%, about 6% to about 12%, or about 8% to about 10% by weight of the composition.

In addition to a first active agent that consists of *perilla* oil or one of its components or a perillaldehyde or carvone analog or other synergist described in this specification in an amount described above, at least one insecticide, such as at least one selected from the group consisting of pyrethrum, pyrethrins, pyrethroids, spinosad, neonicotinoids, sulfoxoflor carbamates, organophosphates, and organochlorines in an amount described above, and an optional second active agent comprising a different *perilla* oil component, depending on the amount of the first and second active agents, compositions may comprise a third active agent consisting of a different *perilla* oil component or a different insecticide selected from the group consisting of pyrethrum, pyrethrins, pyrethroids, spinosad, neonicotinoids, sulfoxoflor, carbamates, organophosphates, and organochlorines in an amount of at least about 1%, at least about 2%, at least about 4%, at least about 6%, or at least about 8%, less than about 15%, less than about 14%, less than about 12%, less than about 10% by weight of the composition. The compositions may comprise a third active agent in an amount of at least about 1%, at least about 2%, at least about 3%, at least about 4%, at least about 5%, at least about 6%, at least about 7%, at least about 8%, at least about 9%, or at least about 10%, and less than about 99.9%, less than about 99%, less than about 95%, less than about 75%, less than about 50%, less than about 40%, less than about 35%, less than about 25%, less than about 20%, less than about 15%, less than about 14%, less than about 12%, or less than about 10% by weight of the composition. The compositions may comprise a third active agent that consists of *perilla* oil or one of its components in an amount of about 1% to about 100%, about 1% to about 99%, about 2% to about 99%, or about 3% to about 98% by weight of the composition.

Compositions may further comprise a viscosity modifier such as one or more of mineral oil or glycerol. "Mineral oil" as used in this specification relates to the commonly known product of the same name, which is a by-product of the distillation of petroleum (crude oil) to make gasoline and other products. Mineral oil is typically transparent and colorless and comprises complex mixtures of long chain aliphatic compounds often ranging in size from $C_{15}$-$C_{40}$. Depending on the refining process and source of crude oil, mineral oils can also include paraffinic, naphthenic, and aromatic compounds in varying weight percentages. Synonymous names for mineral oil can include "paraffin oil" or "white mineral oil" among other common names. Mineral oil is available from any number of commercial distributors (e.g., Brenntag, ProChem, Inc.). Non-limiting examples of "mineral oil" include those identified by CAS registry numbers: 8012-95-1, 8020-83-5, 8042-47-5, 72623-84-8, 72623-86-0, 72623-87-1, 64741-88-4, 64741-89-5, 64742-54-7, 64742-55-8, 64742-56-9, and 64742-65-0. The compositions may comprise a viscosity modifier, such as mineral oil glycerol, or any combination of viscosity modifiers, in an amount of at least about 10%, at least about 15%, at least about 20%, at least about 25%, at least about 30%, at least about 35%, at least about 40%, at least about 45%, at least about 50%, at least about 55%, at least about 60%, at least about 65%, or at least about 70% by weight of the composition. The compositions may comprise a viscosity modifier, such as mineral oil, glycerol, or any combination of viscosity modifiers, in an amount of less than about 99%, less than about 95%, less than about 90%, less than about 85%, or less than about 80% by weight of the composition. The compositions may comprise a viscosity modifier, such as mineral oil, glycerol, or a combination of viscosity modifiers, in an amount of about 10% to about 99%, about 15% to about 99%, about 20% to about 99%, about 25% to about 99%, about 30% to about 99%, about 35% to about 99%, about 40% to about 99%, about 45% to about 99%, about 50% to about 99%, about 55% to about 99%, about 60% to about 99%, about 65% to about 99%, about 70% to about 99%, about 70% to about 95%, about 70% to about 90%, about 60% to about 90%, about 50% to about 90%, about 40% to about 90%, about 30% to about 90%, about 20% to about 90%, about 10% to about 90%, about 70% to about 85%, or about 70% to about 80% by weight of the composition.

In some embodiments, a composition can include one or more carriers and/or diluents such as, for example, any solid or liquid carrier or diluent that is commonly used in pesticidal, agricultural, or horticultural compositions. Suitably, any included additional carrier or diluent will not reduce the insecticidal efficacy of the composition, relative to the efficacy of the composition in the absence of the additional component. Carriers and diluents can include, for example, solvents (e.g., water, alcohols, petroleum distillates, acids, and esters); vegetable (including, but not limited to, methylated vegetable) and/or plant-based oils as well as ester derivatives thereof (e.g., wintergreen oil, cedarwood oil, rosemary oil, peppermint oil, geraniol, rose oil, palmarosa oil, citronella oil, citrus oils (e.g., lemon, lime, and orange), dillweed oil, corn oil, sesame oil, soybean oil, palm oil, vegetable oil, olive oil, peanut oil, and canola oil). The composition can include varying amounts of other components such as, for example, surfactants (e.g., non-ionic, anionic, cationic, and zwitterionic surfactants); fatty acids and fatty acid esters of plant oils (e.g., methyl palmitate/oleate/linoleate); and other auxiliary ingredients such as, for example, emulsifiers, dispersants, stabilizers, suspending agents, penetrants, coloring agents/dyes, UV-absorbing agents, and fragrances, as necessary or desired. The compositions may comprise carrier or diluent in an amount of at least about 5% or at least about 10% by weight of the composition. The compositions may comprise carrier or diluent in an amount of less than about 90% or less than about 80% by weight of the composition. The compositions may comprise carrier or diluent in an amount of about 5% to about 90%, or about 10% to about 80% by weight of the composition. Components other than active agent(s) can be included in the compositions in any amount as long as the composition has some amount of insecticidal efficacy.

Components of a composition can have a synergistic or additive effect on insecticidal activity. Components have an additive effect when the effect of the combination is equal to the sum of the effects of each individual component. In contrast, components have a synergistic effect when the effect of the combination exceeds the sum of the effects of the components when applied individually. The effect (E) of a combination of two compounds may be calculated using the Colby formula (1) (S. R. Colby, "Calculating Synergistic and Antagonistic Responses of Herbicide Combinations", *Weeds* 1967, 15, 20-22):

$$E = X + Y - \frac{X \times Y}{100} \quad (1)$$

wherein X is the kill rate, expressed as a percentage of the untreated control, when employing active compound X' at an application rate of m g/ha or in a concentration of m ppm, μg, or other appropriate unit;

wherein Y is the kill rate, expressed as a percentage of the untreated control, when employing active compound Y' at an application rate of n g/ha or in a concentration of n ppm, μg, or other appropriate unit;

wherein E is the kill rate, expressed as a percentage of the untreated control, when employing active compounds X' and Y' at application rates of m and n g/ha or in a concentration of m and n ppm. If the actual insecticidal kill rate is the calculated value (E), then the action of the combination is additive. If the actual insecticidal kill rate exceeds the calculated value (E), then the action of the combination is super-additive, that is, a synergistic effect is present. If the insecticidal kill rate is lower than the calculated value (E), then the action of the combination is considered antagonistic.

As shown in the Examples, *perilla* oil and some of its components, a perillaldehyde or carvone analog, or other synergist can have synergistic activity with insecticides such as pyrethrum, pyrethrins, pyrethroids, spinosad, neonicotinoids, sulfoxoflor, carbamates, organophosphates, and organochlorines. The nature of the synergistic activity is unknown; however, without being limited to theory, it is postulated that *perilla* oil, its components or a perillaldehyde or carvone analog or other related synergist may be preventing the degradation of insecticides by blocking detoxifying enzymes such as the oxidases (P450's), esterases (COE's), and transferases (GST's), all of which have been implicated in rendering exogenous toxins such as insecticides inactive.

As an example, compositions may comprise a *perilla* oil component, such as carvone, or a perillaldehyde or carvone analog, and an insecticide, such as a neonicotinoid, wherein the *perilla* oil component or perillaldehyde or carvone analog acts as a synergist to increase the efficacy or activity of the insecticide. The *perilla* oil component may be present in the composition with the insecticide.

Embodiments include commercially useful formulations or "ready-to-use" application forms. In such formulations, the composition can be suitably provided as a mixture with other active compounds, for example, various additional insecticides, pesticides, fungicides, anti-microbials, and/or herbicides, as well as plant growth regulators, insect repellents, attractants, fertilizers, and/or fragrances, to expand the applicability of the insecticidal composition described in this specification. Embodiments provide for the compositions manufactured as formulations that are useful for insect control. In some embodiments, the composition can be formulated as an emulsion, a liquid concentrate, a sol (flowable agent), an aerosol (e.g., fogger), a liquid for ultra low volume (ULV) application, a mist, a spray, a vapor, a surface contact treatment, or incorporated into fibers or other materials such as a bednet, or the like, by any standard or conventional methods for mixing and manufacturing such formulations such as, for example, admixing active agent and an amount of mineral oil, glycerol, other viscosity modifier, or combination thereof, and optionally with one or more of any suitable additional inert ingredient that is used as a carrier, solvent, diluent, emulsifier, dispersant, stabilizers, suspending agent, or penetrant. The addition of these materials would depend on the active ingredient and the type of formulation and how it is intended to be applied. Compositions suitable for a particular application type can be formulated by those of skill in the art based on standard and conventional methods using guidance provided in this specification.

In some embodiments, the composition can be formulated for application or delivery as an aerosol or a fog wherein the composition allows for the formation of droplets having an average diameter of about 1 μm to about 30 μm. Suitable compositions for such a formulation typically should have a viscosity that allows for the composition to atomize, but not be so thick as to clog the nozzle. Such viscosities can vary and be readily determined by one of skill in the art; however, a non-limiting common minimum viscosity is about 70 centistokes (cts).

Plants or plant cells that have been modified to produce a *perilla* oil component, perillaldehyde or carvone analog, or synergist described in this specification are also provided. In certain embodiments, the plants or plant cells are modified to contain or express polynucleotides and/or polypeptides that facilitate the synthesis of, or increase the synthesis of, a *perilla* oil component or perillaldehyde analog or synergist in the plant. In certain embodiments, the plants are further modified to produce a pesticide in the plant, in addition to a *perilla* oil component, perillaldehyde analog, or combination thereof. In certain embodiments, the modified plants exhibit enhanced or increased resistance to insect or pest attack when compared with control plants or plant cells. In certain embodiments, the modified plants or plant cells exhibit enhanced growth, yield or a combination thereof relative to control plants. Modified plants may include vegetable, herb, spice, or fruit crops, as well as plants or crops producing cotton, flax, tobacco, hemp, rubber, nuts, and nursery stock and ornamental plant parts. Modified plants may include crops such as soybeans, corn, canola, oilseed rape, cotton, sugar beet, alfalfa, peanuts, wheat, barley, rye, oats, millet, and rice.

Transgenic plants and methods of producing transgenic plants are provided. Such transgenic plants are produced, in certain embodiments, by introducing into a plant or plant cell one or more polynucleotides encoding one or more polypeptides that are involved in the synthesis of a *perilla* oil component or perillaldehyde analog, such that the polynucleotide is heterologously expressed and the *perilla* oil component or perillaldehyde analog is produced. In certain embodiments, expression of such polynucleotides or polypeptides may be down regulated, for example, by antisense, RNAi, micro RNAs, or sense suppression. In certain embodiments, the polynucleotide is provided as a construct in which a promoter is operably linked to the polynucleotide. The synthesis pathways and enzymes responsible for producing many *perilla* oil components and perillaldehyde analogs are known to those of skill in the art. For example, the isoprenyl synthesis pathway is well understood. Polypeptide enzymes that may be modified include, but are not limited to, monoterpene synthase, limonene-6-hydroxylase, (+)-trans-carveol dehydrogenase, mevalonate kinases, acetoacetyl-CoA thiolase, 3-hydroxy 3-methylgluteryl-CoA transferase, prenyl transferases, terpene synthases, transketolases. One of skill in the art would understand how to manipulate de novo, enhanced or reduced expression and activity of such polypeptides, such that production of a *perilla* oil component or perillaldehyde analog is effected, increased or decreased in the plant. Accordingly, the transgenic plant can be modified to express one or more of farnesene, perillaldehyde, linolenic acid, caryophyllene, limonene, carvone, perillyl alcohol, pinene, linalool, germacrene, bergamotene, and spathulenol wherein the active agent has a synergistic effect on insecticidal activity. In certain embodiments, methods for controlling insect pests on a transgenic plant are provided in which a transgenic plant expressing a *perilla* oil component or perillaldehyde analog is contacted with an insecticide using one or more methods of application described in this specification for the compositions of the invention. The *perilla* oil component or perillaldehyde analog is expressed in the plant in an amount effective to have a synergistic effect on the insecticide.

As used in this specification, a "control plant" is a plant that is substantially equivalent to a test plant or modified plant in all parameters with the exception of the test parameters. For example, when referring to a plant into which a polynucleotide encoding a polypeptide involved in the synthesis of a *perilla* oil component or perillaldehyde analog, in certain embodiments, a control plant is an equivalent plant into which either no such polynucleotide has been introduced. In certain embodiments, a control plant is an equivalent plant into which a control polynucleotide has been introduced. In such instances, the control polynucleotide is one that is expected to result in little or no phenotypic effect on the plant.

The polynucleotides encoding polypeptides involved in the synthesis of a *perilla* oil component or perillaldehyde analog may be introduced into a plant cell to produce a transgenic plant. As used in this specification, "introduced into a plant" with respect to polynucleotides encompasses the delivery of a polynucleotide into a plant, plant tissue, or plant cell using any suitable polynucleotide delivery method. Methods suitable for introducing polynucleotides into a plant useful in the practice of the present invention include, but are not limited to, freeze-thaw method, microparticle bombardment, direct DNA uptake, whisker-mediated transformation, electroporation, sonication, microinjection, plant virus-mediated, and *Agrobacterium*-mediated transfer to the plant. Any suitable *Agrobacterium* strain, vector, or vector system for transforming the plant may be employed according to the present invention.

In some embodiments, a plant may be regenerated or grown from the plant, plant tissue or plant cell. Any suitable methods for regenerating or growing a plant from a plant cell or plant tissue can be used, such as, without limitation, tissue culture or regeneration from protoplasts. Plants may be regenerated by growing transformed plant cells on callus induction media, shoot induction media and/or root induction media.

The polynucleotides to be introduced into the plant can be operably linked to a promoter sequence and can be provided as a construct. As used in this specification, a polynucleotide is "operably linked" when it is placed into a functional relationship with a second polynucleotide sequence. For instance, a promoter is operably linked to a coding sequence if the promoter is connected to the coding sequence such that it may effect transcription of the coding sequence. In various embodiments, the polynucleotides may be operably linked to at least one, at least two, at least three, at least four, at least five, or at least ten promoters.

Promoters useful in the practice of the present invention include, but are not limited to, constitutive, inducible, temporally-regulated, developmentally regulated, chemically regulated, tissue-preferred and tissue-specific promoters. Suitably, the promoter causes sufficient expression in the plant to produce the phenotypes described in this specification. Suitable promoters include, but are not limited to, the 35S promoter of the cauliflower mosaic virus, ubiquitine, tCUP cryptic constitutive promoter, the Rsyn7 promoter, pathogen-inducible promoters, the maize In2-2 promoter, the tobacco PR-1a promoter, glucocorticoid-inducible promoters, and tetracycline-inducible and tetracycline-repressible promoters.

The modified plant producing the *perilla* oil component or perillaldehyde analog component may have a composition comprising an insecticide, as described in this specification, applied such that the insecticide contacts the plant. Upon application of the insecticide, the *perilla* oil component is expressed or produced by the plant in an amount effective to act as a synergist to increase the efficacy or activity of the insecticide against an insect pest, such as those described in this specification. In plants modified to produce a pesticide and a *perilla* oil component or perillaldehyde, enhanced resistance to insect pests described in this specification may be achieved without application of a pesticide.

Methods for Making Compositions

The compositions can be generally prepared by any appropriate manufacturing processes and using any appropriate manufacturing equipment such as is known in the art. Suitably, the compositions can be prepared by combining the various components in an appropriate vessel (considering vessel size, amount of composition to be made and reactivity of components) with mixing (e.g., stirring) until a uniform or homogeneous composition is achieved. The various composition components can be added sequentially, with stirring between each addition to ensure dissolution and/or dispersion of the previous component. This may be followed by addition of one or more additional components (e.g., solvents, diluents, and carriers) with stirring to provide a homogeneous composition.

Methods

In some aspects, the disclosure provides methods for insect control comprising contacting an insect with an amount of any of the compositions described in this specification. As used in this specification, insects may include, but are not limited to, mosquitoes. "Mosquito" is understood to refer to any species of the approximately 3,500 species of the insect that is commonly associated with and given the common name, "mosquito." Mosquitoes span 41 insect genera, including the non-limiting examples of *Aedes, Culex, Anopheles* (carrier of malaria), *Coquillettidia*, and *Ochlerotatus*. In embodiments described in this specification, a mosquito can refer to an adult mosquito or a larval mosquito or both. Thus, some embodiments describe methods or compositions wherein the insecticidal activity is referred to as mosquito "adulticide" or alternatively a mosquito "larvacide." Insects may further include agronomic pests including, but not limited to, insects of the orders Lepidoptera (moths), Coleoptera (beetles), and Hemiptera (sucking insects, true bugs). Contacting an insect with a composition includes, but is not limited to, exposing an insect or a population of insects either by direct contact using any method described in this specification or known in the art, such as by topical application, or by indirect contact such as by inhalation of a vapor, spray, mist, aerosol or fog or by ingestion of the composition by the insect.

*Perilla* oil, the *perilla* oil components, the perillaldehyde and carvone analogs, and the synergists having a cyclohexene ring described in this specification also have a synergistic effect with insecticides, such as pyrethrum, pyrethrins, pyrethroids, neonicotinoids, carbamates, organophosphates and organochlorines when used to control agronomonic pests. Agronomic pests include larvae of the order Lepidoptera, such as armyworms, (e.g., beet armyworm (*Spodoptera exigua*)), cutworms, loopers, (e.g., cabbage looper (*Trichoplusia ni*)) and heliothines in the family Noctuidae (e.g., fall armyworm (*Spodoptera fugiperda* J. E. Smith), beet armyworm (*Spodoptera exigua* Hubner), black cutworm (*Agrotis ipsilon* Hufnagel), and tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hubner), navel orangeworm (*Amyelois transitella* Walker), corn root webworm (*Crambus caliginosellus* Clemens), and sod webworms (Pyralidae: Crambinae) such as sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), and oriental fruit moth (*Grapholita molesta* Busck)); and many other economically important Lepidoptera (e.g., diamondback moth (*Plutella xylostella* Linnaeus), pink bollworm (*Pectinophora gossypiella* Saunders), silverleaf whitefly (*Bemisia argentifolii*), and gypsy moth (*Lymantria dispar* Linnaeus)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus), annual bluegrass weevil (*Listronotus maculicollis* Dietz), bluegrass billbug (*Sphenophorus parvulus* Gyllenhal), hunting billbug (*Sphenophorus venatus* vestitus), and Denver billbug (*Sphenophorus cicatristriatus* Fahraeus)); flea beetles, cucumber beetles, rootworms, leaf beetles, potato beetles, and leafminers in the family Chrysomelidae (e.g., Colorado potato beetle (*Leptinotarsa decemlineata* Say)); western corn rootworm (*Diabrotica virgifera virgifera* LeConte); western flower thrip (*Frankliniella occidentalis*)); chafers and other beetles from the family Scaribaeidae (e.g., Japanese beetle (*Popillia japonica* Newman), oriental beetle (*Anomala orientalis* Waterhouse), northern masked chafer (*Cyclocephala borealis* Arrow), southern masked chafer (*Cyclocephala immaculate* Olivier), black turfgrass *ataenius* (*Ataenius spretulus* Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae; flour beetles from the family Tenebrionidae; leafhoppers (e.g.,

*Empoasca* spp.) from the family Cicadellidae; planthoppers from the families Fulgoroidae and Delphacidae (e.g., corn plant hopper (Peregrinus maidis)); treehoppers from the family Membracidae; psyllids from the family Psyllidae; whiteflies from the family Aleyrodidae; aphids from the family Aphididae, such as *Aphis gossypii* (cotton melon aphid), *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), *Toxoptera citricida* Kirkaldy (brown citrus aphid) and green peach aphid (*Myzus persicae*); phylloxera from the family Phylloxeridae; mealybugs from the family Pseudococcidae; scales from the families Coccidae, Diaspididae, and Margarodidae; lace bugs from the family Tingidae; stink bugs from the family Pentatomidae; flat mites in the family Tenuipalpidae (e.g., citrus flat mite (*Brevipalpus lewisi* McGregor)); rust and bud mites in the family Eriophyidae and other foliar feeding mites; chinch bugs (e.g., hairy chinch bug (*Blissus leucopterus* hirtus Montandon) and southern chinch bug (*Blissus insularis* Barber) and other seed bugs from the family Lygaeidae); spittlebugs from the family Cercopidae; squash bugs from the family Coreidae; red bugs and cotton stainers from the family Pyrrhocoridae; and adults and immatures of the order Orthoptera including grasshoppers, locusts, and crickets (e.g., migratory grasshoppers (e.g., *Melanoplus sanguinipes* Fabricius, *M. differentialis* Thomas)), American grasshoppers (e.g., *Schistocerca americana* Drury), desert locust (*Schistocerca gregaria* Forskal), migratory locust (*Locusta migratoria* Linnaeus), bush locust (*Zonocerus* spp.); adults and immatures of the order Diptera including leafminers, midges, fruit flies (Tephritidae), frit flies (e.g., *Oscinella frit* Linnaeus), soil maggots, adults and nymphs of the orders Hemiptera and Homoptera such as plant bugs from the family Miridae; adults and immatures of the order Thysanoptera including onion thrips (*Thrips tabaci* Lindeman), flower thrips (*Frankliniella* spp.), and other foliar feeding thrips; and cicadas from the family Cicadidae. Agronomic pests also include Classes Nematoda, Cestoda, Trematoda, and Acanthocephala including economically important members of the orders Strongylida, Ascaridida, Oxyurida, Rhabditida, Spirurida, and Enoplida such as economically important agricultural pests (e.g., root knot nematodes in the genus *Meloidogyne*, lesion nematodes in the genus *Pratylenchus*, and stubby root nematodes in the genus *Trichodorus*).

Perilla oil, the *perilla* oil components, the perillaldehyde and carvone analogs, and the synergists having a cyclohexene ring described in this specification also have a synergistic effect with insecticides, such as pyrethrum, pyrethrins, pyrethroids, neonicotinoids, carbamates, organophosphates and organochlorines when used to control agronomonic pests.

Agronomic and non-agronomic pests include nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fiabricius), smoky brown cockroach (*Periplaneta fuliginosa* Service), Australian Cockroach (*Periplaneta australasiae* Fabr.), lobster cockroach (*Nauphoeta cinerea* Olivier) and smooth cockroach (*Symploce pallens* Stephens)); adults and larvae of the order Dermaptera including earwigs from the family Forficulidae (e.g., European earwig (*Forficula auricularia* Linnaeus), and black earwig (*Chelisoches morio* Fabricius)). Also included are adults and larvae of the order Acari (mites) such as spider mites and red mites in the family Tetranychidae (e.g., European red mite (*Panonychus ulmi* Koch), two spotted spider mite (*Tetranychus urticae* Koch), and McDaniel mite (*Tetranychus mcdanieli* McGregor)); mites important in human and animal health (e.g., dust mites in the family Epidermoptidae, follicle mites in the family Demodicidae, and grain mites in the family Glycyphagidae); ticks in the order Ixodidae (e.g., deer tick (*Ixodes scapularis* Say), Australian paralysis tick (*Ixodes holocyclus* Neumann), American dog tick (*Dermacentor variabilis* Say), and lone star tick (*Amblyomma americanum* Linnaeus)); scab and itch mites in the families Psoroptidae, Pyemotidae, and Sarcoptidae; crickets such as house cricket (*Acheta domesticus* Linnaeus), mole crickets (e.g., tawny mole cricket (*Scapteriscus vicinus* Scudder), and southern mole cricket (*Scapteriscus borellii* Giglio-Tos)); flies including house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera; mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Forster), odorous house ant (*Tapinoma sessile* Say)); insect pests of the Family Formicidae including the Florida carpenter ant (*Camponotus floridanus* Buckley), whitefooted ant (*Technomyrmex albipes* fr. Smith), big headed ants (*Pheidole* spp.), and ghost ant (*Tapinoma melanocephalum* Fabricius); bees (including carpenter bees), hornets, yellow jackets, wasps, and sawflies (*Neodiprion* spp.; *Cephus* spp.); insect pests of the order Isoptera including termites in the Termitidae (ex. *Macrotermes* sp.), Kalotermitidae (ex. *Cryptotermes* sp.), and Rhinotermitidae (ex. *Reticulitermes* spp., *Coptotermes* spp.), families the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus* capitis De Geer), body louse (*Pediculus humanus* humanus Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch); long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Arthropod pests also include spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus).

In some embodiments, the method comprises contacting an insect with an amount of any of the compositions described in this specification effective to control at least about 20%, at least about 30%, at least about 40%, at least about 50%, less than about 100%, less than about 90%, less than about 80%, less than about 70%, or less than about 60% of the contacted adult insect population. In some embodiments, the method comprises contacting an insect with an amount of any of the compositions described here effective to provide about 95% insect mortality. In some embodiments, the compositions provided in this specification comprise an amount (e.g., weight %) of at least one active agent that is suitably in a range that allows for at least some degree of insecticidal efficacy (e.g., more than 0%, but less that 95% insect mortality rate) when the composition is used, while not necessarily meeting the EPA requirements for a registered insecticide. For a composition to be registered and marketed as a "pesticide" within the United States for some uses (e.g., public health uses and pest control in residential structures) the EPA requires that a composition exhibits a 95% insect mortality at the lowest labeled rate. The EPA also regulates the upper limits of active agent(s) that can be used in practice in the environment.

In some embodiments, methods for insect control or controlling insects comprise contacting an insect with an amount of any of the compositions described in this specification. Control or controlling includes killing, knocking down, or a combination thereof, of at least a portion of a population of insects. A population includes at least two insects. Insect knockdown does not necessarily correlate to insect death, as insects can recover after the initial knockdown. In some embodiments, the composition is applied in an amount effective to knockdown at least about 20%, at least about 30%, at least about 40%, at least about 50%, at least about 60%, at least about 70%, at least about 80%, at least about 90%, at least about 95%, or at least about 98% of the contacted insect population. In some embodiments, the composition is applied in an amount effective to kill at least about 20%, at least about 30%, at least about 40%, at least about 50%, at least about 60%, at least about 70%, at least about 80%, at least about 90%, at least about 95%, or at least about 98% of the contacted insect population.

In some embodiments, the methods described here can comprise any known route, apparatus, and/or mechanism for the delivery or application of the compositions and formulations. In some embodiments, compositions may be applied as an aerosol, mist, fog, vapor, or ULV spray. In some embodiments, compositions may be applied as a surface contact treatment. A surface contact treatment includes surfaces that have been contacted with the composition, such as by painting, rolling, coating, dip coating or spraying the surface, or the compositions may be incorporated into fibers or other materials, such as, for example, a bednet to produce a material comprising a surface contact treatment. In some embodiments, the method comprises a sprayer. Traditional pesticide sprayers in the pest control markets are typically operated manually or electrically or are gas-controlled and use maximum pressures ranging from 15 to 500 psi generating flow rates from 5 gpm to 40 gpm. In other embodiments, the methods disclosed here comprise the use of the compositions and/or formulations in combination with any low volume environmental pest control device(s) such as, for example, ultra low volume (ULV) machines. Such combinations are useful in methods for mosquito control as well as other flying insects (e.g., flies, gnats, and flying ants) wherein contacting the insect with a low volume of the composition is possible and/or desirable. ULV machines suitably use low volume of material, for example at rates of about one gallon per hour (or ounces per minute), and typically utilize artificial wind velocities such as from, for example, an air source (e.g., pump or compressor) to break down and distribute the composition/formulation into a cold fog (suitably having average droplet particle sizes of about 1-30 µm). Any standard ground ULV equipment used for insect control such as, for example, a system including a (CETI) Grizzly aerosol generator can be used in the methods described here. A general ULV system includes a tank for the composition (e.g., insecticide), a transport system (e.g., a pump or pressurized tank), a flow control device, and a nozzle that atomizes the composition. Typically, ULV machines do not compress droplets. Rather, they often use a venture siphoning system, and can induce an artificial energizing of the droplets by adding an electrical current to the liquid (e.g., through the use an electrode located at the application tip). See U.S. Pat. No. 3,516,608 (Bowen et al.) incorporated here by reference.

It is to be understood that any numerical range recited in this specification includes all values from the lower value to the upper value. For example, if a concentration range is stated as 1% to 50%, it is intended that values such as 2% to 40%, 10% to 30%, or 1% to 3%, etc., are expressly enumerated in this specification. It is also to be understood that any numerical range recited in this specification includes all values from at least the lower value without an upper limit, and all values up to the upper value without a lower limit. These are only examples of what is specifically intended, and all possible combinations of numerical values between and including the lowest value and the highest value enumerated are to be considered to be expressly stated in this application.

It also is to be understood that the invention is not limited in its application to the details of construction and the arrangement of components set forth in the description. Also, it is to be understood that the phraseology and terminology used in this specification is for the purpose of description and should not be regarded as limiting. The use of the terms "a" and "an" and "the" and similar referents in the context of describing the invention are to be construed to cover both the singular and the plural, unless otherwise indicated in this specification or clearly contradicted by context. The terms "comprising," "having," "including," and "containing" are to be construed as open-ended terms (i.e., meaning "including but not limited to") unless otherwise noted. All methods described in this specification can be performed in any suitable order unless otherwise indicated in this specification or otherwise clearly contradicted by context. Patent applications, patents and literature references cited here are specifically and completely incorporated by reference in their entirety. Where inconsistent interpretations are possible, the present disclosure controls.

The use of any and all examples, or exemplary language (e.g., "such as") provided here, is intended merely to illustrate aspects and embodiments of the disclosure and does not limit the scope of the claims.

EXAMPLES

Example 1

Materials and Methods

Reagents.

Pyrethrins were supplied as a 20% Manufacturing Use Product or "MUP" (PyGanic® MUP 20, MGK (Minneapolis, Minn.). Mineral oil was supplied by Brenntag Great Lakes, LLC. Diluents were supplied by Stepan Company, Procter & Gamble Chemicals, and Vertec Biosolvents. Insecticides were purchased from Sigma Aldrich (St. Louis, Mo.). Essential oils or botanicals were purchased from The Good Scents Company, The Lebermuth Company, and Takasago International Corporation. *Perilla* oil components and insecticides were obtained from Sigma Aldrich (St. Louis, Mo.) or City Chemical (West Haven, Conn.).

Topical Bioassay Method.

Adult mosquitoes were reared on 10% sucrose solution in an insectary maintained at 27° C., 45% RH and 12/12 hr light/dark photoperiod. Adult female *Aedes aegypti* mosquitoes were segregated in 18"×18" screen cages based on date of eclosion, therefore the exact age of the mosquitoes were known for bioassays.

Ten female mosquitoes, aged four to six days after eclosion, were aspirated out of their respective cage and into a small glass jar. The mosquitoes were then anesthetized with $CO_2$ gas for 30 seconds. After the adults were anesthetized, they were quickly placed on a plastic platform for treatment application. Treatments were serially diluted (using a BrandTech Scientific Transferpette S pipette (100-1000 µL), labeled centrifuge tubes, and a vortex mixer) from stocks of insecticides using reagent grade acetone as the diluent to concentrations as indicated for each treatment solution. A treatment solution may contain additional ingredients as indicated for each study.

Using a Hamilton PB00-1 Repeating Dispenser with a Hamilton 25 Microliter Syringe, 0.5 µL of each treatment solution was applied to the thorax of each mosquito. Immediately following the application of the treatment, the mosquitoes were gently transferred into a clean paper cup and covered with screen. The mesh screen prevented the mosquitoes from escaping and allowed the specimens to be viewed for ratings. A cotton ball soaked with 10% sucrose solution was inserted into a side hole of each cup for hydration and nourishment. Each treatment variable in the study was replicated three times using separate cups for each replication.

In each study, an untreated control and an acetone treated control was included to ensure that the $CO_2$ gas and the acetone diluent had no lethal effect on the mosquitoes. The untreated controls treatments were anesthetized for 30 seconds and gently transferred to the paper cups. The acetone treated control was treated exactly as described above except that the solution applied to each mosquito was undiluted acetone.

The condition of the mosquitoes in each cup was recorded at one hour and 24 hours after initial treatment. The condition classifications used were (1) alive and flying, (2) alive and unable to fly, or (3) dead. The percent mortality for each treatment was calculated by summing the mortalities of each replicate then calculating the percent dead from the total number of mosquitoes.

Statistical Analysis.

Where indicated, the mortality data were subjected to probit analysis using the Statistical Analysis System Version 9.1 program PROC PROBIT (SAS Institute (2003) PROC user's manual, version 9.1. SAS Institute, Cary, N.C.). This analysis estimates an $LD_{50}$ value or the dose necessary to achieve 50% mortality. In all cases the likelihood ratio (L.R.) or Pearson chi-square goodness-of-fit values indicated that the data adequately conformed to the probit model (ibid).

Mosquito Stocks for Field Trials.

The *Culex* and *Aedes* adult mosquitoes for the field trial were reared from pupae shipped overnight from the Clarke Technical Center Insectary to the Florida Research Laboratory. Mosquitoes were fed a 10% sugar water solution upon emergence and were maintained on 10% sugar water throughout the field trials. For laboratory experiments and assays, the desired number of adult mosquitoes (typically about 3-7 days old) were isolated and maintained on 10% sugar water solution.

Example 2

*Perilla* leaf oil was tested for efficacy against 3- to 5-day old adult *Aedes aegypti*. Solutions tested included *Perilla* oil at 1%, 2%, 4%, 6%, 8%, and 10%. At 1 hour we obtained 0%, 37%, 97%, 93%, 100%, and 100% knockdown, respectively. At 24 hours we obtained 0%, 20%, 83%, 93%, 100%, and 100% mortality, respectively. The $CO_2$ control and acetone standard both had 0% knockdown at 1 hour, and 0% mortality at 24 hours. These data suggest that perilla leaf oil exposure by contact leads to *Aedes aegypti* mortality.

Example 3

*Perilla* leaf oil at concentrations of 1%, 5%, and 10% was tested for efficacy against 1- to 2-day old adult *Culex quinquefasciatus*. At 1 hour we obtained 17%, 100%, and 100% knockdown, respectively. At 24 hours we obtained 10%, 100%, and 100% mortality, respectively. The $CO_2$ control had 0% knockdown at 1 hour, and 0% mortality at 24 hours. The acetone standard had 17% knockdown at 1 hour, and 20% mean mortality at 24 hours. These data suggest that perilla leaf oil exposure by contact leads to *Culex quinquefasciatus* mortality.

Example 4

*Perilla* seed oil at concentrations of 1%, 5%, 10%, and 20% was tested for efficacy against 4- to 6-day old adult *Aedes aegypti*. At 1 hour we obtained 7%, 77%, 83%, and 87% knockdown, respectively. At 24 hours we obtained 0%, 23%, 30%, and 77% mortality, respectively. The $CO_2$ control and acetone standard both had 0% knockdown at 1 hour, and 0% mortality at 24 hours. These data suggest that relatively high rates of perilla seed oil exposure by contact, leads to mosquito mortality.

Example 5

Perilla seed oil at concentrations of 1%, 5%, 10%, and 20% was again tested for efficacy against 4- to 6-day old adult Aedes aegypti. At 1 hour we obtained 0%, 63%, 87%, and 93% knockdown, respectively. At 24 hours we obtained 0%, 20%, 77%, and 90% mortality, respectively. The $CO_2$ control had 0% knockdown at 1 hour, and 0% mortality at 24 hours. The acetone standard had 7% knockdown at 1 hour, and 7% mean mortality at 24 hours. These data suggest that relatively high rates of perilla seed oil exposure by contact, leads to mosquito mortality.

Example 6

Linolenic acid at concentrations of 1%, 5%, 10%, and 20% was tested for efficacy against 4- to 6-day old adult Aedes aegypti. At 1 hour we obtained 0%, 27%, 40%, and 93% knockdown, respectively. At 24 hours we obtained 3%, 33%, 83%, and 93% mortality, respectively. The $CO_2$ control had 0% knockdown at 1 hour, and 7% mortality at 24 hours. The acetone standard had 0% knockdown at 1 hour, and 0% mortality at 24 hours. These data suggest that relatively high rates of linolenic acid exposure by contact, leads to mosquito mortality.

Example 7

(S)-(−)-Perillaldehyde at concentrations of 1%, 5%, 10%, and 20% was tested for efficacy against 4- to 6-day old adult Aedes aegypti. At 1 hour we obtained 3%, 93%, 100%, and 97% knockdown, respectively. At 24 hours we obtained 7%, 93%, 100%, and 100% mortality, respectively. The $CO_2$ control had 0% knockdown at 1 hour, and 7% mortality at 24 hours. The acetone standard had 0% knockdown at 1 hour, and 0% mortality at 24 hours. These data suggest that perillaldehyde exposure by contact leads to mosquito mortality.

Example 8

Farnesene at concentrations of 1%, 5%, 10%, and 20% was tested for efficacy against 4- to 6-day old adult Aedes aegypti. At 1 hour we obtained 0%, 0%, 87%, and 100% knockdown, respectively. At 24 hours we obtained 3%, 13%, 70%, and 100% mortality, respectively. The $CO_2$ control had 0% knockdown at 1 hour, and 7% mortality at 24 hours. The acetone standard had 0% knockdown at 1 hour, and 0% mortality at 24 hours. These data suggest that relatively high rates of farnesene exposure by contact leads to mosquito mortality.

Example 9

β-Caryophyllene at concentrations of 1%, 5%, 10%, and 20% was tested for efficacy against 4- to 6-day old adult Aedes aegypti. At 1 hour we obtained 0%, 10%, 57%, and 93% knockdown, respectively. At 24 hours we obtained 0%, 17%, 40%, and 83% mortality, respectively. The $CO_2$ control had 0% knockdown at 1 hour, and 7% mortality at 24 hours. The acetone standard had 0% knockdown at 1 hour, and 0% mortality at 24 hours. These data suggest that β-caryophyllene exposure by contact, leads to mosquito mortality.

Example 10

Dinotefuran and perilla oil were tested for efficacy against 5- to 7-day old adult Aedes aegypti. Solutions tested included Solution 1 (0.06 μg/mosquito of dinotefuran), Solution 2 (3% perilla oil), and Solution 3 (0.06 μg/mosquito of dinotefuran with 3% perilla oil). At 1 hour we obtained 37%, 83%, and 97% knockdown for Solutions 1, 2, and 3, respectively. At 24 hours we obtained 57%, 73%, and 97% mortality respectively. The $CO_2$ control and acetone standard both had 0% knockdown at 1 hour, and 0% mortality at 24 hours. Results are shown in Table 2.

TABLE 2

Efficacy of perilla oil, dinotefuran, and a combination of both against adult, virgin, female Aedes aegypti mosquitoes.

| ACTIVE INGREDIENT | CONCENTRATION | % MORTALITY AFTER 24 HRS | |
|---|---|---|---|
| PERILLA OIL | 3% | 57 | |
| DINOTEFURAN | 0.06 μg | 73 | |
| | | OBS.* | CALC.** |
| PERILLA OIL + DINOTEFURAN | 3% + 0.06 μg | 97‡ | 88.39 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

Example 11

Dinotefuran and perilla oil were tested for efficacy against 4- to 6-day old adult Aedes aegypti. Solutions tested included Solution 1 (2% perilla oil), Solution 2 (0.004 μg/mosquito dinotefuran with 2% perilla oil), Solution 3 (0.006 μg/mosquito dinotefuran with 2% perilla oil), and Solution 4 (0.008 μg/mosquito of dinotefuran with 2% perilla oil). At 1 hour we obtained 13%, 87%, 80%, and 90% knockdown for Solutions 1, 2, 3, and 4, respectively. At 24 hours we obtained 0%, 77%, 77%, and 90% mortality respectively. The $CO_2$ control and acetone standard both had 0% knockdown at 1 hour and 0% mortality at 24 hours. Dinotefuran was tested at discriminating doses 7.5 to 15 times lower that the $LD_{50}$ of 0.06 μg/mosquito. These data suggest that the application of dinotefuran and perilla oil together leads to an increase in mortality over the application of perilla oil alone.

Example 12

Dinotefuran and perilla oil were tested individually and in combination for efficacy against 3- to 5-day old adult Aedes aegypti where dinotefuran was tested at discriminating doses 7.5 to 15 times lower than the $LD_{50}$ of 0.06 μg/mosquito. Results are shown in Table 3 and Table 4.

TABLE 3

Efficacy data for dinotefuran and perilla oil tested individually and in combination.

| Treatment | 1 hour knockdown | 24 hour mortality |
|---|---|---|
| $CO_2$ Control | 0% | 0% |
| Acetone Standard | 0% | 0% |
| 3% Perilla oil | 40% | 60% |
| 0.004 μg/mosquito dinotefuran | 0% | 0% |
| 0.006 μg/mosquito dinotefuran | 0% | 0% |
| 0.008 μg/mosquito dinotefuran | 17% | 0% |
| 0.004 μg/mosquito dinotefuran + 3% Perilla Oil | 100% | 90% |
| 0.006 μg/mosquito dinotefuran + 3% Perilla Oil | 100% | 97% |
| 0.008 μg/mosquito dinotefuran + 3% Perilla Oil | 100% | 93% |

TABLE 4

Efficacy of perilla oil, dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| PERILLA OIL | 3%[T] | 60 | |
| DINOTEFURAN | 0.004 μg | 0 | |
| | | OBS.* | CALC.** |
| PERILLA OIL + DINOTEFURAN | 3% + 0.004 μg | 90 [‡] | 60 |
| PERILLA OIL | 3% | 60 | |
| DINOTEFURAN | 0.006 μg | 0 | |
| | | OBS.* | CALC.** |
| PERILLA OIL + DINOTEFURAN | 3% + 0.006 μg | 97 [‡] | 60 |
| PERILLA OIL | 3% | 60 | |
| DINOTEFURAN | 0.008 μg | 0 | |
| | | OBS.* | CALC.** |
| PERILLA OIL + DINOTEFURAN | 3% + 0.008 μg | 93 [‡] | 60 |

[T]3% efficacy was derived from data that underwent probit analysis to predict lethal dose values from topical application bioassay.
*Obs. = observed efficacy
**Calc. = efficacy calculated using Colby (1967) formula
[‡] Since the actual insecticidal kill rate exceeds the calculated value, then the action of the combination is super-additive or a synergistic effect is present.

Example 13

Solution 1 (2% of perillaldehyde), Solution 2 (0.008 μg/mosquito of dinotefuran), and Solution 3 (0.008 μg/mosquito of dinotefuran with 2% of perillaldehyde) were tested for efficacy against 3- to 5-day old adult *Culex quinquefasciatus*. At 1 hour we obtained 33%, 10%, and 100% knockdown for Solutions 1, 2, and 3, respectively. At 24 hours we obtained 13%, 77%, and 100% mortality for Solutions 1, 2, and 3, respectively. The $CO_2$ control and acetone standard both had 0% knockdown at 1 hour, and 0% mortality at 24 hours. Results are shown in Table 5.

TABLE 5

Efficacy of perillaldehyde, dinotefuran, and a combination of both against adult, virgin, female *Culex quinquefasciatus* mosquitoes.

| ACTIVE INGREDIENT | CONCENTRATION | % MORTALITY AFTER 24 HRS | |
|---|---|---|---|
| PERILLALDEHYDE | 2% | 13 | |
| DINOTEFURAN | 0.008 μg | 77 | |

TABLE 5-continued

Efficacy of perillaldehyde, dinotefuran, and a combination of both against adult, virgin, female *Culex quinquefasciatus* mosquitoes.

| | | OBS.* | CALC.** |
|---|---|---|---|
| PERILLALDEHYDE + DINOTEFURAN | 2% + 0.008 μg | 100[‡] | 79.99 |

*Obs. = observed efficacy
**Calc. = efficacy calculated using Colby (1967) formula
[‡]Since the actual insecticidal kill rate exceeds the calculated value, then the action of the combination is super-additive or a synergistic effect is present.

Example 14

In support of example 2, Solution 1 (0.008 μg/mosquito of dinotefuran) and Solution 2 (0.008 μg/mosquito of dinotefuran with 2% of perillaldehyde) were tested for efficacy against 3- to 5-day old adult *Culex quinquefasciatus*. At 1 hour we obtained 10% and 90% knockdown for Solution 1 and 2, respectively. At 24 hours we obtained 73% and 90% mortality for Solution 1 and 2, respectively. The $CO_2$ control and acetone standard both had 0% knockdown at 1 hour, and 0% mortality at 24 hours.

Example 15

In support of examples 2 and 3, Solution 1 (0.008 μg/mosquito of dinotefuran with 3% of perillaldehyde) was tested for efficacy against 4- to 6-day old adult *Culex quinquefasciatus*. At 1 hour we obtained 100% knockdown; and at 24 hours we obtained 100% mortality. The $CO_2$ control and acetone standard both had 0% knockdown at 1 hour, and 0% mortality at 24 hours.

Example 16

Dinotefuran and perillaldehyde were tested individually and in combination for efficacy against 3- to 5-day old adult *Aedes aegypti* where dinotefuran was tested at discriminating doses 7.5 to 15 times lower than the $LD_{50}$ of 0.06 μg/mosquito. Results are shown in Table 6 and Table 7.

TABLE 6

Efficacy data for dinotefuran and perillaldehyde tested individually and in combination.

| Treatment | 1 hour knockdown | 24 hour mortality |
|---|---|---|
| $CO_2$ Control | 0% | 0% |
| Acetone Standard | 0% | 0% |

TABLE 6-continued

Efficacy data for dinotefuran and perillaldehyde tested individually and in combination.

| Treatment | 1 hour knockdown | 24 hour mortality |
|---|---|---|
| 3% Perillaldehyde | 53% | 43% |
| 0.004 µg/mosquito dinotefuran | 0% | 0% |
| 0.006 µg/mosquito dinotefuran | 3% | 3% |
| 0.008 µg/mosquito dinotefuran | 3% | 13% |
| 0.06 µg/mosquito dinotefuran | 77% | 53% |
| 0.004 µg/mosquito dinotefuran + 3% Perillaldehyde | 100% | 93% |
| 0.006 µg/mosquito dinotefuran + 3% Perillaldehyde | 100% | 97% |
| 0.008 µg/mosquito dinotefuran + 3% Perillaldehyde | 93% | 93% |
| 0.06 µg/mosquito dinotefuran + 3% Perillaldehyde | 100% | 100% |

TABLE 7

Efficacy of perillaldehyde, dinotefuran, and a combination of both against adult, virgin, female *Aedes aegypti* mosquitoes.

| ACTIVE INGREDIENT | CONCENTRATION | PERCENT EFFICACY AFTER 24 HRS | |
|---|---|---|---|
| PERILLALDEHYDE | 3% | 43 | |
| DINOTEFURAN | 0.06 µg | 53 | |
| | | OBS.* | CALC.** |
| PERILLALDEHYDE + DINOTEFURAN | 3% + 0.06 µg | 100 ‡ | 73.21 |
| PERILLALDEHYDE | 3% | 43 | |
| DINOTEFURAN | 0.004 µg | 0 | |
| | | OBS.* | CALC.** |
| PERILLALDEHYDE + DINOTEFURAN | 3% + 0.004 µg | 93 ‡ | 43 |
| PERILLALDEHYDE | 3% | 43 | |
| DINOTEFURAN | 0.006 µg | 3 | |
| | | OBS.* | CALC.** |
| PERILLALDEHYDE + DINOTEFURAN | 3% + 0.006 µg | 97 ‡ | 44.71 |
| PERILLALDEHYDE | 3% | 43 | |
| DINOTEFURAN | 0.008 µg | 13 | |
| | | OBS.* | CALC.** |
| PERILLALDEHYDE + DINOTEFURAN | 3% + 0.008 µg | 93 ‡ | 50.41 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

Example 17

Dinotefuran and linolenic acid were tested for efficacy against 4- to 6-day old adult *Aedes aegypti*. For the following concentrations 3% linolenic acid, 0.06 µg/mosquito of dinotefuran, and 0.06 µg/mosquito of dinotefuran with 3% linolenic acid, at 1 hour we obtained 17%, 50%, and 100% knockdown respectively. At 24 hours we obtained 3%, 47%, and 100% mortality respectively. The $CO_2$ control and acetone standard both had 0% knockdown at 1 hour, and 0% mortality at 24 hours. Results are shown in Table 8.

TABLE 8

Efficacy of linolenic acid, dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| LINOLENIC ACID | 3% | 3 | |
| DINOTEFURAN | 0.06 µg | 47 | |
| | | OBS.* | CALC.** |
| LINOLENIC ACID + DINOTEFURAN | 3% + 0.06 µg | 100 ‡ | 48.59 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 18

Dinotefuran and β-caryophyllene were tested for efficacy against 4- to 6-day old adult *Aedes aegypti*. For the following concentrations 3% β-caryophyllene, 0.06 µg/mosquito of dinotefuran, and 0.06 µg/mosquito of dinotefuran with 3% β-caryophyllene, at 1 hour we obtained 3%, 50%, and 100% knockdown respectively. At 24 hours we obtained 3%, 47%, and 100% mortality respectively. The $CO_2$ control and acetone standard both had 0% knockdown at 1 hour, and 0% mortality at 24 hours. Results are shown in Table 9.

TABLE 9

Efficacy of β-caryophyllene, dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| β-CARYOPHYLLENE | 3% | 3 | |
| DINOTEFURAN | 0.06 µg | 47 | |
| | | OBS.* | CALC.** |
| β-CARYOPHYLLENE + DINOTEFURAN | 3% + 0.06 µg | 100 ‡ | 48.59 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 19

Dinotefuran and farnesene were tested for efficacy against 4- to 6-day old adult *Aedes aegypti*. For the following concentrations 3% farnesene, 0.06 µg/mosquito of dinotefuran, and 0.06 µg/mosquito of dinotefuran with 3% farnesene, at 1 hour we obtained 3%, 50%, and 97% knockdown respectively. At 24 hours we obtained 7%, 47%, and 97% mean mortality respectively. The $CO_2$ control and acetone standard both had 0% knockdown at 1 hour, and 0% mean mortality at 24 hours. Results are shown in Table 10.

TABLE 10

Efficacy of farnesene, dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| FARNESENE | 3% | 7 | |
| DINOTEFURAN | 0.06 μg | 47 | |
| | | OBS.* | CALC.** |
| FARNESENE + DINOTEFURAN | 3% + 0.06 μg | 97‡ | 50.71 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 20

Permethrin and perillaldehyde were tested for efficacy against 4- to 6-day old adult *Aedes aegypti*. For the following concentrations 3% perillaldehyde, 0.0004 μg/mosquito of permethrin, and 0.0004 μg/mosquito of permethrin with 3% perillaldehyde, at 1 hour we obtained 10%, 93%, and 100% knockdown respectively. At 24 hours we obtained 10%, 70%, and 100% mortality respectively. The $CO_2$ control had 0% knockdown at 1 hour, and 0% mortality at 24 hours. The acetone standard had 3% knockdown at 1 hour, and 7% mortality at 24 hours. Results are shown in Table 11.

TABLE 11

Efficacy of perillaldehyde, permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| PERILLALDEHYDE | 3% | 10 | |
| PERMETHRIN | 0.0004 μg | 70 | |
| | | OBS.* | CALC.** |
| PERILLALDEHYDE + ERMETHRIN | 3% + 0.0004 μg | 100‡ | 79.30 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 21

Permethrin and farnesene were tested for efficacy against 4- to 6-day old adult *Aedes aegypti*. For the following concentrations 3% farnesene, 0.0004 μg/mosquito of permethrin, and 0.0004 μg/mosquito of permethrin with 3% farnesene, at 1 hour we obtained 0%, 93%, and 20% knockdown respectively. At 24 hours we obtained 0%, 70%, and 47% mortality respectively. The $CO_2$ control had 0% knockdown at 1 hour, and 0% mortality at 24 hours. The acetone standard had 3% knockdown at 1 hour, and 7% mortality at 24 hours. Results are shown in Table 12.

TABLE 12

Efficacy of farnesene, permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| FARNESENE | 3% | 0 | |
| PERMETHRIN | 0.0004 μg | 70 | |
| | | OBS.* | CALC.** |
| FARNESENE + PERMETHRIN | 3% + 0.0004 μg | 47‡ | 70 |

*Obs. = observed efficacy
**Calc. = efficacy calculated using Colby (1967) formula
‡Since the calculated insecticidal kill rate exceeds the observed value, then the action of the combination is antagonistic.

Example 22

Permethrin and linolenic acid were tested for efficacy against 4- to 6-day old adult *Aedes aegypti*. For the following concentrations 3% linolenic acid, 0.0004 μg/mosquito of permethrin, and 0.0004 μg/mosquito of permethrin with 3% linolenic acid, at 1 hour we obtained 7%, 93%, and 77% knockdown respectively. At 24 hours we obtained 60%, 70%, and 63% mortality respectively. The $CO_2$ control had 0% knockdown at 1 hour, and 0% mortality at 24 hours. The acetone standard had 3% knockdown at 1 hour, and 7% mortality at 24 hours. Results are shown in Table 13.

TABLE 13

Efficacy of linolenic acid, permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| LINOLENIC ACID | 3% | 60 | |
| PERMETHRIN | 0.0004 μg | 70 | |
| | | OBS.* | CALC.** |
| LINOLENIC ACID + PERMETHRIN | 3% + 0.0004 μg | 63‡ | 88 |

*Obs. = observed efficacy
**Calc. = efficacy calculated using Colby (1967) formula
‡Since the calculated insecticidal kill rate exceeds the observed value, then the action of the combination is antagonistic.

Example 23

Permethrin and β-caryophyllene were tested for efficacy against 4- to 6-day old adult *Aedes aegypti*. For the following concentrations 3% β-caryophyllene, 0.0004 μg/mosquito of permethrin, and 0.0004 μg/mosquito of permethrin with 3% β-caryophyllene, at 1 hour we obtained 0%, 93%, and 43% knockdown respectively. At 24 hours we obtained 10%, 70%, and 43% mean mortality respectively. The $CO_2$ control had 0% knockdown at 1 hour, and 0% mean mortality at 24 hours. The acetone standard had 3% knockdown at 1 hour, and 7% mean mortality at 24 hours. Results are shown in Table 14.

TABLE 14

Efficacy of β-caryophyllene, permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| β-CARYOPHYLLENE | 3% | 10 | |
| PERMETHRIN | 0.0004 μg | 70 | |
| | | OBS.* | CALC.** |
| β-CARYOPHYLLENE + PERMETHRIN | 3% + 0.0004 μg | 43‡ | 79.40 |

*Obs. = observed efficacy
**Calc. = efficacy calculated using Colby (1967) formula
‡Since the calculated insecticidal kill rate exceeds the observed value, then the action of the combination is antagonistic.

Example 24

Pyrethrin and *perilla* oil were tested for efficacy against 3- to 5-day old adult *Aedes aegypti*. Solutions tested included Solution 1 (0.0001 μg/mosquito of pyrethrin with 1% perilla oil), Solution 2 (0.0001 μg/mosquito of pyrethrin with 5% *perilla* oil), Solution 3 (0.0001 μg/mosquito of pyrethrin with 10% *perilla* oil), Solution 4 (0.001 μg/mosquito of pyrethrin with 1% *perilla* oil), Solution 5 (0.001 μg/mosquito of pyrethrin with 5% *perilla* oil), and Solution 6 (0.001 μg/mosquito of pyrethrin with 10% *perilla* oil). At 1 hour we obtained 0%, 100%, 100%, 70%, 93% and 97% knockdown for Solutions 1, 2, 3, 4, and 6, respectively. At 24 hours we obtained 3%, 93%, 97%, 57%, 87%, and 93% mortality, respectively. The $CO_2$ control and acetone standard both had 0% knockdown at 1 hour, and 0% mortality at 24 hours. These data suggest that increased rates of both pyrethrin and *perilla* oil, applied together, results in greater mortality.

Example 25

Pyrethrin and β-caryophyllene were tested for efficacy against 4- to 6-day old adult *Aedes aegypti*. For the following concentrations 3% β-caryophyllene, 0.002 μg/mosquito of pyrethrin, and 0.002 μg/mosquito of pyrethrin with 3% β-caryophyllene, at 1 hour we obtained 0%, 90%, and 100% knockdown respectively. At 24 hours we obtained 20%, 57%, and 97% mortality respectively. The $CO_2$ control and acetone standard both had 0% knockdown at 1 hour, and 0% mortality at 24 hours. Results are shown in Table 15.

TABLE 15

Efficacy of β-caryophyllene, pyrethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| β-CARYOPHYLLENE | 3% | 20 | |
| PYRETHRIN | 0.002 μg | 57 | |
| | | OBS.* | CALC.** |
| β-CARYOPHYLLENE + PYRETHRIN | 3% + 0.002 μg | 97‡ | 65.60 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 26

Pyrethrin and farnesene were tested for efficacy against 4- to 6-day old adult *Aedes aegypti*. For the following concentrations 3% farnesene, 0.002 μg/mosquito of pyrethrin, and 0.002 μg/mosquito of pyrethrin with 3% farnesene, at 1 hour we obtained 0%, 90%, and 83% knockdown respectively. At 24 hours we obtained 0%, 57%, and 73% mortality respectively. The $CO_2$ control and acetone standard both had 0% knockdown at 1 hour, and 0% mortality at 24 hours. Results are shown in Table 16.

TABLE 16

Efficacy of farnesene, pyrethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| FARNESENE | 3% | 0 | |
| PYRETHRIN | 0.002 μg | 57 | |
| | | OBS.* | CALC.** |
| FARNESENE + PYRETHRIN | 3% + 0.002 μg | 73‡ | 57 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 27

We tested pyrethrin+linolenic acid for efficacy against 4- to 6-day old adult *Aedes aegypti*. For the following concentrations 3% linolenic acid, 0.002 μg/mosquito of pyrethrin, and 0.002 μg/mosquito of pyrethrin with 3% linolenic acid, at 1 hour we obtained 17%, 90%, and 50% knockdown respectively. At 24 hours we obtained 7%, 57%, and 37% mean mortality respectively. The $CO_2$ control and acetone standard both had 0% knockdown at 1 hour, and 0% mean mortality at 24 hours. Results are shown in Table 17.

TABLE 17

Efficacy of linolenic acid, pyrethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| LINOLENIC ACID | 3% | 7 | |
| PYRETHRIN | 0.002 μg | 57 | |
| | | OBS.* | CALC.** |
| LINOLENIC ACID + PYRETHRIN | 3% + 0.002 μg | 37‡ | 60.01 |

*Obs. = observed efficacy
**Calc. = efficacy calculated using Colby (1967) formula
‡Since the calculated insecticidal kill rate exceeds the observed value, then the action of the combination is antagonistic.

Example 28

We tested pyrethrin+perillaldehyde for efficacy against 3- to 5-day old adult *Culex quinquefasciatus*. For the concentration, 2% of perillaldehyde, and 0.001 μg/mosquito of pyrethrin, and 0.001 μg/mosquito of pyrethrin with 2% of perillaldehyde, at 1 hour we obtained 33%, 10%, and 80% knockdown respectively. At 24 hours we obtained 13%, 7%, and 33% mean mortality respectively. The $CO_2$ control and acetone standard both had 0% knockdown at 1 hour, and 0% mean mortality at 24 hours. Results are shown in Table 18.

TABLE 18

Efficacy of perillaldehyde, pyrethrin, and a combination of both against adult, virgin, female Culex quinquefasciatus mosquitoes.

| ACTIVE INGREDIENT | CONCENTRATION | % MORTALITY AFTER 24 HRS |
|---|---|---|
| PERILLALDEHYDE | 3% | 13 |
| PYRETHRIN | 0.001 μg | 7 |

TABLE 18-continued

Efficacy of perillaldehyde, pyrethrin, and a combination of both against adult, virgin, female Culex quinquefasciatus mosquitoes.

| | | OBS.* | CALC.** |
|---|---|---|---|
| PERILLALDEHYDE + PYRETHRIN | 3% + 0.001 μg | 33‡ | 19.09 |

* Obs. = observed efficacy
** Calc. = efficacy calculated using Colby (1967) formula
‡Since the actual insecticidal kill rate exceeds the calculated value, then the action of the combination is super-additive or a synergistic effect is present.

Example 29

Etofenprox and *perilla* oil were tested for efficacy against 5- to 7-day old adult *Aedes aegypti*. Solutions tested included Solution 1 (0.001 μg/mosquito of etofenprox), Solution 2 (3% *perilla* oil), and Solution 3 (0.001 μg/mosquito of etofenprox with 3% *perilla* oil). At 1 hour we obtained 73%, 83%, and 87% knockdown respectively. At 24 hours we obtained 40%, 73%, and 87% mortality respectively. The $CO_2$ control and acetone standard both had 0% knockdown at 1 hour, and 0% mortality at 24 hours. Results are shown in Table 19.

TABLE 19

Efficacy of perilla oil, etofenprox, and a combination of both against adult, virgin, female *Aedes aegypti* mosquitoes.

| ACTIVE INGREDIENT | CONCENTRATION | % MORTALITY AFTER 24 HRS | |
|---|---|---|---|
| PERILLA OIL | 3% | 73 | |
| ETOFENPROX | 0.001 μg | 40 | |
| | | OBS.* | CALC.** |
| PERILLA OIL + ETOFENPROX | 3% + 0.001 μg | 87‡ | 83.8 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 30

Etofenprox and perillaldehyde were tested for efficacy against 3- to 5-day old adult *Aedes aegypti*. For the following concentrations 3% perillaldehyde, 0.002 μg/mosquito of etofenprox, and 0.002 μg/mosquito of etofenprox with 3% perillaldehyde, at 1 hour we obtained 90%, 83%, and 93% knockdown respectively. At 24 hours we obtained 77%, 53%, and 93% mortality respectively. The $CO_2$ control and acetone standard both had 0% knockdown at 1 hour, and 0% mortality at 24 hours. Results are shown in Table 20.

TABLE 20

Efficacy of perillaldehyde, etofenprox, and a combination of both against adult, virgin, female *Aedes aegypti* mosquitoes.

| ACTIVE INGREDIENT | CONCENTRATION | % MORTALITY AFTER 24 HRS | |
|---|---|---|---|
| PERILLALDEHYDE | 3% | 77 | |
| ETOFENPROX | 0.002 μg | 53 | |
| | | OBS.* | CALC.** |
| PERILLALDEHYDE + ETOFENPROX | 3% + 0.002 μg | 93‡ | 89.19 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 31

Etofenprox and farnesene were tested for efficacy against 3- to 5-day old adult *Aedes aegypti*. For the following concentrations 3% farnesene, 0.002 μg/mosquito of etofenprox, and 0.002 μg/mosquito of etofenprox with 3% farnesene, at 1 hour we obtained 7%, 83%, and 60% knockdown respectively. At 24 hours we obtained 13%, 53%, and 50% mortality respectively. The $CO_2$ control and acetone standard both had 0% knockdown at 1 hour, and 0% mortality at 24 hours. Results are shown in Table 21.

TABLE 21

Efficacy of farnesene, etofenprox, and a combination of both against adult, virgin, female *Aedes aegypti* mosquitoes.

| ACTIVE INGREDIENT | CONCENTRATION | % MORTALITY AFTER 24 HRS | |
|---|---|---|---|
| FARNESENE | 3% | 13 | |
| ETOFENPROX | 0.002 μg | 53 | |
| | | OBS.* | CALC.** |
| FARNESENE + ETOFENPROX | 3% + 0.002 μg | 50‡ | 59.11 |

*Obs. = observed efficacy
**Calc. = efficacy calculated using Colby (1967) formula
‡Since the calculated insecticidal kill rate exceeds the observed value, then the action of the combination is antagonistic.

Example 32

Etofenprox and β-caryophyllene were tested for efficacy against 3- to 5-day old adult *Aedes aegypti*. For the following concentrations 3% β-caryophyllene, 0.002 μg/mosquito of etofenprox, and 0.002 μg/mosquito of etofenprox with 3% β-caryophyllene, at 1 hour we obtained 13%, 83%, and 87% knockdown respectively. At 24 hours we obtained 3%, 53%, and 77% mortality respectively. The $CO_2$ control and acetone standard both had 0% knockdown at 1 hour, and 0% mortality at 24 hours. Results are shown in Table 22.

TABLE 22

Efficacy of β-caryophyllene, etofenprox, and a combination of both against adult, virgin, female *Aedes aegypti* mosquitoes.

| ACTIVE INGREDIENT | CONCENTRATION | % MORTALITY AFTER 24 HRS | |
|---|---|---|---|
| β-CARYOPHYLLENE | 3% | 77 | |
| ETOFENPROX | 0.002 μg | 53 | |
| | | OBS.* | CALC.** |
| β-CARYOPHYLLENE + ETOFENPROX | 3% + 0.002 μg | 93‡ | 89.19 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 33

We tested etofenprox+linolenic acid for efficacy against 3- to 5-day old adult *Aedes aegypti*. For the following concentrations 3% linolenic acid, 0.002 μg/mosquito of etofenprox, and 0.002 μg/mosquito of etofenprox with 3% linolenic acid, at 1 hour we obtained 0%, 83%, and 0% knockdown respectively. At 24 hours we obtained 3%, 53%, and 7% mean mortality respectively. The $CO_2$ control and acetone standard both had 0% knockdown at 1 hour, and 0% mean mortality at 24 hours. Results are shown in Table 23.

TABLE 23

Efficacy of linolenic acid, etofenprox, and a combination of both against adult, virgin, female *Aedes aegypti* mosquitoes.

| ACTIVE INGREDIENT | CONCENTRATION | % MORTALITY AFTER 24 HRS | |
|---|---|---|---|
| LINOLENIC ACID | 3% | 3 | |
| ETOFENPROX | 0.002 µg | 53 | |
| | | OBS.* | CALC.** |
| LINOLENIC ACID + ETOFENPROX | 3% + 0.002 µg | 7[‡] | 54.41 |

*Obs. = observed efficacy
**Calc. = efficacy calculated using Colby (1967) formula
[‡]Since the calculated insecticidal kill rate exceeds the observed value, then the action of the combination is antagonistic.

Example 34

Ethiprole and *perilla* oil were tested individually and in combination for efficacy against 4- to 6-day old adult *Aedes aegypti*. Solutions tested included Solution 1 (0.0005 µg/mosquito of ethiprole), Solution 2 (2% *perilla* oil), and Solution 3 (0.0005 µg/mosquito of ethiprole with 2% *perilla* oil). At 1 hour we obtained 0%, 13%, and 40% knockdown, respectively. At 24 hours we obtained 97%, 0%, and 47% mean mortality, respectively. The $CO_2$ control and acetone standard both had 0% knockdown at 1 hour, and 0% mean mortality at 24 hours. Results are shown in Table 24.

TABLE 24

Efficacy of perilla oil, etofenprox, a combination of both against adult, virgin, female *Aedes aegypti* mosquitoes.

| ACTIVE INGREDIENT | CONCENTRATION | % MORTALITY AFTER 24 HRS | |
|---|---|---|---|
| PERILLA OIL | 2% | 0 | |
| ETOFENPROX | 0.0005 µg | 97 | |
| | | OBS.* | CALC.** |
| PERILLA OIL + ETOFENPROX | 2% + 0.0005 µg | 47[‡] | 97 |

*Obs. = observed efficacy
**Calc. = efficacy calculated using Colby (1967) formula
[‡]Since the calculated insecticidal kill rate exceeds the observed value, then the action of the combination is antagonistic.

Example 35

Various *perilla* oil components, perillaldehyde analogs, and insecticides were tested for efficacy against mosquitoes as detailed in Reference Example 1 with results shown in Tables 25-35.

TABLE 25

Efficacy of perilla oil, clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Perilla Oil | 1% | 3 | |
| Clothianidin | 0.005 µg | 7 | |
| | | OBS.* | CALC.** |
| Perilla Oil + Clothianidin | 1% + 0.005 µg | 77[‡] | 9.79 |

*Obs. = observed efficacy
**Calc. = efficacy calculated using Colby (1967) formula
[‡]Since the actual insecticidal kill rate exceeds the calculated value, then the action of the combination is super-additive or a synergistic effect is present.

TABLE 26

Efficacy of perillaldehyde, clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Perillaldehyde | 2% | 30 | |
| Clothianidin | 0.025 µg | 40 | |
| | | OBS.* | CALC.** |
| Perillaldehyde + Clothianidin | 2% + 0.025 µg | 97‡ | 58 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 27

Efficacy of β-caryophyllene, clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| β-caryophyllene | 3% | 10 | |
| Clothianidin | 0.01 µg | 50 | |
| | | OBS.* | CALC.** |
| β-caryophyllene + Clothianidin | 3% + 0.01 µg | 90‡ | 55 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 28

Efficacy of farnesene, clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Farnesene | 3% | 3 | |
| Clothianidin | 0.01 µg | 43 | |
| | | OBS.* | CALC.** |
| Farnesene + Clothianidin | 3% + 0.01 µg | 93‡ | 44.71 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 29

Efficacy of linolenic acid, clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Linolenic Acid | 3% | 13 | |
| Clothianidin | 0.01 µg | 43 | |
| | | OBS.* | CALC.** |
| Linolenic Acid + Clothianidin | 3% + 0.01 µg | 80‡ | 49.11 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 30

Efficacy of limonene, clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Limonene | 5% | 27 | |
| Clothianidin | 0.025 µg | 20 | |
| | | OBS.* | CALC.** |
| Limonene + Clothianidin | 5% + 0.025 µg | ‡ 100 | 41.6 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 31

Efficacy of (R)-(−)-carvone, clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (R)-(−)-carvone | 3% | 7 | |
| Clothianidin | 0.025 µg | 20 | |
| | | OBS.* | CALC.** |
| (R)-(−)-carvone + Clothianidin | 3% + 0.025 µg | ‡ 100 | 25.6 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 32

Efficacy of (S)-(+)-carvone, clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(+)-carvone | 3% | 13 | |
| Clothianidin | 0.025 µg | 20 | |
| | | OBS.* | CALC.** |
| (S)-(+)-carvone + Clothianidin | 3% + 0.025 µg | ‡ 97 | 30.4 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 33

Efficacy of (1R)-(−)-myrtenal, clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (1R)-(−)-myrtenal | 2% | 10 | |
| Clothianidin | 0.025 µg | 20 | |
| | | OBS.* | CALC.** |
| (1R)-(−)-myrtenal + Clothianidin | 2% + 0.025 µg | ‡ 93 | 28 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 34

Efficacy of (S)-(−)-perillyl alcohol, clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-perillyl alcohol | 2% | 70 | |
| Clothianidin | 0.025 μg | 20 | |
| | | OBS.* | CALC.** |
| (S)-(−)-perillyl alcohol + Clothianidin | 2% + 0.025 μg | ‡100 | 76 |

*Obs = observed efficacy
**Calc. = efficacy calculated using Colby (1967) formula
‡ Since the actual insecticidal kill rate exceeds the calculated value, then the action of the combination is super-additive or a synergistic effect is present.

TABLE 35

Efficacy of (S)-(−)-Perillic acid, clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillic acid | 1% | 7 | |
| Clothianidin | 0.025 μg | 20 | |
| | | OBS.* | CALC.** |
| (S)-(−)-Perillic acid + Clothianidin | 1% + 0.025 μg | ‡57 | 25.6 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

Example 36

Various *perilla* oil components, perillaldehyde analogs, and insecticides were tested for efficacy against mosquitoes as detailed in Reference Example 1 with results shown in Tables 36-46.

TABLE 36

Efficacy of D-limonene, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| D-limonene | 5% | 13 | |
| Dinotefuran | 0.06 μg | 60 | |
| | | OBS.* | CALC.** |
| D-limonene + Dinotefuran | 5% + 0.06 μg | 97‡ | 65.2 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 37

Efficacy of (S)-(+)-Carvone, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(+)-Carvone | 3% | 33 | |
| Dinotefuran | 0.06 μg | 60 | |
| | | OBS.* | CALC.** |
| (S)-(+)-Carvone + Dinotefuran | 3% + 0.06 μg | 100‡ | 73.2 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 38

Efficacy of (S)-(+)-Carvone, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(+)-Carvone | 3% | 37 | |
| Dinotefuran | 0.01 μg | 3 | |
| | | OBS.* | CALC.** |
| (S)-(+)-Carvone + Dinotefuran | 3% + 0.01 μg | 100‡ | 38.89 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 39

Efficacy of (R)-(−)-Carvone, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (R)-(−)-Carvone | 3% | 33 | |
| Dinotefuran | 0.01 μg | 3 | |
| | | OBS.* | CALC.** |
| (R)-(−)-Carvone + Dinotefuran | 3% + 0.01 μg | 93‡ | 35.01 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 40

Efficacy of (1R)-(−)-Myrtenal, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (1R)-(−)-Myrtenal | 2% | 57 | |
| Dinotefuran | 0.06 µg | 60 | |
| | | OBS.* | CALC.** |
| (1R)-(−)-Myrtenal + Dinotefuran | 2% + 0.06 µg | 97‡ | 82.8 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 41

Efficacy of (1R)-(−)-Myrtenal, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (1R)-(−)-Myrtenal | 2% | 23 | |
| Dinotefuran | 0.01 µg | 3 | |
| | | OBS.* | CALC.** |
| (1R)-(−)-Myrtenal + Dinotefuran | 2% + 0.01 µg | 70‡ | 25.31 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 42

Efficacy of (S)-(−)-Perillyl alcohol, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillyl alcohol | 2% | 83 | |
| Dinotefuran | 0.06 µg | 60 | |
| | | OBS.* | CALC.** |
| (S)-(−)-Perillyl alcohol + Dinotefuran | 2% + 0.06 µg | 100‡ | 93.2 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 43

Efficacy of (S)-(−)-Perillyl alcohol, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillyl alcohol | 1% | 0 | |
| Dinotefuran | 0.01 µg | 0 | |
| | | OBS.* | CALC.** |
| (S)-(−)-Perillyl alcohol + Dinotefuran | 1% + 0.01 µg | 83‡ | 0 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 44

Efficacy of (S)-(−)-Perillic acid, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillic acid | 1% | 10 | |
| Dinotefuran | 0.06 µg | 60 | |
| | | OBS.* | CALC.** |
| (S)-(−)-Perillic acid + Dinotefuran | 1% + 0.06 µg | 93‡ | 64 |

* Obs. = observed efficacy
** Calc. = efficacy calculated using Colby (1967) formula
‡Since the actual insecticidal kill rate exceeds the calculated value, then the action of the combination is super-additive or a synergistic effect is present.

TABLE 45

Efficacy of 3-methyl-1-cyclohexene-1-carboxaldehyde (3-methyl), Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 3-methyl | 2% | 17 | |
| Dinotefuran | 0.06 µg | 60 | |
| | | OBS.* | CALC.** |
| 3-methyl + Dinotefuran | 2% + 0.06 µg | 100‡ | 66.8 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 46

Efficacy of 3-methyl-1-cyclohexene-1-carboxaldehyde (3-methyl), Dinotefuran, and a combination of both against adult, virgin, female *Aedes aegypti* mosquitoes.

| ACTIVE INGREDIENT | CONCENTRATION | % MORTALITY AFTER 24 HRS |
|---|---|---|
| 3-methyl | 2% | 0 |
| Dinotefuran | 0.01 µg | 0 |

TABLE 46-continued

Efficacy of 3-methyl-1-cyclohexene-1-carboxaldehyde (3-methyl), Dinotefuran, and a combination of both against adult, virgin, female *Aedes aegypti* mosquitoes.

|  |  | OBS.* | CALC.** |
|---|---|---|---|
| 3-methyl + Dinotefuran | 2% + 0.01 µg | 100‡ | 0 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 37

Various *perilla* oil components, perillaldehyde analogs, and insecticides were tested for efficacy against mosquitoes as detailed in Reference Example 1 with results shown in Tables 47-58.

TABLE 47

Efficacy of Perilla oil, Thiamethoxam, and a combination of both against adult, virgin, female *Aedes aegypti* mosquitoes.

| ACTIVE INGREDIENT | CONCENTRATION | % MORTALITY AFTER 24 HRS |
|---|---|---|
| Perilla oil | 2% | 23 |
| Thiamethoxam | 0.0075 µg | 27 |

|  |  | OBS.* | CALC.** |
|---|---|---|---|
| Perilla oil + Thiamethoxam | 2% + 0.0075 µg | 100‡ | 43.79 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 48

Efficacy of Perilla oil, Thiamethoxam, and a combination of both against adult, virgin, female *Aedes aegypti* mosquitoes.

| ACTIVE INGREDIENT | CONCENTRATION | % MORTALITY AFTER 24 HRS |
|---|---|---|
| Perilla oil | 2% | 23 |
| Thiamethoxam | 0.0025 µg | 3 |

|  |  | OBS.* | CALC.** |
|---|---|---|---|
| Perilla oil + Thiamethoxam | 2% + 0.0025 µg | 90‡ | 25.31 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 49

Efficacy of Farnasene, Thiamethoxam, and a combination of both against adult, virgin, female *Aedes aegypti* mosquitoes.

| ACTIVE INGREDIENT | CONCENTRATION | % MORTALITY AFTER 24 HRS |
|---|---|---|
| Farnasene | 3% | 3 |
| Thiamethoxam | 0.0075 µg | 37 |

|  |  | OBS.* | CALC.** |
|---|---|---|---|
| Farnasene + Thiamethoxam | 3% + 0.0075 µg | 100‡ | 38.89 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 50

Efficacy of (S)-(−)-Perillaldehyde ((S)-Perillaldehyde), Thiamethoxam, and a combination of both against adult, virgin, female *Aedes aegypti* mosquitoes.

| ACTIVE INGREDIENT | CONCENTRATION | % MORTALITY AFTER 24 HRS |
|---|---|---|
| (S)-Perillaldehyde | 2% | 30 |
| Thiamethoxam | 0.0075 µg | 43 |

|  |  | OBS.* | CALC.** |
|---|---|---|---|
| (S)-Perillaldehyde + Thiamethoxam | 2% + 0.0075 µg | 97‡ | 60.1 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 51

Efficacy of Linolenic acid, Thiamethoxam, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Linolenic acid | 3% | 13 | |
| Thiamethoxam | 0.0075 µg | 37 | |
| | | OBS.* | CALC.** |
| Linolenic acid + Thiamethoxam | 3% + 0.0075 µg | 100‡ | 45.19 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 52

Efficacy of β-Caryophyllene, Thiamethoxam, and a combination of both against adult, virgin, female *Aedes aegypti* mosquitoes.

| ACTIVE INGREDIENT | CONCENTRATION | % MORTALITY AFTER 24 HRS | |
|---|---|---|---|
| β-Caryophyllene | 3% | 10 | |
| Thiamethoxam | 0.0075 µg | 30 | |
| | | OBS.* | CALC.** |
| β-Caryophyllene + Thiamethoxam | 3% + 0.0075 µg | 90‡ | 37 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 53

Efficacy of D-limonene, Thiamethoxam, and a combination of both against adult, virgin, female *Aedes aegypti* mosquitoes.

| ACTIVE INGREDIENT | CONCENTRATION | % MORTALITY AFTER 24 HRS | |
|---|---|---|---|
| D-limonene | 5% | 0 | |
| Thiamethoxam | 0.0075 µg | 23 | |
| | | OBS.* | CALC.** |
| D-limonene + Thiamethoxam | 5% + 0.0075 µg | 87‡ | 23 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 54

Efficacy of (R)-(−)-Carvone, Thiamethoxam, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (R)-(−)-Carvone | 3% | 0 | |
| Thiamethoxam | 0.0075 µg | 23 | |
| | | OBS.* | CALC.** |
| (R)-(−)-Carvone + Thiamethoxam | 3% + 0.0075 µg | 57‡ | 23 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 55

Efficacy of (S)-(+)-Carvone, Thiamethoxam, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(+)-Carvone | 3% | 3 | |
| Thiamethoxam | 0.0075 µg | 23 | |
| | | OBS.* | CALC.** |
| (S)-(+)-Carvone + Thiamethoxam | 3% + 0.0075 µg | 97‡ | 25.31 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 56

Efficacy of (1R)-(−)-Myrtenal, Thiamethoxam, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (1R)-(−)-Myrtenal | 2% | 0 | |
| Thiamethoxam | 0.0075 µg | 23 | |
| | | OBS.* | CALC.** |
| (1R)-(−)-Myrtenal + Thiamethoxam | 2% + 0.0075 µg | 77‡ | 23 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 57

Efficacy of (S)-(−)-Perillyl alcohol ((S)-Perillyl alcohol), Thiamethoxam, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-Perillyl alcohol | 2% | 33 | |
| Thiamethoxam | 0.0075 µg | 3 | |
| | | OBS.* | CALC.** |
| (S)-Perillyl alcohol + Thiamethoxam | 2% + 0.0075 µg | 77‡ | 35.01 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 58

Efficacy of (S)-(−)-Perillic acid, Thiamethoxam, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillic acid | 1% | 13 | |
| Thiamethoxam | 0.0075 µg | 3 | |
| | | OBS.* | CALC.** |
| (S)-(−)-Perillic acid + Thiamethoxam | 1% + 0.0075 µg | 20‡ | 15.61 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 38

Various *perilla* oil components, perillaldehyde analogs, and insecticides were tested for efficacy against mosquitoes as detailed in Reference Example 1 with results shown in Tables 59-68.

TABLE 59

Efficacy of perilla oil, imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Perilla Oil | 1% $_T$ | 3 | |
| Imidacloprid | 0.005 μg | 60 | |
| | | OBS.* | CALC.** |
| Perilla Oil + Imidacloprid | 1% + 0.005 μg | 87 $_\ddagger$ | 61.2 |
| Perilla Oil | 2% | 3 | |
| Imidacloprid | 0.005 μg | 60 | |
| | | OBS.* | CALC.** |
| Perilla Oil + Imidacloprid | 2% + 0.005 μg | 100 $_\ddagger$ | 61.2 |

$_T$ 3% efficacy was derived from data that underwent probit analysis to predict lethal dose values from topical application bioassay.

*Obs. = observed efficacy

**Calc. = efficacy calculated using Colby (1967) formula $_\ddagger$ Since the actual insecticidal kill rate exceeds the calculated value, then the action of the combination is super-additive or a synergistic effect is present.

TABLE 60

Efficacy of β-caryophyllene, imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| β-caryophyllene | 3% | 50 | |
| Imidacloprid | 0.005 μg | 50 | |
| | | OBS.* | CALC.** |
| β-caryophyllene + Imidacloprid | 3% + 0.005 μg | 100$_\ddagger$ | 75 |

*Obs. = observed efficacy

**Calc. = efficacy calculated using Colby (1967) formula $_\ddagger$ Since the actual insecticidal kill rate exceeds the calculated value, then the action of the combination is super-additive or a synergistic effect is present.

TABLE 61

Efficacy of farnesene, imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Farnesene | 3% | 7 | |
| Imidacloprid | 0.005 μg | 53 | |
| | | OBS.* | CALC.** |
| Farnesene + Imidacloprid | 3% + 0.005 μg | 100$_\ddagger$ | 56.29 |

*Obs. = observed efficacy

**Calc. = efficacy calculated using Colby (1967) formula $_\ddagger$ Since the actual insecticidal kill rate exceeds the calculated value, then the action of the combination is super-additive or a synergistic effect is present.

TABLE 62

Efficacy of linolenic acid, imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Linolenic Acid | 3% | 13 | |
| Imidacloprid | 0.005 µg | 53 | |
| | | OBS.* | CALC.** |
| Linolenic Acid + Imidacloprid | 3% + 0.005 µg | 100‡ | 59.11 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 63

Efficacy of D-limonene, Imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| D-limonene | 5% | 23 | |
| Imidacloprid | 0.005 µg | 43 | |
| | | OBS.* | CALC.** |
| D-limonene + Imidacloprid | 5% + 0.005 µg | 97‡ | 56.11 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 64

Efficacy of (R)-(−)-Carvone, Imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (R)-(−)-Carvone | 3% | 23 | |
| Imidacloprid | 0.005 µg | 43 | |
| | | OBS.* | CALC.** |
| (R)-(−)-Carvone + Imidacloprid | 3% + 0.005 µg | 93‡ | 56.11 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 65

Efficacy of (S)-(+)-Carvone, Imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(+)-Carvone | 3% | 20 | |
| Imidacloprid | 0.005 µg | 53 | |
| | | OBS.* | CALC.** |
| (S)-(+)-Carvone + Imidacloprid | 3% + 0.005 µg | 100‡ | 62.4 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 66

Efficacy of (1R)-(−)-Myrtenal, Imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (1R)-(−)-Myrtenal | 2% | 47 | |
| Imidacloprid | 0.005 µg | 53 | |
| | | OBS.* | CALC.** |
| (1R)-(−)-Myrtenal + Imidacloprid | 2% + 0.005 µg | 90‡ | 75.09 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 67

Efficacy of (S)-(−)-Perillyl alcohol, Imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillyl alcohol | 2% | 47 | |
| Imidacloprid | 0.005 µg | 53 | |
| | | OBS.* | CALC.** |
| (S)-(−)-Perillyl alcohol + Imidacloprid | 2% + 0.005 µg | 97‡ | 75.09 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 68

Efficacy of (S)-(−)-Perillic acid, Imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillic acid | 1% | 13 | |
| Imidacloprid | 0.005 µg | 53 | |
| | | OBS.* | CALC.** |
| (S)-(−)-Perillic acid + Imidacloprid | 1% + 0.005 µg | 83‡ | 59.11 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 39

*Perilla* oil and various *perilla* oil components, various perillaldehyde analogs, and insecticides were tested against mosquitoes as detailed in Reference Example 1 with results how in Tables 69-75.

TABLE 69

Efficacy of Perilla oil, Permethrin, and a combination of both against adult, virgin, female *Aedes aegypti* mosquitoes.

| ACTIVE INGREDIENT | CONCENTRATION | % MORTALITY AFTER 24 HRS |
|---|---|---|
| Perilla oil | 2% | 3 |
| Permethrin | 0.0003 µg | 27 |

TABLE 69-continued

Efficacy of Perilla oil, Permethrin, and a combination of both against adult, virgin, female *Aedes aegypti* mosquitoes.

|  |  | OBS.* | CALC.** |
|---|---|---|---|
| Perilla oil + Permethrin | 2% + 0.0003 µg | 53‡ | 29.19 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 70

Efficacy of D-limonene, Permethrin, and a combination of both against adult, virgin, female *Aedes aegypti* mosquitoes.

| ACTIVE INGREDIENT | CONCENTRATION | % MORTALITY AFTER 24 HRS |
|---|---|---|
| D-limonene | 5% | 47 |
| Permethrin | 0.0003 µg | 17 |

|  |  | OBS.* | CALC.** |
|---|---|---|---|
| D-limonene + Permethrin | 5% + 0.0003 µg | 53‡ | 56.01 |

*Obs. = observed efficacy

**Calc. = efficacy calculated using Colby (1967) formula

‡Since the actual insecticidal kill rate does not exceed the calculated value, then the action of the combination is not super-additive or synergistic.

TABLE 71

Efficacy of (R)-(−)-Carvone, Permethrin, and a combination of both against adult, virgin, female *Aedes aegypti* mosquitoes.

| ACTIVE INGREDIENT | CONCENTRATION | % MORTALITY AFTER 24 HRS |
|---|---|---|
| (R)-(−)-Carvone | 3% | 33 |
| Permethrin | 0.0003 µg | 17 |

|  |  | OBS.* | CALC.** |
|---|---|---|---|
| (R)-(−)-Carvone + Permethrin | 3% + 0.0003 µg | 60‡ | 44.39 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 72

Efficacy of (S)-(+)-Carvone, Permethrin, and a combination of both against adult, virgin, female *Aedes aegypti* mosquitoes.

| ACTIVE INGREDIENT | CONCENTRATION | % MORTALITY AFTER 24 HRS |
|---|---|---|
| (S)-(+)-Carvone | 3% | 20 |
| Permethrin | 0.0003 µg | 17 |

|  |  | OBS.* | CALC.** |
|---|---|---|---|
| (S)-(+)-Carvone + Permethrin | 3% + 0.0003 µg | 67‡ | 33.6 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 73

Efficacy of (1R)-(−)-Myrtenal, Permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (1R)-(−)-Myrtenal | 2% | 47 | |
| Permethrin | 0.0003 µg | 17 | |
| | | OBS.* | CALC.** |
| (1R)-(−)-Myrtenal + Permethrin | 2% + 0.0003 µg | 43‡ | 56.01 |

*Obs. = observed efficacy
**Calc. = efficacy calculated using Colby (1967) formula
‡Since the actual insecticidal kill rate does not exceed the calculated value, then the action of the combination is not super-additive or synergistic.

TABLE 74

Efficacy of (S)-(−)-Perillyl alcohol, Permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillyl alcohol | 2% | 47 | |
| Permethrin | 0.0003 µg | 17 | |
| | | OBS.* | CALC.** |
| (S)-(−)-Perillyl alcohol + Permethrin | 2% + 0.0003 µg | 50‡ | 56.01 |

*Obs. = observed efficacy
**Calc. = efficacy calculated using Colby (1967) formula
‡Since the actual insecticidal kill rate does not exceed the calculated value, then the action of the combination is not super-additive or synergistic.

TABLE 75

Efficacy of (S)-(−)-Perillic acid, Permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillic acid | 1% | 13 | |
| Permethrin | 0.0003 µg | 17 | |
| | | OBS.* | CALC.** |
| (S)-(−)-Perillic acid + Permethrin | 1% + 0.0003 µg | 100‡ | 27.79 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 40

*Perilla* oil and various *perilla* oil components, various perillaldehyde analogs, and insecticides were tested against mosquitoes as detailed in Reference Example 1 with results show in Tables 76-86.

TABLE 76

Efficacy of Perilla oil, Sumithrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Perilla oil | 3% | 20 | |
| Sumithrin | 0.0007 µg | 27 | |
| | | OBS.* | CALC.** |
| Perilla oil + Sumithrin | 3% + 0.0007 µg | 57‡ | 41.6 |
| Perilla oil | 4% | 17 | |
| Sumithrin | 0.0007 µg | 27 | |
| | | OBS.* | CALC.** |
| Perilla oil + Sumithrin | 4% + 0.0007 µg | 80‡ | 39.41 |
| Perilla oil | 5% | 37 | |
| Sumithrin | 0.0007 µg | 27 | |

TABLE 76-continued

Efficacy of Perilla oil, Sumithrin, and a combination of both against adult, virgin, female *Aedes aegypti* mosquitoes.

|  |  | OBS.* | CALC.** |
|---|---|---|---|
| Perilla oil + Sumithrin | 5% + 0.0007 μg | 77 ‡ | 54.01 |
| Perilla oil | 6% |  | 50 |
| Sumithrin | 0.0007 μg |  | 27 |

|  |  | OBS.* | CALC.** |
|---|---|---|---|
| Perilla oil + Sumithrin | 6% + 0.0007 μg | 93 ‡ | 63.5 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 77

Efficacy of Perillaldehyde, Sumithrin, and a combination of both against adult, virgin, female *Aedes aegypti* mosquitoes.

| ACTIVE INGREDIENT | CONCENTRATION | % MORTALITY AFTER 24 HRS |
|---|---|---|
| Perillaldehyde | 2% | 57 |
| Sumithrin | 0.0007 μg | 40 |

|  |  | OBS.* | CALC.** |
|---|---|---|---|
| Perillaldehyde + Sumithrin | 2% + 0.0007 μg | 70 ‡ | 74.2 |

*Obs. = observed efficacy
**Calc. = efficacy calculated using Colby (1967) formula
‡ Since the actual insecticidal kill rate does not exceed the calculated value, then the action of the combination is not super-additive or synergistic.

TABLE 78

Efficacy of Farnesene, Sumithrin, and a combination of both against adult, virgin, female *Aedes aegypti* mosquitoes.

| ACTIVE INGREDIENT | CONCENTRATION | % MORTALITY AFTER 24 HRS |
|---|---|---|
| Farnesene | 3% | 7 |
| Sumithrin | 0.0007 μg | 40 |

|  |  | OBS.* | CALC.** |
|---|---|---|---|
| Perillaldehyde + Sumithrin | 3% + 0.0007 μg | 80 ‡ | 44.2 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 79

Efficacy of Linolenic acid, Sumithrin, and a combination of both against adult, virgin, female *Aedes aegypti* mosquitoes.

| ACTIVE INGREDIENT | CONCENTRATION | % MORTALITY AFTER 24 HRS |
|---|---|---|
| Linolenic acid | 3% | 0 |
| Sumithrin | 0.0007 μg | 40 |

|  |  | OBS.* | CALC.** |
|---|---|---|---|
| Linolenic acid + Sumithrin | 3% + 0.0007 μg | 13 ‡ | 40 |

*Obs. = observed efficacy
**Calc. = efficacy calculated using Colby (1967) formula
‡ Since the actual insecticidal kill rate does not exceed the calculated value, then the action of the combination is not super-additive or synergistic.

TABLE 80

Efficacy of β-Caryophyllene, Sumithrin, and a combination of both against adult, virgin, female *Aedes aegypti* mosquitoes.

| ACTIVE INGREDIENT | CONCENTRATION | % MORTALITY AFTER 24 HRS |
|---|---|---|
| β-Caryophyllene | 3% | 0 |
| Sumithrin | 0.0007 μg | 40 |

|  |  | OBS.* | CALC.** |
|---|---|---|---|
| β-Caryophyllene + Sumithrin | 3% + 0.0007 μg | 83 ‡ | 40 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 81

Efficacy of D-limonene, Sumithrin, and a combination of both against adult, virgin, female *Aedes aegypti* mosquitoes.

| ACTIVE INGREDIENT | CONCENTRATION | % MORTALITY AFTER 24 HRS |
|---|---|---|
| D-limonene | 5% | 57 |
| Sumithrin | 0.0007 μg | 40 |

|  |  | OBS.* | CALC.** |
|---|---|---|---|
| D-limonene + Sumithrin | 5% + 0.0007 μg | 93 ‡ | 74.2 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 82

Efficacy of (R)-(−)-Carvone, Sumithrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (R)-(−)-Carvone | 3% | 20 | |
| Sumithrin | 0.0007 µg | 40 | |
| | | OBS.* | CALC.** |
| (R)-(−)-Carvone + Sumithrin | 3% + 0.0007 µg | 73‡ | 52 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 83

Efficacy of (S)-(+)-Carvone, Sumithrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(+)-Carvone | 3% | 10 | |
| Sumithrin | 0.0007 µg | 40 | |
| | | OBS.* | CALC.** |
| (S)-(+)-Carvone + Sumithrin | 3% + 0.0007 µg | 97‡ | 46 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 84

Efficacy of (1R)-(−)-Myrtenal, Sumithrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (1R)-(−)-Myrtenal | 2% | 3 | |
| Sumithrin | 0.0007 µg | 40 | |
| | | OBS.* | CALC.** |
| (1R)-(−)-Myrtenal + Sumithrin | 2% + 0.0007 µg | 67‡ | 41.8 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 85

Efficacy of (S)-(−)-Perillyl alcohol, Sumithrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillyl alcohol | 2% | 70 | |
| Sumithrin | 0.0007 µg | 40 | |
| | | OBS.* | CALC.** |
| (S)-(−)-Perillyl alcohol + Sumithrin | 2% + 0.0007 µg | 77‡ | 82 |

*Obs. = observed efficacy
**Calc. = efficacy calculated using Colby (1967) formula
‡Since the actual insecticidal kill rate does not exceed the calculated value, then the action of the combination is not super-additive or synergistic.

TABLE 86

Efficacy of (S)-(−)-Perillic acid, Sumithrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillic acid | 1% | 87 | |
| Sumithrin | 0.0007 µg | 40 | |
| | | OBS.* | CALC.** |
| (S)-(−)-Perillic acid + Sumithrin | 1% + 0.0007 µg | 27‡ | 92.2 |

*Obs. = observed efficacy
**Calc. = efficacy calculated using Colby (1967) formula
‡Since the actual insecticidal kill rate does not exceed the calculated value, then the action of the combination is not super-additive or synergistic.

Example 41

*Perilla* oil and various *perilla* oil components, various perillaldehyde analogs, and insecticides were tested against mosquitoes as detailed in Reference Example 1 with results show in Tables 87-97.

TABLE 87

Efficacy of Perilla oil, Prallethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Perilla oil | 1% | 3 | |
| Prallethrin | 0.00075 µg | 37 | |
| | | OBS.* | CALC.** |
| Perilla oil + Prallethrin | 1% + 0.00075 µg | 97‡ | 38.89 |
| Perilla oil | 2% | 13 | |
| Prallethrin | 0.00075 µg | 37 | |
| | | OBS.* | CALC.** |
| Perilla oil + Prallethrin | 2% + 0.00075 µg | 100‡ | 45.19 |
| Perilla oil | 3% | 13 | |
| Prallethrin | 0.00075 µg | 37 | |
| | | OBS.* | CALC.** |
| Perilla oil + Prallethrin | 3% + 0.00075 µg | 100‡ | 45.19 |
| Perilla oil | 4% | 40 | |
| Prallethrin | 0.00075 µg | 37 | |

TABLE 87-continued

Efficacy of Perilla oil, Prallethrin, and a combination of both against adult, virgin, female *Aedes aegypti* mosquitoes.

|  |  | OBS.* | CALC.** |
|---|---|---|---|
| Perilla oil + Prallethrin | 4% + 0.00075 µg | 100 ‡ | 62.2 |
| Perilla oil | 5% |  | 63 |
| Prallethrin | 0.00075 µg |  | 37 |

|  |  | OBS.* | CALC.** |
|---|---|---|---|
| Perilla oil + Prallethrin | 5% + 0.00075 µg | 100 ‡ | 76.69 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 88

Efficacy of Perillaldehyde, Prallethrin, and a combination of both against adult, virgin, female *Aedes aegypti* mosquitoes.

| ACTIVE INGREDIENT | CONCENTRATION | % MORTALITY AFTER 24 HRS |
|---|---|---|
| Perillaldehyde | 1% | 3 |
| Prallethrin | 0.00075 µg | 37 |

|  |  | OBS.* | CALC.** |
|---|---|---|---|
| Perillaldehyde + Prallethrin | 1% + 0.00075 µg | 47 ‡ | 38.89 |
| Perillaldehyde | 2% |  | 60 |
| Prallethrin | 0.00075 µg |  | 37 |

|  |  | OBS.* | CALC.** |
|---|---|---|---|
| Perillaldehyde + Prallethrin | 2% + 0.00075 µg | 77 ‡ | 74.8 |
| Perillaldehyde | 3% |  | 97 |
| Prallethrin | 0.00075 µg |  | 37 |

TABLE 88-continued

Efficacy of Perillaldehyde, Prallethrin, and a combination of both against adult, virgin, female *Aedes aegypti* mosquitoes.

|  |  | OBS.* | CALC.** |
|---|---|---|---|
| Perillaldehyde + Prallethrin | 3% + 0.00075 µg | 90 § | 98.11 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

§ Since the actual insecticidal kill rate does not exceed the calculated value, then the action of the combination is not super-additive or synergistic.

TABLE 89

Efficacy of Farnasene, Prallethrin, and a combination of both against adult, virgin, female *Aedes aegypti* mosquitoes.

| ACTIVE INGREDIENT | CONCENTRATION | % MORTALITY AFTER 24 HRS |
|---|---|---|
| Farnasene | 3% | 7 |
| Prallethrin | 0.00075 µg | 20 |

|  |  | OBS.* | CALC.** |
|---|---|---|---|
| Farnasene + Prallethrin | 3% + 0.00075 µg | 90 ‡ | 25.6 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 90

Efficacy of Linolenic acid, Prallethrin, and a combination of both against adult, virgin, female *Aedes aegypti* mosquitoes.

| ACTIVE INGREDIENT | CONCENTRATION | % MORTALITY AFTER 24 HRS |
|---|---|---|
| Linolenic acid | 3% | 0 |
| Prallethrin | 0.00075 µg | 20 |

|  |  | OBS.* | CALC.** |
|---|---|---|---|
| Linolenic acid + Prallethrin | 3% + 0.00075 µg | 7 ‡ | 20 |

*Obs. = observed efficacy

**Calc. = efficacy calculated using Colby (1967) formula

‡ Since the actual insecticidal kill rate does not exceed the calculated value, then the action of the combination is not super-additive or synergistic.

TABLE 91

Efficacy of β-Caryophyllene, Prallethrin, and a combination of both against adult, virgin, female *Aedes aegypti* mosquitoes.

| ACTIVE INGREDIENT | CONCENTRATION | % MORTALITY AFTER 24 HRS |
|---|---|---|
| β-Caryophyllene | 3% | 0 |
| Prallethrin | 0.00075 µg | 20 |

|  |  | OBS.* | CALC.** |
|---|---|---|---|
| β-Caryophyllene + Prallethrin | 3% + 0.00075 µg | 33 ‡ | 20 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 92

Efficacy of D-limonene, Prallethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| D-limonene | 5% | 7 | |
| Prallethrin | 0.00075 µg | 20 | |
| | | OBS.* | CALC.** |
| D-limonene + Prallethrin | 5% + 0.00075 µg | 77 ‡ | 25.6 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 93

Efficacy of (R)-(−)-Carvone, Prallethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (R)-(−)-Carvone | 3% | 3 | |
| Prallethrin | 0.00075 µg | 20 | |
| | | OBS.* | CALC.** |
| (R)-(−)-Carvone + Prallethrin | 3% + 0.00075 µg | 70 ‡ | 22.4 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 94

Efficacy of (S)-(+)-Carvone, Prallethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(+)-Carvone | 3% | 10 | |
| Prallethrin | 0.00075 µg | 20 | |
| | | OBS.* | CALC.** |
| (S)-(+)-Carvone + Prallethrin | 3% + 0.00075 µg | 73 ‡ | 28 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 95

Efficacy of (1R)-(−)-Myrtenal, Prallethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (1R)-(−)-Myrtenal | 2% | 0 | |
| Prallethrin | 0.00075 µg | 20 | |
| | | OBS.* | CALC.** |
| (1R)-(−)-Myrtenal + Prallethrin | 2% + 0.00075 µg | 3 ‡ | 20 |

*Obs. = observed efficacy
**Calc. = efficacy calculated using Colby (1967) formula
‡ Since the actual insecticidal kill rate does not exceed the calculated value, then the action of the combination is not super-additive or synergistic.

TABLE 96

Efficacy of (S)-(−)-Perillyl alcohol, Prallethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillyl alcohol | 2% | 3 | |
| Prallethrin | 0.00075 µg | 20 | |
| | | OBS.* | CALC.** |
| (S)-(−)-Perillyl alcohol + Prallethrin | 2% + 0.00075 µg | 87 ‡ | 22.4 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 97

Efficacy of (S)-(−)-Perillic acid, Prallethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillic acid | 1% | 7 | |
| Prallethrin | 0.00075 µg | 20 | |
| | | OBS.* | CALC.** |
| (S)-(−)-Perillic acid + Prallethrin | 1% + 0.00075 µg | 93 ‡ | 25.6 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

Example 42

Various perillaldehyde analogs, and insecticides were tested against mosquitoes as detailed in Reference Example 1 with results show in Tables 98-103.

TABLE 98

Efficacy of D-limonene, Etofenprox, and a combination of both against adult, virgin, female *Aedes aegypti* mosquitoes.

| ACTIVE INGREDIENT | CONCENTRATION | % MORTALITY AFTER 24 HRS | |
|---|---|---|---|
| D-limonene | 5% | 13 | |
| Etofenprox | 0.002 µg | 37 | |
| | | OBS.* | CALC.** |
| D-limonene + Etofenprox | 5% + 0.002 µg | 93 ‡ | 45.19 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 99

Efficacy of (R)-(−)-Carvone, Etofenprox, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (R)-(−)-Carvone | 3% | 13 | |
| Etofenprox | 0.002 µg | 37 | |
| | | OBS.* | CALC.** |
| (R)-(−)-Carvone + Etofenprox | 3% + 0.002 µg | 90 ‡ | 45.19 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 100

Efficacy of (S)-(+)-Carvone, Etofenprox, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(+)-Carvone | 3% | 7 | |
| Etofenprox | 0.002 µg | 37 | |
| | | OBS.* | CALC.** |
| (S)-(+)-Carvone + Etofenprox | 3% + 0.002 µg | 70 ‡ | 41.41 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 101

Efficacy of (1R)-(−)-Myrtenal, Etofenprox, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (1R)-(−)-Myrtenal | 2% | 43 | |
| Etofenprox | 0.002 µg | 37 | |
| | | OBS.* | CALC.** |
| (1R)-(−)-Myrtenal + Etofenprox | 2% + 0.002 µg | 97 ‡ | 64.09 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 102

Efficacy of (S)-(−)-Perillyl alcohol, Etofenprox, and a combination of both against adult, virgin, female *Aedes aegypti* mosquitoes.

| ACTIVE INGREDIENT | CONCENTRATION | % MORTALITY AFTER 24 HRS |
|---|---|---|
| (S)-(−)-Perillyl alcohol | 2% | 80 |
| Etofenprox | 0.002 µg | 37 |

TABLE 102-continued

Efficacy of (S)-(−)-Perillyl alcohol, Etofenprox, and a combination of both against adult, virgin, female Aedes aegypti mosquitoes.

|  |  | OBS.* | CALC.** |
|---|---|---|---|
| (S)-(−)-Perillyl alcohol + Etofenprox | 2% + 0.002 μg | 100 ‡ | 87.4 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 103

Efficacy of (S)-(−)-Perillic acid, Etofenprox, and a combination of both against adult, virgin, female Aedes aegypti mosquitoes.

| ACTIVE INGREDIENT | CONCENTRATION | % MORTALITY AFTER 24 HRS |
|---|---|---|
| (S)-(−)-Perillic acid | 1% | 63 |
| Etofenprox | 0.002 μg | 37 |

|  |  | OBS.* | CALC.** |
|---|---|---|---|
| (S)-(−)-Perillic acid + Etofenprox | 1% + 0.002 μg | 93 ‡ | 76.69 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

Example 43

Perilla oil and various perillaldehyde analogs, and insecticides were tested against mosquitoes as detailed in Reference Example 1 with results show in Tables 104-110.

TABLE 104

Efficacy of Perilla oil, Pyrethrins, and a combination of both against adult, virgin, female Aedes aegypti mosquitoes.

| ACTIVE INGREDIENT | CONCENTRATION | % MORTALITY AFTER 24 HRS |
|---|---|---|
| Perilla oil | 1% | 3 |
| Pyrethrins | 0.0015 μg | 30 |

|  |  | OBS.* | CALC.** |
|---|---|---|---|
| Perilla oil + Pyrethrins | 1% + 0.0015 μg | 60 ‡ | 32.1 |
| Perilla oil | 2% | 10 |  |
| Pyrethrins | 0.0015 μg | 30 |  |

|  |  | OBS.* | CALC.** |
|---|---|---|---|
| Perilla oil + Pyrethrins | 2% + 0.0015 μg | 83 ‡ | 37 |
| Perilla oil | 3% | 23 |  |
| Pyrethrins | 0.0015 μg | 30 |  |

|  |  | OBS.* | CALC.** |
|---|---|---|---|
| Perilla oil + Pyrethrins | 3% + 0.0015 μg | 83 ‡ | 46.1 |
| Perilla oil | 4% | 53 |  |
| Pyrethrins | 0.0015 μg | 30 |  |

TABLE 104-continued

Efficacy of Perilla oil, Pyrethrins, and a combination of both against adult, virgin, female Aedes aegypti mosquitoes.

|  |  | OBS.* | CALC.** |
|---|---|---|---|
| Perilla oil + Pyrethrins | 4% + 0.0015 μg | 90 ‡ | 67.1 |
| Perilla oil | 5% | 70 |  |
| Pyrethrins | 0.0015 μg | 30 |  |

|  |  | OBS.* | CALC.** |
|---|---|---|---|
| Perilla oil + Pyrethrins | 5% + 0.0015 μg | 93 ‡ | 79 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 105

Efficacy of D-limonene, Pyrethrins, and a combination of both against adult, virgin, female Aedes aegypti mosquitoes.

| ACTIVE INGREDIENT | CONCENTRATION | % MORTALITY AFTER 24 HRS |
|---|---|---|
| D-limonene | 5% | 50 |
| Pyrethrins | 0.0015 μg | 53 |

|  |  | OBS.* | CALC.** |
|---|---|---|---|
| D-limonene + Pyrethrins | 5% + 0.0015 μg | 100 ‡ | 76.5 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 106

Efficacy of (R)-(−)-Carvone, Pyrethrins, and a combination of both against adult, virgin, female Aedes aegypti mosquitoes.

| ACTIVE INGREDIENT | CONCENTRATION | % MORTALITY AFTER 24 HRS |
|---|---|---|
| (R)-(−)-Carvone | 3% | 10 |
| Pyrethrins | 0.0015 μg | 53 |

|  |  | OBS.* | CALC.** |
|---|---|---|---|
| (R)-(−)-Carvone + Pyrethrins | 3% + 0.0015 μg | 83 ‡ | 57.7 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 107

Efficacy of (S)-(+)-Carvone, Pyrethrins, and a combination of both against adult, virgin, female Aedes aegypti mosquitoes.

| ACTIVE INGREDIENT | CONCENTRATION | % MORTALITY AFTER 24 HRS |
|---|---|---|
| (S)-(+)-Carvone | 3% | 17 |
| Pyrethrins | 0.0015 μg | 53 |

|  |  | OBS.* | CALC.** |
|---|---|---|---|
| (S)-(+)-Carvone + Pyrethrins | 3% + 0.0015 μg | 70 ‡ | 60.99 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 108

Efficacy of (1R)-(−)-Myrtenal, Pyrethrins, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (1R)-(−)-Myrtenal | 2% | 10 | |
| Pyrethrins | 0.0015 µg | 53 | |
| | | OBS.* | CALC.** |
| (1R)-(−)-Myrtenal + Pyrethrins | 2% + 0.0015 µg | 77 ‡ | 57.7 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 109

Efficacy of (S)-(−)-Perillyl alcohol, Pyrethrins, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillyl alcohol | 2% | 67 | |
| Pyrethrins | 0.0015 µg | 53 | |
| | | OBS.* | CALC.** |
| (S)-(−)-Perillyl alcohol + Pyrethrins | 2% + 0.0015 µg | 93 ‡ | 84.49 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 110

Efficacy of (S)-(−)-Perillic acid, Pyrethrins, and a combination of both against adult, virgin, female *Aedes aegypti* mosquitoes.

| ACTIVE INGREDIENT | CONCENTRATION | % MORTALITY AFTER 24 HRS | |
|---|---|---|---|
| (S)-(−)-Perillic acid | 1% | 20 | |
| Pyrethrins | 0.0015 µg | 53 | |
| | | OBS.* | CALC.** |
| (S)-(−)-Perillic acid + Pyrethrins | 1% + 0.0015 µg | 93 ‡ | 62.4 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

Example 44

The insecticide spinosad was tested with *perilla* oil and various perillaldehyde analogs against mosquitoes as detailed in Reference Example 1 with results show in Tables 111-115.

TABLE 111

Efficacy of Perilla oil, Spinosad, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Perilla oil | 2% | 3 | |
| Spinosad | 0.02 µg | 33 | |
| | | OBS.* | CALC.** |
| Perilla oil + Spinosad | 2% + 0.02 µg | 43 ‡ | 35.01 |
| Perilla oil | 3% | 7 | |
| Spinosad | 0.02 µg | 33 | |
| | | OBS.* | CALC.** |
| Perilla oil + Spinosad | 3% + 0.02 µg | 93 ‡ | 37.69 |
| Perilla oil | 4% | 3 | |
| Spinosad | 0.02 µg | 33 | |
| | | OBS.* | CALC.** |
| Perilla oil + Spinosad | 4% + 0.02 µg | 93 ‡ | 35.01 |
| Perilla oil | 5% | 40 | |
| Spinosad | 0.02 µg | 33 | |
| | | OBS.* | CALC.** |
| Perilla oil + Spinosad | 5% + 0.02 µg | 97 ‡ | 59.8 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 112

Efficacy of Perillaldehyde, Spinosad, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Perillaldehyde | 1% | 0 | |
| Spinosad | 0.02 μg | 33 | |
| | | OBS.* | CALC.** |
| Perillaldehyde + Spinosad | 1% + 0.02 μg | 7 ‡ | 33 |
| Perillaldehyde | 2% | | 10 |
| Spinosad | 0.02 μg | | 33 |
| | | OBS.* | CALC.** |
| Perillaldehyde + Spinosad | 2% + 0.02 μg | 20 ‡ | 39.7 |
| Perillaldehyde | 3% | | 73 |
| Spinosad | 0.02 μg | | 33 |
| | | OBS.* | CALC.** |
| Perillaldehyde + Spinosad | 3% + 0.02 μg | 63 ‡ | 81.91 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 113

Efficacy of Farnasene, Spinosad, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Farnasene | 3% | 7 | |
| Spinosad | 0.02 μg | 33 | |
| | | OBS.* | CALC.** |
| Farnasene + Spinosad | 3% + 0.02 μg | 40 ‡ | 37.69 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 114

Efficacy of Linolenic acid, Spinosad, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Linolenic acid | 3% | 10 | |
| Spinosad | 0.02 μg | 33 | |
| | | OBS.* | CALC.** |
| Linolenic acid + Spinosad | 3% + 0.02 μg | 43 ‡ | 39.7 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 115

Efficacy of β-Caryophyllene, Spinosad, and a combination of both against adult, virgin, female *Aedes aegypti* mosquitoes.

| ACTIVE INGREDIENT | CONCENTRATION | % MORTALITY AFTER 24 HRS |
|---|---|---|
| β-Caryophyllene | 3% | 7 |
| Spinosad | 0.02 μg | 33 |

TABLE 115-continued

Efficacy of β-Caryophyllene, Spinosad, and a combination of both against adult, virgin, female *Aedes aegypti* mosquitoes.

|   |   | OBS.* | CALC.** |
|---|---|---|---|
| β-Caryophyllene + Spinosad | 3% + 0.02 µg | 77 ‡ | 37.69 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

Example 45

The insecticide dinotefuran was tested with *perilla* oil analogs against mosquitoes as detailed in Reference Example 1 with results show in Tables 116-126.

TABLE 116

Efficacy of Isophorone, Dinotefuran, and a combination of both against adult, virgin, female *Aedes aegypti* mosquitoes.

| ACTIVE INGREDIENT | CONCENTRATION | % MORTALITY AFTER 24 HRS |
|---|---|---|
| Isophorone | 3% | 30 |
| Dinotefuran | 0.06 µg | 37 |

|   |   | OBS.* | CALC.** |
|---|---|---|---|
| Isophorone + Dinotefuran | 3% + 0.06 µg | 97 ‡ | 55.90 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 117

Efficacy of 1-Methyl-1-cyclohexene, Dinotefuran, and a combination of both against adult, virgin, female *Aedes aegypti* mosquitoes.

| ACTIVE INGREDIENT | CONCENTRATION | % MORTALITY AFTER 24 HRS |
|---|---|---|
| 1-Methyl-1-cyclohexene | 3% | 10 |
| Dinotefuran | 0.06 µg | 37 |

|   |   | OBS.* | CALC.** |
|---|---|---|---|
| 1-Methyl-1-cyclohexene + Dinotefuran | 3% + 0.06 µg | 97 ‡ | 43.30 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 118

Efficacy of 1-tert-Butyl-1-cyclohexene, Dinotefuran, and a combination of both against adult, virgin, female *Aedes aegypti* mosquitoes.

| ACTIVE INGREDIENT | CONCENTRATION | % MORTALITY AFTER 24 HRS |
|---|---|---|
| 1-tert-Butyl . . . | 3% | 17 |
| Dinotefuran | 0.06 µg | 37 |

|   |   | OBS.* | CALC.** |
|---|---|---|---|
| 1-tert-Butyl . . . + Dinotefuran | 3% + 0.06 µg | 37 ‡ | 47.71 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 119

Efficacy of 3,5-Dimethyl-2-cyclohexen-1-one, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 3,5-Dimethyl . . . | 3% | 10 | |
| Dinotefuran | 0.06 µg | 37 | |
| | | OBS.* | CALC.** |
| 3,5-Dimethyl . . . + Dinotefuran | 3% + 0.06 µg | 87‡ | 43.30 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 120

Efficacy of 4-Methylcyclohexene, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 4-Methylcyclohexene | 3% | 0 | |
| Dinotefuran | 0.06 µg | 37 | |
| | | OBS.* | CALC.** |
| 4-Methylcyclohexene + Dinotefuran | 3% + 0.06 µg | 57‡ | 37.00 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 121

Efficacy of 7,8-Dihydo-α-ionone, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 7,8-Dihydo-α-ionone | 3% | 50 | |
| Dinotefuran | 0.06 µg | 10 | |
| | | OBS.* | CALC.** |
| 7,8-Dihydo-α-ionone + Dinotefuran | 3% + 0.06 µg | 100‡ | 55.00 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 122

Efficacy of 2,4-Dimethyl-3-cyclohexenecarboxaldehyde, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 2,4-Dimethyl ... | 3% | 37 | |
| Dinotefuran | 0.06 µg | 10 | |
| | | OBS.* | CALC.** |
| 2,4-Dimethyl ... + Dinotefuran | 3% + 0.06 µg | 100‡ | 43.30 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 123

Efficacy of Trivertal, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Trivertal | 3% | 13 | |
| Dinotefuran | 0.06 µg | 10 | |
| | | OBS.* | CALC.** |
| Trivertal + Dinotefuran | 3% + 0.06 µg | 100‡ | 21.70 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 124

Efficacy of 3-Cyclohexene-1-methanol, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 3-Cyclohexene-1-m . . . | 3% | 23 | |
| Dinotefuran | 0.06 µg | 37 | |
| | | OBS.* | CALC.** |
| 3-Cyclohexene-1-m . . . + Dinotefuran | 3% + 0.06 µg | 100‡ | 51.49 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 125

Efficacy of Terpinolene, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Terpinolene | 3% | 13 | |
| Dinotefuran | 0.06 µg | 37 | |
| | | OBS.* | CALC.** |
| Terpinolene + Dinotefuran | 3% + 0.06 µg | 87‡ | 45.19 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 126

Efficacy of Piperonyl Butoxide, Dinotefuran, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Piperonyl Butoxide | 1% | 17 | |
| Dinotefuran | 0.06 µg | 57 | |
| | | OBS.* | CALC.** |
| Piperonyl Butoxide + Dinotefuran | 1% + 0.06 µg | 100‡ | 64.31 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 46

The insecticide thiamethoxam was tested with *perilla* oil analogs against mosquitoes as detailed in Reference Example 1 with results show in Tables 127-137.

TABLE 127

Efficacy of Isophorone, Thiamethoxam, and a combination of both against adult, virgin, female *Aedes aegypti* mosquitoes.

|

TABLE 130-continued

Efficacy of 3,5-Dimethyl-2-cyclohexen-1-one, Thiamethoxam, and a combination of both against adult, virgin, female *Aedes aegypti* mosquitoes.

|  |  | OBS.* | CALC.** |
|---|---|---|---|
| 3,5-Dimethyl . . . + Thiamethoxam | 3% + 0.02 μg | 97‡ | 66.61 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 131

Efficacy of 4-Methylcyclohexene, Thiamethoxam, and a combination of both against adult, virgin, female *Aedes aegypti* mosquitoes.

| ACTIVE INGREDIENT | CONCENTRATION | % MORTALITY AFTER 24 HRS |
|---|---|---|
| 4-Methylcyclohexene | 3% | 0 |
| Thiamethoxam | 0.02 μg | 47 |

|  |  | OBS.* | CALC.** |
|---|---|---|---|
| 4-Methylcyclohexene + Thiamethoxam | 3% + 0.02 μg | 57‡ | 47.00 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 132

Efficacy of 7,8-Dihydro-α-ionone, Thiamethoxam, and a combination of both against adult, virgin, female *Aedes aegypti* mosquitoes.

| ACTIVE INGREDIENT | CONCENTRATION | % MORTALITY AFTER 24 HRS |
|---|---|---|
| 7,8-Dihydro-α-ionone | 3% | 53 |
| Thiamethoxam | 0.0075 μg | 23 |

|  |  | OBS.* | CALC.** |
|---|---|---|---|
| 7,8-Dihydro-α-ionone + Thiamethoxam | 3% + 0.0075 μg | 87‡ | 63.81 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 133

Efficacy of 2,4-Dimethyl-3-cyclohexenecarboxaldehyde, Thiamethoxam, and a combination of both against adult, virgin, female *Aedes aegypti* mosquitoes.

| ACTIVE INGREDIENT | CONCENTRATION | % MORTALITY AFTER 24 HRS |
|---|---|---|
| 2,4-Dimethyl . . . | 3% | 10 |
| Thiamethoxam | 0.0075 μg | 23 |

|  |  | OBS.* | CALC.** |
|---|---|---|---|
| 2,4-Dimethyl . . . + Thiamethoxam | 3% + 0.0075 μg | 100‡ | 30.70 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 134

Efficacy of Trivertal, Thiamethoxam, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Trivertal | 3% | 17 | |
| Thiamethoxam | 0.0075 µg | 23 | |
| | | OBS.* | CALC.** |
| Trivertal + Thiamethoxam | 3% + 0.0075 µg | 90‡ | 36.09 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 135

Efficacy of 3-Cyclohexene-1-methanol, Thiamethoxam, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 3-Cyclohexene-1-m . . . | 3% | 70 | |
| Thiamethoxam | 0.02 µg | 57 | |
| | | OBS.* | CALC.** |
| 3-Cyclohexene-1-m . . . + Thiamethoxam | 3% + 0.02 µg | 100‡ | 87.1 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 136

Efficacy of Terpinolene, Thiamethoxam, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Terpinolene | 3% | 40 | |
| Thiamethoxam | 0.02 µg | 57 | |
| | | OBS.* | CALC.** |
| Terpinolene + Thiamethoxam | 3% + 0.02 µg | 100‡ | 74.2 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 137

Efficacy of Pipeonyl Butoxide, Thiamethoxam, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Piperonyl Butoxide | 1% | 67 | |
| Thiamethoxam | 0.02 µg | 87 | |
| | | OBS.* | CALC.** |
| Piperonyl Butoxide + Thiamethoxam | 1% + 0.02 µg | 97‡ | 95.71 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

Example 47

The insecticide clothianidin was tested with *perilla* oil analogs against mosquitoes as detailed in Reference Example 1 with results show in Tables 138-148.

TABLE 138

Efficacy of Isophorone, Clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Isophorone | 3% | 60 | |
| Clothianidin | 0.02 µg | 43 | |
| | | OBS.* | CALC.** |
| Isophorone + Clothianidin | 3% + 0.02 µg | ‡100 | 77.2 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 139

Efficacy of 1-Methyl-1-cyclohexene, Clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 1-Methyl-1-cyclohexene | 3% | 0 | |
| Clothianidin | 0.02 µg | 43 | |
| | | OBS.* | CALC.** |
| 1-Methyl-1-cyclohexene + Clothianidin | 3% + 0.02 µg | ‡90 | 43 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 140

Efficacy of 1-tert-Butyl-1-cyclohexene, Clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 1-tert-Butyl ... | 3% | 10 | |
| Clothianidin | 0.02 µg | 43 | |

TABLE 140-continued

Efficacy of 1-tert-Butyl-1-cyclohexene, Clothianidin, and a combination of both against adult, virgin, female *Aedes aegypti* mosquitoes.

| | | OBS.* | CALC.** |
|---|---|---|---|
| 1-tert-Butyl ... + Clothianidin | 3% + 0.02 µg | ‡73 | 48.7 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 141

Efficacy of 3,5-Dimethyl-2-cyclohexen-1-one, Clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 3,5-Dimethyl ... | 3% | 37 | |
| Clothianidin | 0.02 µg | 43 | |
| | | OBS.* | CALC.** |
| 3,5-Dimethyl ... + Clothianidin | 3% + 0.02 µg | ‡97 | 64.09 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 142

Efficacy of 4-Methylcyclohexene, Clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 4-Methylcyclohexene | 3% | 0 | |
| Clothianidin | 0.02 µg | 43 | |
| | | OBS.* | CALC.** |
| 4-Methylcyclohexene + Clothianidin | 3% + 0.02 µg | ‡83 | 43 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 143

Efficacy of 7,8-Dihydro-α-ionone, Clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 7,8-Dihydro-α-ionone | 3% | 20 | |
| Clothianidin | 0.02 µg | 50 | |
| | | OBS.* | CALC.** |
| 7,8-Dihydro-α-ionone + Clothianidin | 3% + 0.02 µg | ‡ 100 | 60 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 144

Efficacy of 2,4-Dimethyl-3-cyclohexenecarboxaldehyde, Clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 2,4-Dimethyl ... | 3% | 27 | |
| Clothianidin | 0.02 µg | 50 | |
| | | OBS.* | CALC.** |
| 2,4-Dimethyl ... + Clothianidin | 3% + 0.02 µg | ‡ 93 | 63.5 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 145

Efficacy of Trivertal, Clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Trivertal | 3% | 10 | |
| Clothianidin | 0.02 µg | 50 | |
| | | OBS.* | CALC.** |
| Trivertal + Clothianidin | 3% + 0.02 µg | ‡ 67 | 55 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 146

Efficacy of 3-Cyclohexene-1-methanol, Clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 3-Cyclohexene-1-m ... | 3% | 40 | |
| Clothianidin | 0.015 µg | 0 | |
| | | OBS.* | CALC.** |
| 3-Cyclohexene-1-m ... + Clothianidin | 3% + 0.015 µg | ‡ 100 | 40 |

*Obs. = observed efficacy

**Calc. = efficacy calculated using Colby (1967) formula

‡ Since the actual insecticidal kill rate exceeds the calculated value, then the action of the combination is super-additive or a synergistic effect is present.

TABLE 147

Efficacy of Terpinolene, Clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Terpinolene | 3% | 37 | |
| Clothianidin | 0.015 μg | 0 | |
| | | OBS.* | CALC.** |
| Terpinolene + Clothianidin | 3% + 0.015 μg | ‡ 100 | 37 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 148

Efficacy of Piperonyl Butoxide, Clothianidin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Piperonyl Butoxide | 1% | 63 | |
| Clothianidin | 0.01 μg | 47 | |
| | | OBS.* | CALC.** |
| Piperonyl Butoxide + Clothianidin | 1% + 0.01 μg | ‡ 97 | 80.39 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

Example 48

The insecticide imidacloprid was tested with perillaldehyde against mosquitoes as detailed in Reference Example 1 with results show in Table 149.

TABLE 149

Efficacy of perillaldehyde, imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Perillaldehyde | 2% | 30 | |
| Imidacloprid | 0.0025 μg | 83 | |
| | | OBS.* | CALC.** |
| Perillaldehyde + Imidacloprid | 2% + 0.0025 μg | 73‡ | 88.1 |

*Obs. = observed efficacy
**Calc. = efficacy calculated using Colby (1967) formula
‡ Since the actual insecticidal kill rate does not exceed the calculated value, then the action of the combination is not super-additive or synergistic.

Example 49

The insecticide imidacloprid was tested with *perilla*-oil analogs against mosquitoes as detailed in Reference Example 1 with results show in Tables 150-160.

TABLE 150

Efficacy of Isophorone, Imidacloprid, and a combination of both against adult, virgin, female *Aedes aegypti* mosquitoes.

| ACTIVE INGREDIENT | CONCENTRATION | % MORTALITY AFTER 24 HRS |
|---|---|---|
| Isophorone | 3% | 37 |
| Imidacloprid | 0.005 μg | 30 |

TABLE 150-continued

Efficacy of Isophorone, Imidacloprid, and a combination of both against adult, virgin, female *Aedes aegypti* mosquitoes.

|  |  | OBS.* | CALC.** |
|---|---|---|---|
| Isophorone + Imidacloprid | 3% + 0.005 µg | 67‡ | 55.9 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 151

Efficacy of 1-Methyl-1-cyclohexene, Imidacloprid, and a combination of both against adult, virgin, female *Aedes aegypti* mosquitoes.

| ACTIVE INGREDIENT | CONCENTRATION | % MORTALITY AFTER 24 HRS |
|---|---|---|
| 1-Methyl-1-cyclohexene | 3% | 0 |
| Imidacloprid | 0.005 µg | 30 |

|  |  | OBS.* | CALC.** |
|---|---|---|---|
| 1-Methyl-1-cyclohexene + Imidacloprid | 3% + 0.005 µg | 27‡ | 30 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 152

Efficacy of 1-tert-Butyl-1-cyclohexene, Imidacloprid, and a combination of both against adult, virgin, female *Aedes aegypti* mosquitoes.

| ACTIVE INGREDIENT | CONCENTRATION | % MORTALITY AFTER 24 HRS |
|---|---|---|
| 1-tert-Butyl ... | 3% | 40 |
| Imidacloprid | 0.005 µg | 30 |

|  |  | OBS.* | CALC.** |
|---|---|---|---|
| 1-tert-Butyl ... + Imidacloprid | 3% + 0.005 µg | 80‡ | 58 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 153

Efficacy of 3,5-Dimethyl-2-cyclohexen-1-one, Imidacloprid, and a combination of both against adult, virgin, female *Aedes aegypti* mosquitoes.

| ACTIVE INGREDIENT | CONCENTRATION | % MORTALITY AFTER 24 HRS |
|---|---|---|
| 3,5-Dimethyl ... | 3% | 40 |
| Imidacloprid | 0.005 µg | 30 |

|  |  | OBS.* | CALC.** |
|---|---|---|---|
| 3,5-Dimethyl ... + Imidacloprid | 3% + 0.005 µg | 57‡ | 58 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 154

Efficacy of 4-Methylcyclohexene, Imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 4-Methylcyclohexene | 3% | 0 | |
| Imidacloprid | 0.005 µg | 30 | |
| | | OBS.* | CALC.** |
| 4-Methylcyclohexene + Imidacloprid | 3% + 0.005 µg | 53‡ | 30 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 155

Efficacy of 7,8-Dihydro-α-ionone, Imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 7,8-Dihydro-α-ionone | 3% | 3 | |
| Imidacloprid | 0.005 µg | 30 | |
| | | OBS.* | CALC.** |
| 7,8-Dihydro-α-ionone + Imidacloprid | 3% + 0.005 µg | 13‡ | 32.1 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 156

Efficacy of 2,4-Dimethyl-3-cyclohexenecarboxaldehyde, Imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 2,4-Dimethyl ... | 3% | 33 | |
| Imidacloprid | 0.005 µg | 30 | |
| | | OBS.* | CALC.** |
| 2,4-Dimethyl ... + Imidacloprid | 3% + 0.005 µg | 90‡ | 53.1 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 157

Efficacy of Trivertal, Imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Trivertal | 3% | 23 | |
| Imidacloprid | 0.005 µg | 30 | |
| | | OBS.* | CALC.** |
| Trivertal + Imidacloprid | 3% + 0.005 µg | 87‡ | 46.1 |

*Obs = observed efficacy
**Calc. = efficacy calculated using Colby (1967) formula
‡Since the actual insecticidal kill rate exceeds the calculated value, then the action of the combination is super-additive or a synergistic effect is present.

TABLE 158

Efficacy of 3-Cyclohexene-1-methanol, Imidacloprid, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 3-Cyclohexene-1-m ... | 3% | 77 | |
| Imidacloprid | 0.005 µg | 40 | |
| | | OBS.* | CALC.** |
| 3-Cyclohexene-1-m ... + Imidacloprid | 3% + 0.005 µg | 97‡ | 86.2 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 159

Efficacy of Terpinolene, Imidacloprid, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| Terpinolene | 3% | 23 | |
| Imidacloprid | 0.005 μg | 40 | |
| | | OBS.* | CALC.** |
| Terpinolene + Imidacloprid | 3% + 0.005 μg | 70‡ | 53.8 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 160

Efficacy of Piperonyl Butoxide, Imidacloprid, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| Piperonyl Butoxide | 1% | 17 | |
| Imidacloprid | 0.003 μg | 23 | |
| | | OBS.* | CALC.** |
| Piperonyl Butoxide + Imidacloprid | 1% + 0.003 μg | 100‡ | 36.09 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 50

The insecticide nitenpyram was tested with *perilla* oil and various perillaldehyde analogs against mosquitoes as detailed in Reference Example 1 with results show in Tables 161-164.

TABLE 161

Efficacy of Perilla oil, Nitenpyram, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| Perilla oil | 1% | 0 | |
| Nitenpyram | 0.008 μg | 53 | |
| | | OBS.* | CALC.** |
| Perilla oil + Nitenpyram | 1% + 0.008 μg | 97‡ | 53 |
| Perilla oil | 2% | 17 | |
| Nitenpyram | 0.008 μg | 53 | |
| | | OBS.* | CALC.** |
| Perilla oil + Nitenpyram | 2% + 0.008 μg | 97‡ | 60.99 |
| Perilla oil | 3% | 60 | |
| Nitenpyram | 0.008 μg | 53 | |
| | | OBS.* | CALC.** |
| Perilla oil + Nitenpyram | 3% + 0.008 μg | 100‡ | 81.2 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 162

Efficacy of Farnasene, Nitenpyram, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| Farnasene | 3% | 7 | |
| Nitenpyram | 0.008 μg | 3 | |
| | | OBS.* | CALC.** |
| Farnasene + Nitenpyram | 3% + 0.008 μg | 93‡ | 9.79 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 163

Efficacy of Linolenic acid, Nitenpyram, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| Linolenic acid | 3% | 13 | |
| Nitenpyram | 0.008 μg | 3 | |
| | | OBS.* | CALC.** |
| Linolenic acid + Nitenpyram | 3% + 0.008 μg | 93‡ | 15.61 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 164

Efficacy of β-Caryophyllene, Nitenpyram, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| β-Caryophyllene | 3% | 10 | |
| Nitenpyram | 0.008 μg | 53 | |
| | | OBS.* | CALC.** |
| β-Caryophyllene + Nitenpyram | 3% + 0.008 μg | 83‡ | 57.7 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 51

The pyrethrins were tested with *perilla* oil analogs against mosquitoes as detailed in Reference Example 1 with results show in Tables 165-174.

TABLE 165

Efficacy of Isophorone, Pyrethrins, and a combination of both against adult, virgin, female *Aedes aegypti* mosquitoes.

| ACTIVE INGREDIENT | CONCEN-TRATION | % MORTALITY AFTER 24 HRS |
|---|---|---|
| Isophorone | 3% | 67 |
| Pyrethrins | 0.001 μg | 30 |

TABLE 165-continued

Efficacy of Isophorone, Pyrethrins, and a combination of both against adult, virgin, female *Aedes aegypti* mosquitoes.

| | | OBS.* | CALC.** |
|---|---|---|---|
| Isophorone + Pyrethrins | 3% + 0.001 μg | 83 ‡ | 76.9 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 166

Efficacy of 1-Methyl-1-cyclohexene, Pyrethrins, and a combination of both against adult, virgin, female *Aedes aegypti* mosquitoes.

| ACTIVE INGREDIENT | CONCEN-TRATION | % MORTALITY AFTER 24 HRS |
|---|---|---|
| 1-Methyl-1-cyclohexene | 3% | 27 |
| Pyrethrins | 0.001 μg | 30 |

| | | OBS.* | CALC.** |
|---|---|---|---|
| 1-Methyl-1-cyclohexene + Pyrethrins | 3% + 0.001 μg | 80 ‡ | 48.9 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 167

Efficacy of 1-tert-Butyl-1-cyclohexene, Pyrethrins, and a combination of both against adult, virgin, female *Aedes aegypti* mosquitoes.

| ACTIVE INGREDIENT | CONCEN-TRATION | % MORTALITY AFTER 24 HRS |
|---|---|---|
| 1-tert-Butyl . . . | 3% | 3 |
| Pyrethrins | 0.001 μg | 30 |

| | | OBS.* | CALC.** |
|---|---|---|---|
| 1-tert-Butyl . . . + Pyrethrins | 3% + 0.001 μg | 87 ‡ | 32.1 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 168

Efficacy of 3,5-Dimethyl-2-cyclohexen-1-one, Pyrethrins, and a combination of both against adult, virgin, female *Aedes aegypti* mosquitoes.

| ACTIVE INGREDIENT | CONCEN-TRATION | % MORTALITY AFTER 24 HRS |
|---|---|---|
| 3,5-Dimethyl . . . | 3% | 70 |
| Pyrethrins | 0.001 μg | 63 |

| | | OBS.* | CALC.** |
|---|---|---|---|
| 3,5-Dimethyl . . . + Pyrethrins | 3% + 0.001 μg | 97 ‡ | 88.9 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 169

Efficacy of 4-Methylcyclohexene, Pyrethrins, and a combination of both against adult, virgin, female *Aedes aegypti* mosquitoes.

| ACTIVE INGREDIENT | CONCEN-TRATION | % MORTALITY AFTER 24 HRS |
|---|---|---|
| 4-Methylcyclohexene | 3% | 3 |
| Pyrethrins | 0.001 μg | 63 |

| | | OBS.* | CALC.** |
|---|---|---|---|
| 4-Methylcyclohexene + Pyrethrins | 3% + 0.001 μg | 80 ‡ | 64.11 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 170

Efficacy of 7,8-Dihydro-α-ionone, Pyrethrins, and a combination of both against adult, virgin, female *Aedes aegypti* mosquitoes.

| ACTIVE INGREDIENT | CONCEN-TRATION | % MORTALITY AFTER 24 HRS |
|---|---|---|
| 7,8-Dihydro-α-ionone | 3% | 63 |
| Pyrethrins | 0.001 μg | 67 |

| | | OBS.* | CALC.** |
|---|---|---|---|
| 7,8-Dihydro-α-ionone + Pyrethrins | 3% + 0.001 μg | 77 ‡ | 87.79 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 171

Efficacy of 2,4-Dimethyl-3-cyclohexenecarboxaldehyde, Pyrethrins, and a combination of both against adult, virgin, female *Aedes aegypti* mosquitoes.

| ACTIVE INGREDIENT | CONCEN-TRATION | % MORTALITY AFTER 24 HRS |
|---|---|---|
| 2,4-Dimethyl . . . | 3% | 30 |
| Pyrethrins | 0.001 μg | 67 |

| | | OBS.* | CALC.** |
|---|---|---|---|
| 2,4-Dimethyl . . . + Pyrethrins | 3% + 0.001 μg | 93 ‡ | 76.9 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 172

Efficacy of Trivertal, Pyrethrins, and a combination of both against adult, virgin, female *Aedes aegypti* mosquitoes.

| ACTIVE INGREDIENT | CONCEN-TRATION | % MORTALITY AFTER 24 HRS |
|---|---|---|
| Trivertal | 3% | 43 |
| Pyrethrins | 0.001 μg | 67 |

| | | OBS.* | CALC.** |
|---|---|---|---|
| Trivertal + Pyrethrins | 3% + 0.001 μg | 90 ‡ | 81.19 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 173

Efficacy of 3-Cyclohexene-1-methanol, Pyrethrins, and a combination of both against adult, virgin, female *Aedes aegypti* mosquitoes.

| ACTIVE INGREDIENT | CONCEN-TRATION | % MORTALITY AFTER 24 HRS |
|---|---|---|
| 3-Cyclohexene-1-m . . . | 3% | 47 |
| Pyrethrins | 0.001 µg | 37 |

TABLE 173-continued

Efficacy of 3-Cyclohexene-1-methanol, Pyrethrins, and a combination of both against adult, virgin, female *Aedes aegypti* mosquitoes.

| | | OBS.* | CALC.** |
|---|---|---|---|
| 3-Cyclohexene-1-m . . . + Pyrethrins | 3% + 0.001 µg | 87‡ | 66.61 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 174

Efficacy of Terpinolene, Pyrethrins, and a combination of both against adult, virgin, female *Aedes aegypti* mosquitoes.

| ACTIVE INGREDIENT | CONCENTRATION | % MORTALITY AFTER 24 HRS |
|---|---|---|
| Terpinolene | 3% | 37 |
| Pyrethrins | 0.001 µg | 37 |

| | | OBS.* | CALC.** |
|---|---|---|---|
| Terpinolene + Pyrethrins | 3% + 0.001 µg | 97‡ | 60.31 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 52

The insecticide permethrin was tested with *perilla* oil analogs against mosquitoes as detailed in Reference Example 1 with results shown in Tables 175-184

TABLE 175

Efficacy of Isophorone, Permethrin, and a combination of both against adult, virgin, female *Aedes aegypti* mosquitoes.

| ACTIVE INGREDIENT | CONCENTRATION | % MORTALITY AFTER 24 HRS |
|---|---|---|
| Isophorone | 3% | 60 |
| Permethrin | 0.0004 µg | 47 |

| | | OBS.* | CALC.** |
|---|---|---|---|
| Isophorone + Permethrin | 3% + 0.0004 µg | 80‡ | 78.8 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 176

Efficacy of 1-Methyl-1-cyclohexene, Permethrin, and a combination of both against adult, virgin, female *Aedes aegypti* mosquitoes.

| ACTIVE INGREDIENT | CONCENTRATION | % MORTALITY AFTER 24 HRS |
|---|---|---|
| 1-Methyl-1-cyclohexene | 3% | 10 |
| Permethrin | 0.0004 µg | 47 |

| | | OBS.* | CALC.** |
|---|---|---|---|
| 1-Methyl-1-cyclohexene + Permethrin | 3% + 0.0004 µg | 80‡ | 52.3 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 177

Efficacy of 1-tert-Butyl-1-cyclohexene, Permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 1-tert-Butyl . . . | 3% | 47 | |
| Permethrin | 0.0004 µg | 47 | |
| | | OBS.* | CALC.** |
| 1-tert-Butyl . . . + Permethrin | 3% + 0.0004 µg | 93‡ | 71.91 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 178

Efficacy of 3,5-Dimethyl-2-cyclohexen-1-one, Permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 3,5-Dimethyl . . . | 3% | 57 | |
| Permethrin | 0.0004 µg | 53 | |
| | | OBS.* | CALC.** |
| 3,5-Dimethyl . . . + Permethrin | 3% + 0.0004 µg | 87‡ | 79.79 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 179

Efficacy of 4-Methylcyclohexene, Permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 4-Methylcyclohexene | 3% | 3 | |
| Permethrin | 0.0004 µg | 47 | |
| | | OBS.* | CALC.** |
| 4-Methylcyclohexene + Permethrin | 3% + 0.0004 µg | 57‡ | 48.59 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 180

Efficacy of 7,8-Dihydro-α-ionone, Permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 7,8-Dihydro-α-ionone | 3% | 37 | |
| Permethrin | 0.0004 µg | 53 | |
| | | OBS.* | CALC.** |
| 7,8-Dihydro-α-ionone + Permethrin | 3% + 0.0004 µg | 60‡ | 70.39 |

*Obs. = observed efficacy

**Calc. = efficacy calculated using Colby (1967) formula

‡Since the actual insecticidal kill rate exceeds the calculated value, then the action of the combination is super-additive or a synergistic effect is present.

TABLE 181

Efficacy of 2,4-Dimethyl-3-cyclohexenecarboxaldehyde, Permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 2,4-Dimethyl . . . | 3% | 47 | |
| Permethrin | 0.0004 µg | 53 | |
| | | OBS.* | CALC.** |
| 2,4-Dimethyl . . . + Permethrin | 3% + 0.0004 µg | 83‡ | 75.09 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 182

Efficacy of Trivertal, Permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Trivertal | 3% | 20 | |
| Permethrin | 0.0004 µg | 53 | |
| | | OBS.* | CALC.** |
| Trivertal + Permethrin | 3% + 0.0004 µg | 60‡ | 62.4 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 183

Efficacy of 3-Cyclohexene-1-methanol, Permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 3-Cyclohexene-1-methanol | 3% | 57 | |
| Permethrin | 0.0003 µg | 37 | |
| | | OBS.* | CALC.** |
| 3-Cyclohexene-1-methanol + Permethrin | 3% + 0.0003 µg | 100‡ | 72.91 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 184

Efficacy of Terpinolene, Permethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Terpinolene | 3% | 17 | |
| Permethrin | 0.0003 µg | 37 | |
| | | OBS.* | CALC.** |
| Terpinolene + Permethrin | 3% + 0.0003 µg | 97‡ | 47.71 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 53

The insecticide etofenprox was tested with *perilla* oil against mosquitoes as detailed in Reference Example 1 with results show in Table 185.

TABLE 185

Efficacy of Perilla oil, Etofenprox, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Perilla oil | 2% | 0 | |
| Etofenprox | 0.001 µg | 27 | |
| | | OBS.* | CALC.** |
| Perilla oil + Etofenprox | 2% + 0.001 µg | 43‡ | 27 |
| Perilla oil | 3% | 73 | |
| Etofenprox | 0.001 µg | 40 | |
| | | OBS.* | CALC.** |
| Perilla oil + Etofenprox | 3% + 0.001 µg | 87‡ | 83.8 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 54

The insecticide etofenprox was tested with *perilla* oil analogs against mosquitoes as detailed in Reference Example 1 with results show in Tables 186-195.

TABLE 186

Efficacy of Isophorone, Etofenprox, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Isophorone | 3% | 57 | |
| Etofenprox | 0.0007 µg | 10 | |
| | | OBS.* | CALC.** |
| Isophorone + Etofenprox | 3% + 0.0007 µg | 97‡ | 61.3 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 187

Efficacy of 1-Methyl-1-cyclohexane, Etofenprox, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 1-Methyl-1-cyclohexane | 3% | 3 | |
| Etofenprox | 0.0007 µg | 10 | |
| | | OBS.* | CALC.** |
| 1-Methyl-1-cyclohexane + Etofenprox | 3% + 0.0007 µg | 53‡ | 12.7 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 188

Efficacy of 1-tert-Butyl-1-cyclohexene, Etofenprox, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 1-tert-Butyl . . . | 3% | 7 | |
| Etofenprox | 0.0007 µg | 10 | |
| | | OBS.* | CALC.** |
| 1-tert-Butyl . . . + Etofenprox | 3% + 0.0007 µg | 60‡ | 16.3 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 189

Efficacy of 3,5-Dimethyl-2-cyclohexen-1-one, Etofenprox, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| 3,5-Dimethyl . . . | 3% | 33 | |
| Etofenprox | 0.0007 µg | 10 | |
| | | OBS.* | CALC.** |
| 3,5-Dimethyl . . . + Etofenprox | 3% + 0.0007 µg | 87‡ | 39.7 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 190

Efficacy of 4-Methylcyclohexene, Etofenprox, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| 4-Methylcyclohexene | 3% | 3 | |
| Etofenprox | 0.0007 µg | 10 | |
| | | OBS.* | CALC.** |
| 4-Methylcyclohexene + Etofenprox | 3% + 0.0007 µg | 53‡ | 12.7 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 191

Efficacy of 7,8-Dihydro-α-ionone, Etofenprox, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| 7,8-Dihydro-α-ionone | 3% | 33 | |
| Etofenprox | 0.0007 µg | 10 | |
| | | OBS.* | CALC.** |
| 7,8-Dihydro-α-ionone + Etofenprox | 3% + 0.0007 µg | 73‡ | 39.7 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 192

Efficacy of 2,4-Dimethyl-3-cyclohexenecarboxaldehyde, Etofenprox, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| 2,4-Dimethyl . . . | 3% | 23 | |
| Etofenprox | 0.0007 µg | 10 | |
| | | OBS.* | CALC.** |
| 2,4-Dimethyl . . . + Etofenprox | 3% + 0.0007 µg | 17‡ | 30.7 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 193

Efficacy of Trivertal, Etofenprox, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| Trivertal | 3% | 20 | |
| Etofenprox | 0.0007 µg | 10 | |
| | | OBS.* | CALC.** |
| Trivertal + Etofenprox | 3% + 0.0007 µg | 70‡ | 28 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 194

Efficacy of 3-Cyclohexene-1-methanol, Etofenprox, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| 3-Cyclohexene-1-m . . . | 3% | 47 | |
| Etofenprox | 0.0007 µg | 3 | |
| | | OBS.* | CALC.** |
| 3-Cyclohexene-1-m . . . + Etofenprox | 3% + 0.0007 µg | 93‡ | 48.59 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 195

Efficacy of Terpinolene, Etofenprox, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| Terpinolene | 3% | 37 | |
| Etofenprox | 0.0007 µg | 3 | |
| | | OBS.* | CALC.** |
| Terpinolene + Etofenprox | 3% + 0.0007 µg | 77‡ | 38.89 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 55

The insecticide sumithrin was tested with *perilla* oil against mosquitoes as detailed in Reference Example 1 with results show in Table 196.

TABLE 196

Efficacy of Perilla oil, Sumithrin, and a combination of both against adult, virgin, female *Aedes aegypti* mosquitoes.

| ACTIVE INGREDIENT | CONCEN-TRATION | % MORTALITY AFTER 24 HRS |
|---|---|---|
| Perilla oil | 3% | 20 |
| Sumithrin | 0.0007 µg | 27 |

TABLE 196-continued

Efficacy of Perilla oil, Sumithrin, and a combination of both against adult, virgin, female *Aedes aegypti* mosquitoes.

|  |  | OBS.* | CALC.** |
|---|---|---|---|
| Perilla oil + Sumithrin | 3% + 0.0007 μg | 57 ‡ | 41.6 |
| Perilla oil | 4% |  | 17 |
| Sumithrin | 0.0007 μg |  | 27 |

|  |  | OBS.* | CALC.** |
|---|---|---|---|
| Perilla oil + Sumithrin | 4% + 0.0007 μg | 80 ‡ | 39.41 |
| Perilla oil | 5% |  | 37 |
| Sumithrin | 0.0007 μg |  | 27 |

|  |  | OBS.* | CALC.** |
|---|---|---|---|
| Perilla oil + Sumithrin | 5% + 0.0007 μg | 77 ‡ | 54.01 |
| Perilla oil | 6% |  | 50 |
| Sumithrin | 0.0007 μg |  | 27 |

|  |  | OBS.* | CALC.** |
|---|---|---|---|
| Perilla oil + Sumithrin | 6% + 0.0007 μg | 93 ‡ | 63.5 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

Example 56

The insecticide sumithrin was tested with *perilla* oil analogs against mosquitoes as detailed in Reference Example 1 with results show in Tables 197-206.

TABLE 197

Efficacy of Isophorone, Sumithrin, and a combination of both against adult, virgin, female *Aedes aegypti* mosquitoes.

| ACTIVE INGREDIENT | CONCEN-TRATION | % MORTALITY AFTER 24 HRS |
|---|---|---|
| Isophorone | 3% | 30 |
| Sumithrin | 0.0007 μg | 43 |

|  |  | OBS.* | CALC.** |
|---|---|---|---|
| Isophorone acid + Sumithrin | 3% + 0.0007 μg | 90 ‡ | 60.1 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 198

Efficacy of 1-Methyl-1-cyclohexene, Sumithrin, and a combination of both against adult, virgin, female *Aedes aegypti* mosquitoes.

| ACTIVE INGREDIENT | CONCEN-TRATION | % MORTALITY AFTER 24 HRS |
|---|---|---|
| 1-Methyl-1-cyclohexene | 3% | 7 |
| Sumithrin | 0.0007 μg | 43 |

|  |  | OBS.* | CALC.** |
|---|---|---|---|
| 1-Methyl-1-cyclohexene + Sumithrin | 3% + 0.0007 μg | 83 ‡ | 46.99 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 199

Efficacy of 1-tert-Butyl-1-cyclohexene, Sumithrin, and a combination of both against adult, virgin, female *Aedes aegypti* mosquitoes.

| ACTIVE INGREDIENT | CONCEN-TRATION | % MORTALITY AFTER 24 HRS |
|---|---|---|
| 1-tert-Butyl . . . | 3% | 47 |
| Sumithrin | 0.0007 μg | 43 |

|  |  | OBS.* | CALC.** |
|---|---|---|---|
| 1-tert-Butyl . . . + Sumithrin | 3% + 0.0007 μg | 87 ‡ | 69.79 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 200

Efficacy of 3,5-Dimethyl-2-cyclohexen-1-one, Sumithrin, and a combination of both against adult, virgin, female *Aedes aegypti* mosquitoes.

| ACTIVE INGREDIENT | CONCEN-TRATION | % MORTALITY AFTER 24 HRS |
|---|---|---|
| 3,5-Dimethyl . . . | 3% | 63 |
| Sumithrin | 0.0007 μg | 43 |

|  |  | OBS.* | CALC.** |
|---|---|---|---|
| 3,5-Dimethyl . . . + Sumithrin | 3% + 0.0007 μg | 93 ‡ | 78.91 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 201

Efficacy of 4-Methylcyclohexene, Sumithrin, and a combination of both against adult, virgin, female *Aedes aegypti* mosquitoes.

| ACTIVE INGREDIENT | CONCEN-TRATION | % MORTALITY AFTER 24 HRS |
|---|---|---|
| 4-Methylcyclohexene | 3% | 0 |
| Sumithrin | 0.0007 μg | 43 |

|  |  | OBS.* | CALC.** |
|---|---|---|---|
| 4-Methylcyclohexene + Sumithrin | 3% + 0.0007 μg | 67 ‡ | 43 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 202

Efficacy of 7,8-Dihydro-α-ionone, Sumithrin, and a combination of both against adult, virgin, female *Aedes aegypti* mosquitoes.

| ACTIVE INGREDIENT | CONCEN-TRATION | % MORTALITY AFTER 24 HRS |
|---|---|---|
| 7,8-Dihydro-α-ionone | 3% | 3 |
| Sumithrin | 0.0007 μg | 43 |

|  |  | OBS.* | CALC.** |
|---|---|---|---|
| 7,8-Dihydro-α-ionone + Sumithrin | 3% + 0.0007 μg | 97 ‡ | 44.71 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 203

Efficacy of 2,4-Dimethyl-3-cyclohexenecarboxaldehyde, Sumithrin, and a combination of both against adult, virgin, female *Aedes aegypti* mosquitoes.

| ACTIVE INGREDIENT | CONCEN-TRATION | % MORTALITY AFTER 24 HRS | |
|---|---|---|---|
| 2,4-Dimethyl . . . | 3% | 47 | |
| Sumithrin | 0.0007 µg | 43 | |
| | | OBS.* | CALC.** |
| 2,4-Dimethyl . . . + Sumithrin | 3% + 0.0007 µg | 47‡ | 69.79 |

*Obs. = observed efficacy
**Calc. = efficacy calculated using Colby (1967) formula
‡Since the actual insecticidal kill rate does not exceed the calculated value, then the action of the combination is not super-additive or synergistic.

TABLE 204

Efficacy of Trivertal, Sumithrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Trivertal | 3% | 40 | |
| Sumithrin | 0.0007 µg | 43 | |
| | | OBS.* | CALC.** |
| Trivertal + Sumithrin | 3% + 0.0007 µg | 37‡ | 65.8 |

*Obs. = observed efficacy
**Calc. = efficacy calculated using Colby (1967) formula
‡Since the actual insecticidal kill rate does not exceed the calculated value, then the action of the combination is not super-additive or synergistic.

TABLE 205

Efficacy of 3-Cyclohexene-1-methanol, Sumithrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 3-Cyclohexene-1-methanol | 3% | 50 | |
| Sumithrin | 0.0003 µg | 27 | |
| | | OBS.* | CALC.** |
| 3-Cyclohexene-1-methanol + Sumithrin | 3% + 0.0003 µg | 90‡ | 63.5 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

TABLE 206

Efficacy of Terpinolene, Sumithrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Terpinolene | 3% | 20 | |
| Sumithrin | 0.0003 µg | 27 | |
| | | OBS.* | CALC.** |
| Terpinolene + Sumithrin | 3% + 0.0003 µg | 67‡ | 41.6 |

*Obs. = observed efficacy
**Calc. = efficacy calculated using Colby (1967) formula
‡Since the actual insecticidal kill rate exceeds the calculated value, then the action of the combination is super-additive or a synergistic effect is present..

Example 57

The insecticide prallethrin was tested with *perilla* oil analogs against mosquitoes as detailed in Reference Example 1 with results show in Tables 207-216.

TABLE 207

Efficacy of Isophorone, Prallethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| Isophorone | 3% | 57 | |
| Prallethrin | 0.0005 µg | 37 | |
| | | OBS.* | CALC.** |
| Isophorone + Prallethrin | 3% + 0.0005 µg | 97‡ | 72.91 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 208

Efficacy of 1-Methyl-1-cyclohexene, Prallethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 1-Methyl-1-cyclohexene | 3% | 40 | |
| Prallethrin | 0.0005 µg | 37 | |
| | | OBS.* | CALC.** |
| 1-Methyl-1-cyclohexene + Prallethrin | 3% + 0.0005 µg | 97‡ | 62.2 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 209

Efficacy of 1-tert-Butyl-1-cyclohexene, Prallethrin, and a combination of both against adult, virgin, female *Aedes aegypti* mosquitoes.

| ACTIVE INGREDIENT | CONCENTRATION | % MORTALITY AFTER 24 HRS | |
|---|---|---|---|
| 1-tert-Butyl . . . | 3% | 30 | |
| Prallethrin | 0.0005 µg | 37 | |
| | | OBS.* | CALC.** |
| 1-tert-Butyl . . . + Prallethrin | 3% + 0.0005 µg | 77‡ | 55.9 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 210

Efficacy of 3,5-Dimethyl-2-cyclohexen-1one, Prallethrin, and a combination of both against adult, virgin, female *Aedes aegypti* mosquitoes.

| ACTIVE INGREDIENT | CONCENTRATION | % MORTALITY AFTER 24 HRS |
|---|---|---|
| 3.5-Dimethyl . . . | 3% | 30 |
| Prallethrin | 0.0005 µg | 37 |

TABLE 210-continued

Efficacy of 3,5-Dimethyl-2-cyclohexen-1one, Prallethrin, and a combination of both against adult, virgin, female *Aedes aegypti* mosquitoes.

|  |  | OBS.* | CALC.** |
|---|---|---|---|
| 3,5-Dimethyl . . . + Prallethrin | 3% + 0.0005 μg | 90 ‡ | 55.9 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 211

Efficacy of 4-Methylcyclohexene, Prallethrin, and a combination of both against adult, virgin, female *Aedes aegypti* mosquitoes.

| ACTIVE INGREDIENT | CONCENTRATION | % MORTALITY AFTER 24 HRS |
|---|---|---|
| 4-Methylcyclohexene | 3% | 0 |
| Prallethrin | 0.0005 μg | 37 |

|  |  | OBS.* | CALC.** |
|---|---|---|---|
| 4-Methylcyclohexene + Prallethrin | 3% + 0.0005 μg | 57 ‡ | 37 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 212

Efficacy of 7,8-Dihydro-α-ionone, Prallethrin, and a combination of both against adult, virgin, female *Aedes aegypti* mosquitoes.

| ACTIVE INGREDIENT | CONCENTRATION | % MORTALITY AFTER 24 HRS |
|---|---|---|
| 7,8-Dihydro-α-ionone | 3% | 47 |
| Prallethrin | 0.0005 μg | 37 |

|  |  | OBS.* | CALC.** |
|---|---|---|---|
| 7,8-Dihydro-α-ionone + Prallethrin | 3% + 0.0005 μg | 97 ‡ | 66.61 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 213

Efficacy of 2,4-Dimethyl-3-cyclohexenecarboxaldehyde, Prallethrin, and a combination of both against adult, virgin, female *Aedes aegypti* mosquitoes.

| ACTIVE INGREDIENT | CONCENTRATION | % MORTALITY AFTER 24 HRS |
|---|---|---|
| 2,4-Dimethyl . . . | 3% | 13 |
| Prallethrin | 0.0005 μg | 60 |

|  |  | OBS.* | CALC.** |
|---|---|---|---|
| 2,4-Dimethyl . . . + Prallethrin | 3% + 0.0005 μg | 77 ‡ | 65.2 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 214

Efficacy of Trivertal, Prallethrin, and a combination of both against adult, virgin, female *Aedes aegypti* mosquitoes.

| ACTIVE INGREDIENT | CONCENTRATION | % MORTALITY AFTER 24 HRS |
|---|---|---|
| Trivertal | 3% | 0 |
| Prallethrin | 0.0005 μg | 60 |

|  |  | OBS.* | CALC.** |
|---|---|---|---|
| Trivertal + Prallethrin | 3% + 0.0005 μg | 90 ‡ | 60 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 215

Efficacy of 3-Cyclohexene-1-methanol, Prallethrin, and a combination of both against adult, virgin, female *Aedes aegypti* mosquitoes.

| ACTIVE INGREDIENT | CONCENTRATION | % MORTALITY AFTER 24 HRS |
|---|---|---|
| 3-Cyclohexene-1-methanol | 3% | 7 |
| Prallethrin | 0.0004 μg | 40 |

|  |  | OBS.* | CALC.** |
|---|---|---|---|
| 3-Cyclohexene-1-methanol + Prallethrin | 3% + 0.0004 μg | 87 ‡ | 44.2 |

*Obs. = observed efficacy
**Calc. = efficacy calculated using Colby (1967) formula
‡ Since the actual insecticidal kill rate exceeds the calculated value, then the action of the combination is super-additive or a synergistic effect is present.

TABLE 216

Efficacy of Terpinolene, Prallethrin, and a combination of both against adult, virgin, female *Aedes aegypti* mosquitoes.

| ACTIVE INGREDIENT | CONCENTRATION | % MORTALITY AFTER 24 HRS |
|---|---|---|
| Terpinolene | 3% | 20 |
| Prallethrin | 0.0003 μg | 7 |

|  |  | OBS.* | CALC.** |
|---|---|---|---|
| Terpinolene + Prallethrin | 3% + 0.0003 μg | 93 ‡ | 25.6 |

*Obs. = observed efficacy
**Calc. = efficacy calculated using Colby (1967) formula
‡Since the actual insecticidal kill rate exceeds the calculated value, then the action of the combination is super-additive or a synergistic effect is present.

Example 58

Open Field Caged Mosquito Efficacy Study

Figure 1:
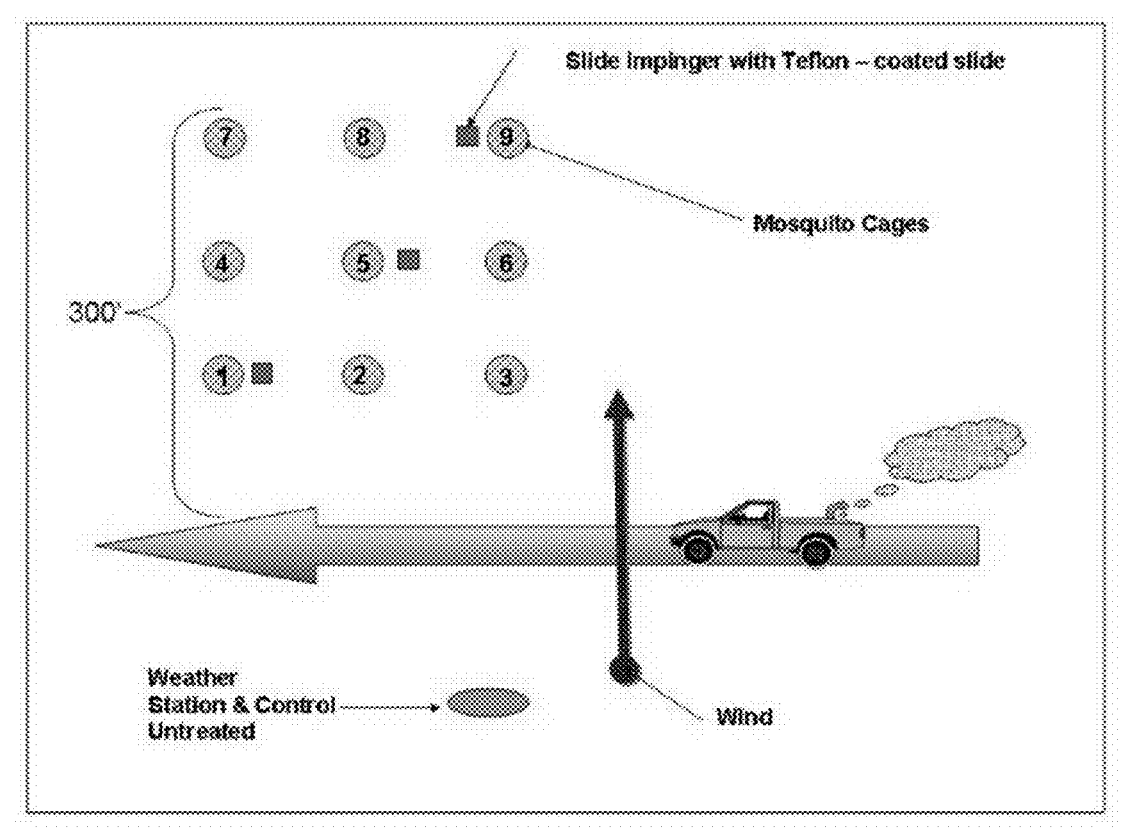

A formulation including 5% pyrethrin, 7% *perilla* oil, and 67% Mineral oil was tested to determine the potential efficacy against adult female mosquitoes in an open field caged study. Spray cages were placed on 5-foot stakes, 1 cage per stake, and at an angle parallel to the spray line. Stakes were placed at 100, 200 and 300 feet down-wind at a 90 angle from the spray line. Cages were placed in three rows 100 feet apart. See FIG. 1. A total of 10 spray cages (9 treated and 1 untreated control) were used in each replicate. 20-25 adult female *Aedes aegypti* mosquitoes were placed in the cylindrical spray cages. The formulation was applied at an application rate of 0.53 oz/acre to the area.

Two replicate experiments were conducted. For each replicate, Droplet VMDs were 13-15 microns, Drop Densities at all distances were +300/cm², the air temperature was 79° F., and the winds were consistent from the East at 6-8 mph. After 1 h, 12 h, and 24 h, the knockdown or mortality was calculated as a percent of the total number of mosquitoes for that replicate and distance. Results are shown in Table 217.

TABLE 217

| Distance from spray line | 1 h knockdown | 12 h knockdown | 24 h Mortality |
| --- | --- | --- | --- |
| Replicate 1 | | | |
| 100 feet | 100% | 100% | 100% |
| 200 feet | 100% | 100% | 100% |
| 300 feet | 100% | 100% | 100% |
| Replicate 2 | | | |
| 100 feet | 98% | 99% | 99.9% |
| 200 feet | 100% | 100% | 99% |
| 300 feet | 100% | 100% | 99.9% |

Example 59

P450 Activity Assay

Cytochrome P450 enzyme solution was prepared by homogenizing 15, 3 to 5 day old, *A. aegypti* females and centrifuging the mixture at 10,000 g for 1 minute. The pellet was discarded, and the supernatant was used as the P450 enzyme stock solution. 10 μL of this P450 enzyme stock and 90 μL of 7-ethoxycoumarin solution (0.526 mM of 7-ethoxycoumarin, 1.11 mM NADPH, 0.05 mM phosphate buffer) was added to each well of the micropipette plate to begin the reaction. During the reaction, the micropipette plate was covered with aluminum foil to prevent photo-bleaching. The reaction was incubated at 30° C. for 4 hours. The reaction was stopped by adding 30 μL of stop solution (0.1 mM glycine, pH 10.4, 50% ethanol). The micropipette plate was then analyzed by measuring the fluorescence (Emission=460 nM, Excitation=360 nM) of each well. High fluorescence was directly related to product, and thus indicated a high level of P450 activity. Conversely, low fluorescence indicated less product and suggested low P450 activity (inhibition).

Measurement of cytochrome P450 enzyme (P450) activity with and without inhibitors are shown in FIG. 2. The control treatment contained acetone. PBO, a known cytochrome p450 inhibitor served as a positive control. Both PBO and perillaldehyde when added to the assay acted as inhibitors. FIG. 2 shows that perillaldehyde at 1% is as potent an inhibitor of P450 as PBO at 2%. Perillaldehyde at 10% is a more potent inhibitor of P450 than PBO at 2%.

Thus, the disclosure provides, among other things, insecticidal compositions.

What is claimed is:

1. An insecticidal composition consisting essentially of (i) insecticidal amounts of a component selected from the group consisting of synthetic prallethrin, synthetic sumithrin, and a combination thereof, and one or more of R-carvone and S-carvone, wherein the R-carvone and S-carvone are isolated, synthetic, or a combination thereof, and (ii) a compound selected from the group consisting of mineral oil, capric caprylic triglyceride, glycerol, polyethylene glycol, wintergreen oil, D-limonene, and a combination thereof.

2. The composition of claim 1, wherein the composition consists essentially of insecticidal amounts of R-carvone and a component selected from the group consisting of synthetic prallethrin, synthetic sumithrin, and a combination thereof, and (ii) a compound selected from the group consisting of mineral oil, capric caprylic triglyceride, glycerol, polyethylene glycol, wintergreen oil, D-limonene, and a combination thereof.

3. The composition of claim 2, wherein the R-carvone is synthetic.

4. The composition of claim 2, wherein the R-carvone is isolated.

5. The composition of claim 2, wherein the compound is a combination of mineral oil and capric caprylic triglyceride.

6. The composition of claim 1, wherein the compound is a combination of mineral oil and capric caprylic triglyceride.

7. The composition of claim 1, wherein the composition consists essentially of insecticidal amounts of S-carvone and a component selected from the group consisting of synthetic prallethrin, synthetic sumithrin, or a combination thereof, and (ii) a compound selected from the group consisting of mineral oil, capric caprylic triglyceride, glycerol, polyethylene glycol, wintergreen oil, D-limonene, and a combination thereof.

8. A method for controlling insects, the method consisting essentially of contacting a population of insects with an effective amount of the composition of claim 1.

9. The method of claim 8, wherein the insect is a mosquito.

10. The method of claim 9, wherein the composition is topically applied to the population in an amount sufficient to kill at least 25% of the population.

11. The method of claim 8, wherein the composition is topically applied to the population in an amount sufficient to kill at least 50% of the population.

12. The method of claim 8, wherein the composition is applied by at least one of an aerosol, mist, fog, spray, vapor, ULV spray, or surface contact treatment.

13. The method of claim 8, wherein the population is exposed to the insecticide so that the composition is ingested by the insects sufficient to kill at least 50% of the population.

14. An insecticidal composition consisting essentially of insecticidal amounts of a component selected from the group consisting of synthetic prallethrin, synthetic sumithrin, and a combination thereof, and one or more of R-carvone and S-carvone, wherein the R-carvone and the S-carvone are isolated, synthetic, or a combination thereof.

15. The composition of claim 14, wherein the composition consists essentially of insecticidal amounts of R-carvone and a component selected from the group consisting of synthetic prallethrin, synthetic sumithrin, and a combination thereof.

16. The composition of claim 15, wherein the R-carvone is synthetic.

17. The composition of claim 15, wherein the R-carvone is isolated.

18. The composition of claim 14, wherein the composition consists essentially of insecticidal amounts of S-carvone and a component selected from the group consisting of synthetic prallethrin, synthetic sumithrin, and a combination thereof.

* * * * *